US008877440B2

(12) United States Patent
Dong et al.

(10) Patent No.: US 8,877,440 B2
(45) Date of Patent: Nov. 4, 2014

(54) CHROMOSOME CONFORMATION ANALYSIS

(75) Inventors: Shoulian Dong, Mountain View, CA (US); Junko F. Stevens, Menlo Park, CA (US); Chunmei Liu, Palo Alto, CA (US); Cora L. Woo, Santa Clara, CA (US); Luz Montesclaros, Pittsburg, CA (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/617,230

(22) Filed: Sep. 14, 2012

(65) Prior Publication Data

US 2013/0084574 A1  Apr. 4, 2013

Related U.S. Application Data

(63) Continuation of application No. 13/475,089, filed on May 18, 2012.

(60) Provisional application No. 61/487,614, filed on May 18, 2011, provisional application No. 61/579,444, filed on Dec. 22, 2011, provisional application No. 61/579,876, filed on Dec. 23, 2011.

(51) Int. Cl.
*C12Q 1/68* (2006.01)

(52) U.S. Cl.
CPC ............ *C12Q 1/6869* (2013.01); *C12Q 1/6827* (2013.01); *C12Q 1/6848* (2013.01); *C12Q 2600/158* (2013.01); *C12Q 2600/178* (2013.01); *C12Q 2600/154* (2013.01); *C12Q 1/6806* (2013.01); *C12Q 1/6886* (2013.01)
USPC ......................................................... 435/6.1

(58) Field of Classification Search
None
See application file for complete search history.

(56) References Cited

U.S. PATENT DOCUMENTS

| 8,663,919 B2 | 3/2014 | Dong et al. |
| 2009/0061425 A1 | 3/2009 | Lo et al. |
| 2010/0081141 A1 | 4/2010 | Chen |

FOREIGN PATENT DOCUMENTS

| EP | 1835038 | 9/2007 |
| EP | 2083090 | 7/2009 |
| WO | 2009/147386 | 12/2009 |
| WO | 2011/146056 | 11/2011 |

OTHER PUBLICATIONS

Hagege, Helene et al, "Quantitative Analysis of Chromosome Conformation Capture Assays (3C-qPCR)", *Nature Protocols,* vol. 2, No. 7, 2007, 1722-1733.
Partial International Search Report for Int'l Appl. No. PCT/US2012/038558 dated Sep. 24, 2012.
International Search Report and Written Opinion for International Appl. No. PCT/US2012/03855 mailed Jan. 15, 2013.
Dekker, Job et al., "Capturing Chromosome Conformation", *Science,* vol. 295, 2002, 1306-1311.
Berensmeier, "Magnetic particles for the separation and purification of nucleic acids", *Applied Microbiology and Biotechnology,* vol. 73, No. 3, Dec. 2006, 495-504 (Epub Oct. 25, 2006).
Intl Application No. PCT/US2012/038558, International Preliminary Report on Patentability mailed Nov. 19, 2013.

*Primary Examiner* — Tracy Vivlemore
*Assistant Examiner* — Karen S Weiler

(57) ABSTRACT

Disclosed herein are compositions, methods and kits for analyzing three-dimensional chromatin and/or chromosome conformation. Method are also disclosed for using the methods disclosed herein for diagnosing diseases such as cancer.

6 Claims, 28 Drawing Sheets

Gene Desert Region

TTCAGAATGGAACATATCGGAAGATACATGCTTTTGAGAAGAAAAGGGGATTTTATGATGGTGTGCTGAA

GCCATAATATGGCTGGATAATCCTATTTTTCTTTTATTTTAAAAAATACTCTGAAATACTTTTAAAAATA
Assay1 & 2 Fw Primer             EcoR I
AACTTTTATTCTTCCTAGTGTTGTGAGAAAAGAGGCCCTTCCTCTATGCCCACGGTAGAATTCCAAGAT
Assay1 Probe                                                Hind III Assay1 Rv Primer
CTGCTCTTTACTGCCAAGTCTTGGAGTCGAGATTAATCACATCTAATTCTTAAGCTTAGAACTTAATGTG
Alu I   Hind III
ACAGATAAGTAGCTTGAAATAAGCTTCATATCTCTTCATTAGTGTTGTATAATTGAAAAAAAGAATATTTT

TATATCATGATTGTACTCTTCAAAAATTCTTCCAAACATAGTCCCAAACCACTACAAATGTCTTAGAAG

TGGGACTTAGAAGCTCCTCAAAGAGCTGAAACAATTGTCTTCCAGAATTCAAGAACCATTGTCGAAAG

TGAAGAATAATTTGTTAATTCATTTTATCTAAAAACTACAGTATGACTTCCCATTCTCCATTCCCAGTGACA

FIG. 8

*Internal adaptor incorporated targets

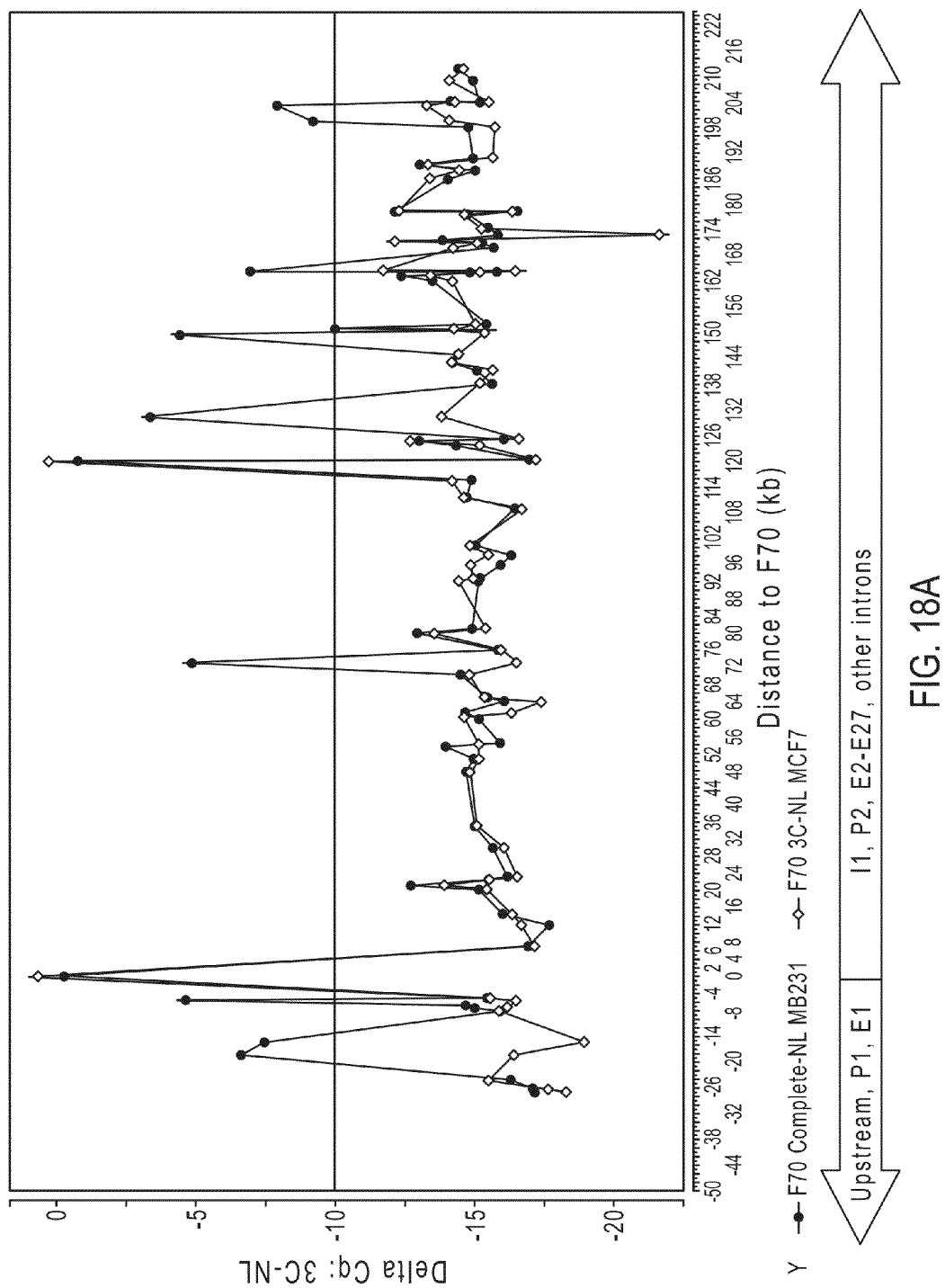

US 8,877,440 B2

CHROMOSOME CONFORMATION ANALYSIS

CROSS-REFERENCE TO RELATED APPLICATIONS

This application is a continuation application of U.S. patent application Ser. No. 13/475,089, filed May 18, 2012, which claims priority to U.S. Provisional Application No. 61/487,614, filed May 18, 2011, U.S. Provisional Application No. 61/579,444, filed Dec. 22, 2011 and U.S. Provisional Application No. 61/579,876, filed Dec. 23, 2011 which disclosures are herein incorporated by reference in their entirety.

FIELD

This disclosure relates to methods, reagents and kits useful for epigenetic analysis of DNA.

BACKGROUND

Epigenetics is the study of heritable changes in gene function that do not involve changes in DNA sequence. These changes can occur due to the chemical modification of specific genes or gene-associated proteins of an organism. These modifications can affect how genes are expressed and used in cells. For example, methylation of specific regions in gene sequences, such as CpG sites, can make these genes less transcriptionally active. Another example is post-translational modification of histone proteins around which genomic DNA is wound. This histone modification can affect the unwinding of the DNA during transcription which, in turn, can affect the expression of the transcribed genes. Furthermore, chromosome conformation or chromatin compaction can also have an effect on gene expression, such as affecting the accessibility of the template to polymerases or changing the proximity between genes and genomic sequences.

Important chromosomal activities and gene expression have been linked with the structural properties of the chromosome, such as their spatial conformation. Furthermore, the local properties of chromatin fibers have also been shown to influence gene expression. Higher order structures of chromatin, such as 30 nm fibers, chromatin loops and axes, and interchromosomal connections have also been shown to play a role in gene expression and recombination.

Epigenetic mechanisms are essential for normal development and maintenance of the normal gene expression pattern in many organisms including humans. Recent studies suggest that epigenetic alterations may be the key initiating events in some forms of cancers and global changes in the epigenome are a hallmark of cancers. Epigenetic mechanisms that modify chromatin structure can be divided into four main categories: 1) DNA methylation, 2) covalent histone modifications and noncovalent mechanisms such as incorporation of histone variants, 3) nucleosome remodeling and 4) non-coding RNAs which include microRNAs (miRNAs). The role of DNA methylation and histone modifications in cancer initiation and progression is well established; however, the changes in chromatin structure that accompany DNA methylation and histone modifications are less well understood The analysis of chromosomal conformation has been complicated by technical limitations. For example, analysis by electron microscopy is laborious and cannot be used to view specific loci; fluorescently-labeled DNA binding proteins permit the visualization of specific loci, but only a few loci can be examined simultaneously. Fluorescence in situ hybridization (FISH) analysis can examine multiple loci, but the severe experimental conditions may adversely affect chromosomal organization.

In an attempt to overcome the limitations of visual chromosomal analysis, methods using the polymerase chain reaction (PCR) have been developed. For example, the chromosome conformation capture (3C) method analyzes overall chromosomal spatial organization and physical properties at a higher resolution (see, Dekker et al., Science 295:1306-1311 (2002)). In 3C experiments, genomic DNA (gDNA) and proteins in the chromosomes are fixed in place by cross-linking. The cross-linked gDNA is digested by a restriction enzyme and ligated before being purified for analysis. Physical interactions between genomic loci are identified as specific cross-ligated DNA elements using PCR amplification. As a result of 3C methods, spatial information is converted to quantifiable DNA sequences. However, the wide adaptation of 3C methods has been hindered by the lack of quantitative process controls and cumbersome protocols.

Derivative methods of 3C, such as 4C and 5C, have also been developed. 4C and 5C differ from 3C only in the analysis of the ligation product. In 4C, the ligation product is first amplified by PCR using two outwardly facing primers from the restriction site to create a circular DNA molecule which is then analyzed by microarray technology. In 5C, the ligation products are mixed with special primers designed to anneal at the ends of the restriction fragment. Analysis is carried out either by use of a microarray or by sequencing against a 3C library of ligation products.

However, there are several disadvantages associated with these 3C-based methods. The assays are time consuming and are not precise and sensitive enough for reactions with low digestion or ligation efficiency. These methods also require significant dilution of the DNA sample. As a result, large quantities of the sample may be needed, which may not always be available. In addition, the 3C-based methods listed above suffer from low throughput and are unable to solve the entire spatial arrangement of the chromatin in the nucleus and therefore must focus on capturing interaction partners of a limited number of loci. The present teachings overcome these and other disadvantages and limitations and are useful for capturing interaction partners in the different regions of chromatin in an unbiased fashion.

BRIEF DESCRIPTION OF THE DRAWINGS

The accompanying drawings, which are incorporated in and constitute a part of this specification, illustrate several exemplary embodiments of the disclosure and together with the description, serve to explain certain teachings. The skilled artisan will understand that the described drawings are for illustration purposes only. The drawings are not intended to limit the scope of the present teachings in any way.

FIG. 8: Shows the locations of the digestion and ligation control assay probes and primers in a gene desert region as described in the present teachings. ENr313 is located in chromosome 16 (SEQ ID NO: 1).

FIGS. 18A and 18B: Graphical representation of PLD1 Intron 1 and Promoter 2 long range cis fragments interaction frequency comparison in MCF-7 and MDA-MB-231 cells.

SUMMARY

Provided herein are methods, compositions and kits that are useful for analyzing the physical interactions between various genomic elements that affect gene regulation, DNA replication and genome organization. Through structures such as loops and bridges, chromatin fibers make multiple physical contacts with genetic elements that can be tens to hundreds of kilobases apart or more. To study these contacts, specifically to analyze the frequency of interaction and proximity between any two genomic loci, chromosome conformation capture methods provided herein may be used. The chromosome conformation capture methods provided herein convert physical interactions into unique ligation products. The concentration of an individual ligation product is correlated to the frequency of looping between the two genomic regions. The abundance of the ligation products may be quantified by methods such as the polymerase chain reaction (PCR), including endpoint PCR, real-time PCR, quantitative PCR (qPCR) and digital PCR (dPCR), and DNA sequencing methods, including fragment analysis, Sanger sequencing, and next-generation sequencing (NGS), including but not limited to, sequencing by ligation (e.g., SOLiD sequencing), proton ion semiconductor sequencing, DNA nanoball sequencing, single molecule sequencing, and nanopore sequencing.

The methods disclosed herein overcome the disadvantages of previously published 3C methods and have the following unexpected advantages: 1) quantitative control assays for restriction digestion, ligation and interaction frequency normalization to allow for precise analysis of the efficiency and quality of the assay; 2) standardized and reproducible conditions and reagents resulting in more efficient and controlled cross-linking, lysis and restriction digestion; 3) improved ligation; 4) increased purity and yield resulting from a rapid and non-toxic purification process that improves DNA quality and increases DNA recovery by an order of magnitude; and 5) time savings resulting from a streamlined workflow reducing the time to result by 50%, as compared to published protocols.

Figure 1:
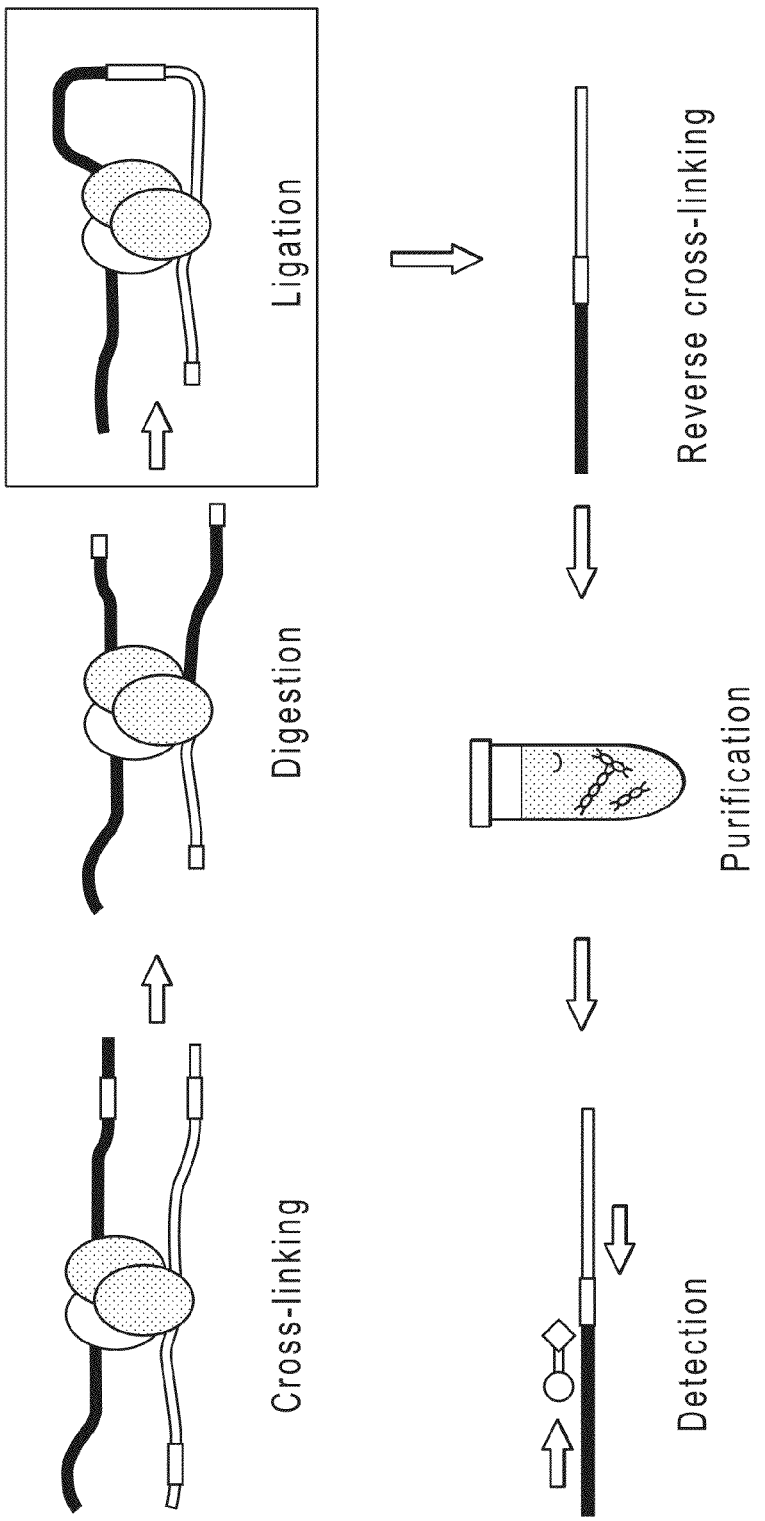
FIG. 1: A schematic representation of the 3C method according to embodiments of the present teachings.

One embodiment provides a method of chromosome conformation analysis (see, FIG. 1), the method including the steps of:

a) isolating cells from a biological sample;

b) incubating the cells with a cross-linking agent to cross-link proteins and DNA (e.g., chromatin or gDNA), thereby forming a cross-linked product;

c) lysing the cells;

d) digesting the DNA with a restriction endonuclease;

e) ligating the digested DNA by incubating with a ligating agent thereby creating a ligation product;

f) reversing the cross-linking;

g) purifying the ligated DNA; and h) analyzing the ligation product.

In one embodiment, the cross-linked product is optionally incubated with a cross-linking quencher. In another embodiment, the cross-linked product is removed from the cross-linking agent by washing or separating the quencher from the cross-linked product. In one embodiment, the cells are in suspension. In another embodiment, the cells are adherent. The cells may be intact, live, permeabilized or otherwise treated depending on the method of isolation.

In one embodiment, the ligation products are analyzed by the polymerase chain reaction (PCR). In preferred embodiments, the PCR can be endpoint PCR, real-time PCR, qPCR and dPCR, most preferably, the PCR is real-time PCR and qPCR. In one embodiment, the ligation products are analyzed by DNA sequencing methods including, but not limited to, fragment analysis, dideoxy sequencing (i.e., Sanger sequencing), Maxam-Gilbert chain termination sequencing, dye terminator sequencing, dye primer sequencing, pyrosequencing, next generation sequencing methods including, high-throughput sequencing, including massively parallel signature sequencing, SOLiD sequencing (e.g., sequencing by ligation), sequencing by hybridization, proton ion semiconductor sequencing, DNA nanoball sequencing, single molecule sequencing, and nanopore sequencing.

In one embodiment, the purifying step includes purifying the ligation product using column purification. In another embodiment, the purifying step includes incubating the ligation product with magnetic beads for a period of time sufficient to allow the ligation product to bind to the magnetic beads. The bound ligation product is collected by centrifugation or by the addition of a magnetic field. The bound ligation product is then eluted from the magnetic beads.

Another embodiment provides a chromosome conformation analysis method that includes a control assay that monitors the undigested template DNA, herein denoted "Assay 1." (see, FIG. 2) Assay 1 uses oligonucleotide primers that specifically hybridize to regions in the target DNA either upstream (herein denoted "forward primer") or downstream (herein denoted "reverse primer") of the restriction endonuclease cutting site. If the restriction site is not digested, the sequence will be amplified. An oligonucleotide probe that hybridizes to a sequence upstream of the restriction site may be used to monitor the presence of the undigested template DNA. In a preferred embodiment, the restriction endonuclease recognizes a six-base cutting sequence. In a more preferred embodiment, the restriction endonuclease is selected from EcoRI and HindIII.

Yet another embodiment provides a chromosome conformation analysis method that includes a control assay that monitors the digested template DNA, herein denoted "Assay 2." (see, FIG. 2) Assay 2 uses oligonucleotides, herein referred to as "bridge oligos," that have a blocked 3' end, a template DNA binding region that hybridizes to the 3' end of the digested DNA, and a 5' region that hybridizes to primer and probe sequences. In the first cycle of PCR, the bridge oligo anneals to the template DNA via the template binding region and the bridge oligo sequence is amplified resulting in a first amplification product. In the second cycle of PCR, first amplification product is incubated with a forward primer that hybridizes to the 5' end of the bridge oligo that contains the primer binding site which is upstream of the restriction endonuclease cutting site, and a reverse primer that hybridizes to the digested DNA which contains the complement of the bridge oligo, and corresponds to a region downstream of the restriction endonuclease cutting site. If the template DNA is digested, the bridge oligo will be amplified. An oligonucleotide probe that hybridizes to a sequence that contains the restriction endonuclease cutting site, which is contained within the bridge oligo, may be used to monitor the presence of the digested DNA. In a preferred embodiment, the restriction endonuclease recognizes a six-base cutting sequence. In a preferred embodiment, the restriction endonuclease is selected from EcoRI and HindIII.

Another embodiment of the chromosomal conformation methods disclosed herein provides a method for analyzing non-specific between-cell ligation (see, FIG. 3), the method including the steps of:

a) isolating cells from a biological sample;
b) incubating the cells with a cross-linking agent to cross-link proteins and DNA (e.g., chromatin or gDNA), thereby forming a cross-linked product;
c) lysing the cells;
d) digesting the DNA with a restriction enzyme;
e) filling-in and A-tailing the free ends of the digested DNA;
f) dividing the digested DNA into two separate aliquots resulting in a first aliquot and a second aliquot;
g) ligating a first half-adaptor to the digested DNA of the first aliquot thereby forming a first ligation product and a second half-adaptor to the digested DNA of the second aliquot thereby forming a second ligation product, wherein the first and second half-adaptors are different from each other and each half-adaptor contains a non-palindromic overhang on one end and a T overhang on the other end, wherein the non-palindromic overhang of the first half-adaptor is complementary to the non-palindromic overhang of the second half-adaptor;
h) combining the first and second ligation products;
i) ligating the first and second ligation products thereby forming a third ligation product; and
j) detecting and/or quantitating the third ligation product.

In one embodiment, the cross-linked product is optionally incubated with a cross-linking quencher. In another embodiment, the cross-linked product is removed from the cross-linking agent by washing or separating the quencher from the cross-linked product. In one embodiment, the cells are in suspension. In another embodiment, the cells are adherent. The cells may be intact, live, permeabilized or otherwise treated depending on the method of isolation.

In one embodiment, the ligation products are analyzed by the polymerase chain reaction (PCR). In preferred embodiments, the PCR can be endpoint PCR, real-time PCR, qPCR and dPCR, most preferably, the PCR is real-time PCR and qPCR. In one embodiment, the ligation products are analyzed by DNA sequencing methods including, but not limited to, fragment analysis, dideoxy sequencing (i.e., Sanger sequencing), Maxam-Gilbert chain termination sequencing, dye terminator sequencing, dye primer sequencing, pyrosequencing, next generation sequencing methods including, high-throughput sequencing, including massively parallel signature sequencing, SOLiD sequencing (e.g., sequencing by ligation), sequencing by hybridization, proton ion semiconductor sequencing, DNA nanoball sequencing, single molecule sequencing, and nanopore sequencing.

In one embodiment, the restriction enzyme recognizes a six-base cutting sequence. In a preferred embodiment, the restriction enzyme is selected from EcoRI and HindIII. In another embodiment, the restriction enzyme yields a blunt end. In another embodiment, the filling-in step uses Klenow (exo−) DNA polymerase.

In another embodiment, the third ligation product is purified before the analysis and/or detection step. In one embodiment, the purifying step comprises incubating the ligation product with magnetic beads for a period of time sufficient to allow the ligation product to bind to the magnetic beads. The bound ligation product is collected by centrifugation or by addition of a magnetic field. The bound ligation product is then eluted from the beads.

Figure 4:
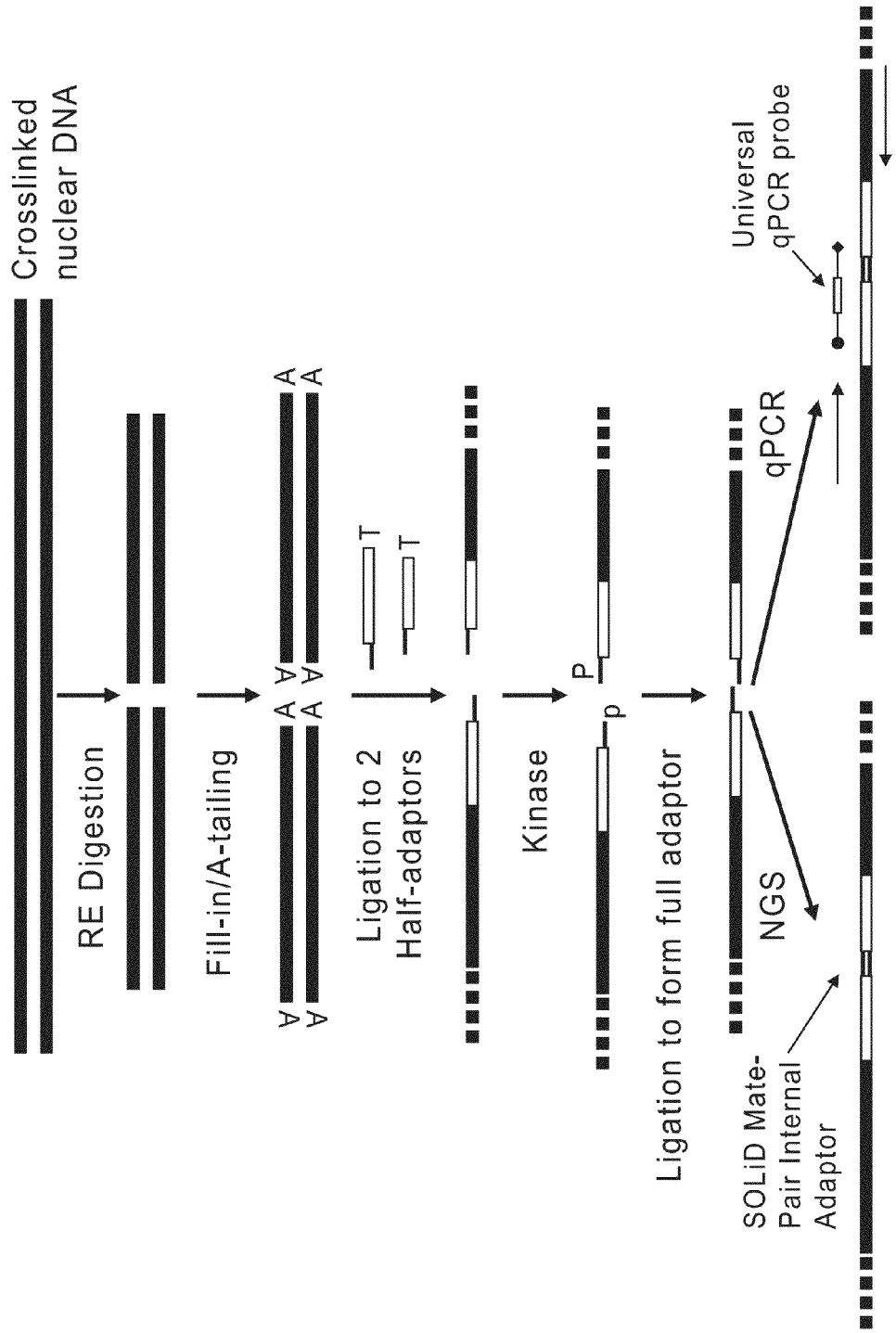
FIG. 4: A schematic representation of chromosomal conformation analysis and universal library preparation using linear half-adaptors with a T overhang, according to an embodiment of the present teachings.

Another embodiment provides a method for determining the three-dimensional arrangement of chromatin in a cell (see, FIG. 4), the method including the steps of:

a) isolating cells from a biological sample;
b) incubating the cells with a cross-linking agent to cross-link proteins and DNA (e.g., chromatin or gDNA), thereby forming a cross-linked product;
c) lysing the cells;
d) digesting the DNA with a restriction enzyme;
e) filling-in and A-tailing the free ends of the digested DNA;
f) ligating a first half-adaptor to the digested DNA thereby forming a first ligation product and a second half-adaptor to the digested DNA thereby forming a second ligation product, wherein the first and second half-adaptors are different from each other and each half-adaptor comprises a non-palindromic overhang on one end and a T overhang on the other end, wherein the non-palindromic overhang of the first adaptor is complementary to the non-palindromic overhang of the second adaptor;

g) phosphorylating the first and second ligation products;

h) ligating the first and second ligation products to form a third ligation product; and i) analyzing the third ligation product.

In one embodiment, the cross-linked product is optionally incubated with a cross-linking quencher. In another embodiment, the cross-linked product is removed from the cross-linking agent by washing or separating the quencher from the cross-linked product. In one embodiment, the cells are in suspension. In another embodiment, the cells are adherent. The cells may be intact, live, permeabilized or otherwise treated depending on the method of isolation.

In one embodiment, the ligation products are analyzed by the polymerase chain reaction (PCR). In preferred embodiments, the PCR can be endpoint PCR, real-time PCR, qPCR and dPCR, most preferably, the PCR is real-time PCR and qPCR. In one embodiment, the ligation products are analyzed by DNA sequencing methods including, but not limited to, fragment analysis, dideoxy sequencing (i.e., Sanger sequencing), Maxam-Gilbert chain termination sequencing, dye terminator sequencing, dye primer sequencing, pyrosequencing, next generation sequencing methods including, high-throughput sequencing, including massively parallel signature sequencing, SOLiD sequencing (e.g., sequencing by ligation), sequencing by hybridization, proton ion semiconductor sequencing, DNA nanoball sequencing, single molecule sequencing, and nanopore sequencing.

In one embodiment, the restriction enzyme recognizes a six-base cutting sequence. In a preferred embodiment, the restriction enzyme is selected from EcoRI and HindIII. In another embodiment, the restriction enzyme yields a blunt end. In another embodiment, the filling-in step uses Klenow (exo−) DNA polymerase.

In one embodiment, the first and second half-adaptors are linear. In another embodiment, the first and second half-adaptors have a stem-loop structure, herein referred to as "looped half-adaptors." In yet another embodiment, one of the first and second half-adaptors is a linear half-adaptor and the other is a looped half-adaptor. In yet a further embodiment, one of the first and second half-adaptors is conjugated to biotin.

In another embodiment, the third ligation product is purified before the analysis and/or detection step. In one embodiment, the purifying step comprises incubating the ligation product with magnetic beads for a period of time sufficient to allow the ligation product to bind to the magnetic beads. The bound ligation product is collected by centrifugation or by addition of a magnetic field. The bound ligation product is then eluted from the beads.

Figure 5:
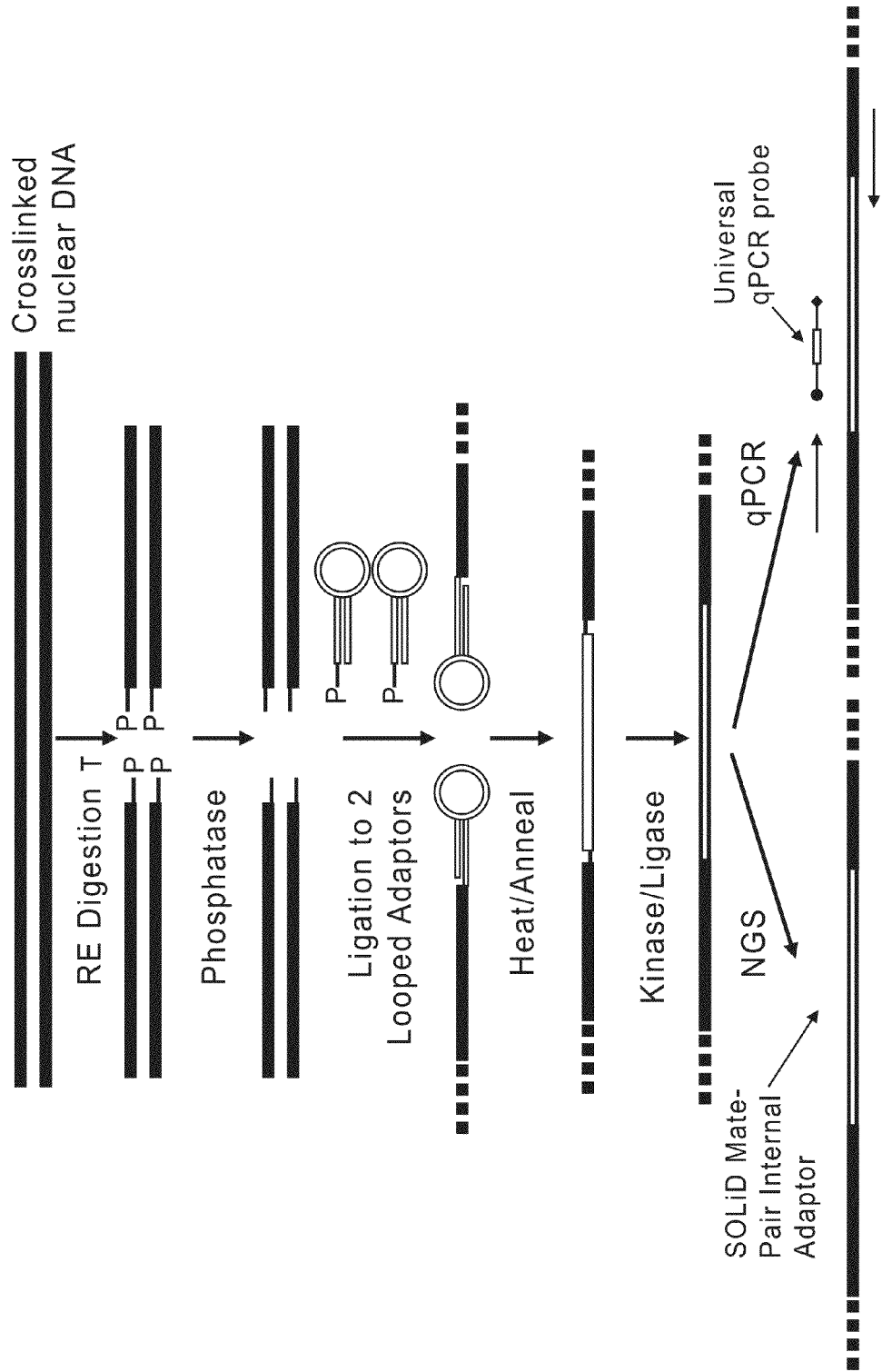
FIG. 5: A schematic representation of chromosomal conformation analysis and universal library preparation using 5'-phosphate looped adaptors with cohesive ends, according to an embodiment of the present teachings.

Yet another embodiment (see, FIG. 5) provides a chromosome conformation method including the steps of:

a) isolating cells from a biological sample;

b) incubating the cells with a cross-linking agent to cross-link proteins and DNA (e.g., chromatin or gDNA), thereby forming a cross-linked product;

c) lysing the cells;

d) digesting the DNA with a restriction enzyme;

e) incubating the digested DNA with a phosphatase;

f) ligating a first looped half-adaptor to the digested DNA thereby forming a first ligation product and a second looped half-adaptor to the digested DNA thereby forming a second ligation product, wherein the first and second looped half-adaptors are different from each other and each looped half-adaptor comprises a stem-loop structure, wherein the 5' end of the stem comprises a cohesive (or non-palindromic) overhang that terminates in a 5'-phosphate group;

g) heating the first and second ligation products thereby allowing the cohesive ends of each looped half-adaptors to anneal to each other;

h) phosphorylating the free ends of each of the looped half-adaptors;

i) ligating the looped half-adaptors to the DNA fragment thereby forming a third ligation product; and i) analyzing the third ligation product.

In one embodiment, the cross-linked product is optionally incubated with a cross-linking quencher. In another embodiment, the cross-linked product is removed from the cross-linking agent by washing or separating the quencher from the cross-linked product. In one embodiment, the cells are in suspension. In another embodiment, the cells are adherent. The cells may be intact, live, permeabilized or otherwise treated depending on the method of isolation.

In one embodiment, the ligation products are analyzed by the polymerase chain reaction (PCR). In preferred embodiments, the PCR can be endpoint PCR, real-time PCR, qPCR and dPCR, most preferably, the PCR is real-time PCR and qPCR. In one embodiment, the ligation products are analyzed by DNA sequencing methods including, but not limited to, fragment analysis, dideoxy sequencing (i.e., Sanger sequencing), Maxam-Gilbert chain termination sequencing, dye terminator sequencing, dye primer sequencing, pyrosequencing, next generation sequencing methods including, high-throughput sequencing, including massively parallel signature sequencing, SOLiD sequencing (e.g., sequencing by ligation), sequencing by hybridization, proton ion semiconductor sequencing, DNA nanoball sequencing, single molecule sequencing, and nanopore sequencing.

In one embodiment, the restriction enzyme recognizes a six-base cutting sequence. In a preferred embodiment, the restriction enzyme is selected from EcoRI and HindIII. In another embodiment, the restriction enzyme yields a blunt end. In another embodiment, the filling-in step uses Klenow (exo−) DNA polymerase. In one embodiment, the heating and annealing step is replaced by a nick translation step.

In one embodiment, the first and second half-adaptors are linear. In another embodiment, the first and second half-adaptors are looped half-adaptors. In yet another embodiment, one of the first and second half-adaptors is a linear half-adaptor and the other is a looped half-adaptor. In yet a further embodiment, one of the first and second half-adaptors is conjugated to biotin.

In another embodiment, the third ligation product is purified before the analysis and/or detection step. In one embodiment, the purifying step comprises incubating the ligation product with magnetic beads for a period of time sufficient to allow the ligation product to bind to the magnetic beads. The bound ligation product is collected by centrifugation or by the addition of a magnetic field. The bound ligation product is then eluted from the beads.

Figure 6:
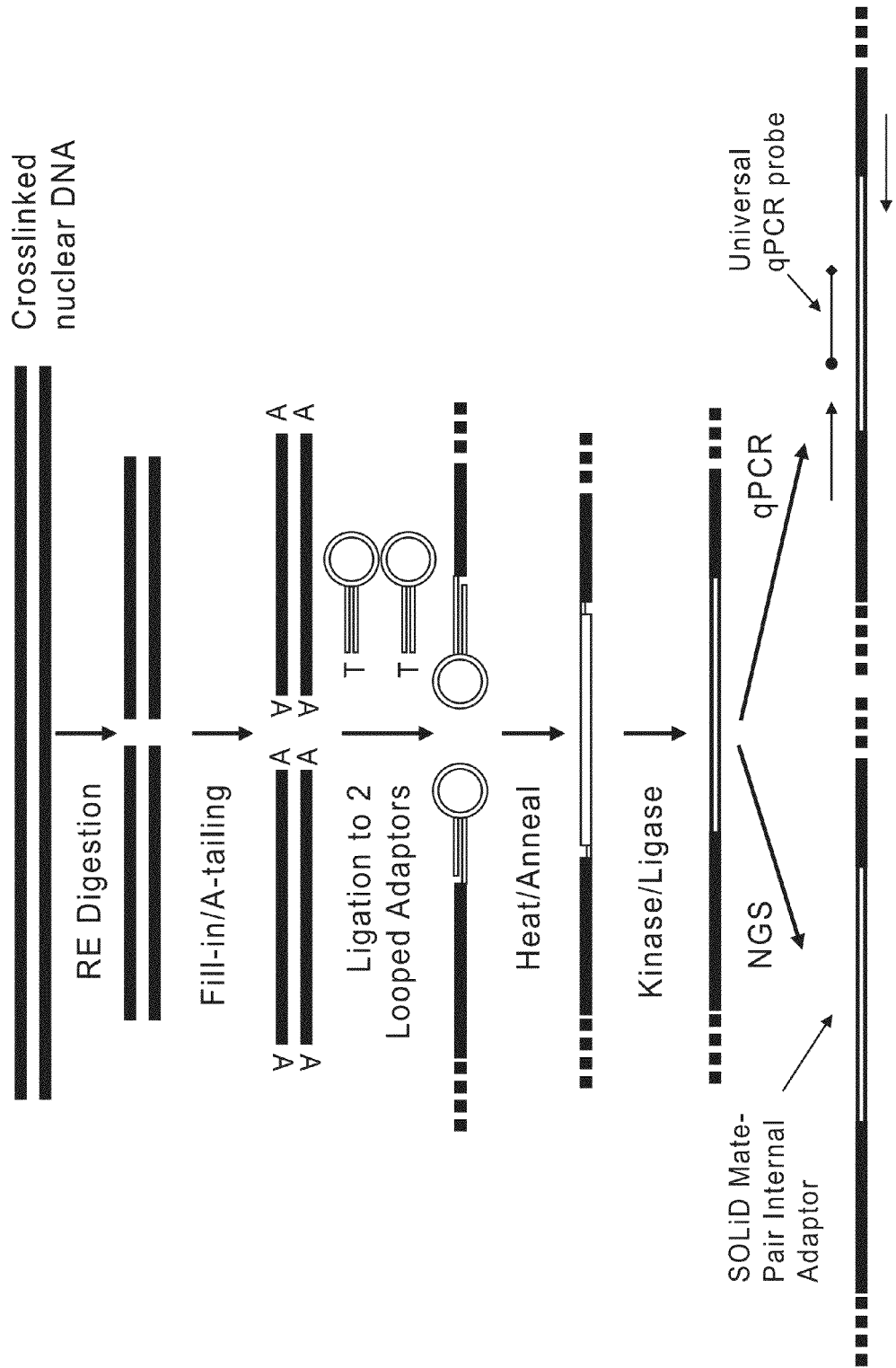
FIG. 6: A schematic representation of chromosomal conformation analysis and universal library preparation using 5'-OH looped adaptors with a T overhang, according to an embodiment of the present teachings.

Yet a further embodiment (see, FIG. 6) provides a chromosomal conformation method including the steps of:

a) isolating cells from a biological sample;

b) incubating the cells with a cross-linking agent to cross-link proteins and DNA (e.g., chromatin or gDNA), thereby forming a cross-linked product;

c) lysing the cells;

d) digesting the DNA with a restriction enzyme;

e) filling-in and A-tailing the free ends of the digested DNA;

f) ligating a first looped half-adaptor to the digested DNA thereby forming a first ligation product and a second looped half-adaptor to the digested DNA thereby forming a second ligation product, wherein the first and second looped half-adaptors are different from each other and each half-adaptor comprises a stem-loop structure, wherein the 5' end of the stem comprises a 5'-OH group and the 3' end of the stem comprises a 3' T overhang;

g) heating the first and second ligation products thereby allowing each of the looped half-adaptors to anneal to each other;

h) phosphorylating the free ends of each of the looped half-adaptors;

i) ligating each of the half-adaptors to the DNA fragment thereby forming a third ligation product; and i) analyzing the third ligation product.

In one embodiment, the cross-linked product is optionally incubated with a cross-linking quencher. In another embodiment, the cross-linked product is removed from the cross-linking agent by washing or separating the quencher from the cross-linked product. In one embodiment, the cells are in suspension. In another embodiment, the cells are adherent. The cells may be intact, live, permeabilized or otherwise treated depending on the method of isolation.

In one embodiment, the ligation products are analyzed by the polymerase chain reaction (PCR). In preferred embodiments, the PCR can be endpoint PCR, real-time PCR, qPCR and dPCR, most preferably, the PCR is real-time PCR and qPCR. In one embodiment, the ligation products are analyzed by DNA sequencing methods including, but not limited to, fragment analysis, dideoxy sequencing (i.e., Sanger sequencing), Maxam-Gilbert chain termination sequencing, dye terminator sequencing, dye primer sequencing, pyrosequencing, next generation sequencing methods including, high-throughput sequencing, including massively parallel signature sequencing, SOLiD sequencing (e.g., sequencing by ligation), sequencing by hybridization, proton ion semiconductor sequencing, DNA nanoball sequencing, single molecule sequencing, and nanopore sequencing.

In one embodiment, the restriction enzyme recognizes a six-base cutting sequence. In a preferred embodiment, the restriction enzyme is selected from EcoRI and HindIII. In another embodiment, the restriction enzyme yields a blunt end. In another embodiment, the filling-in step uses Klenow (exo–) DNA polymerase. In one embodiment, the heating and annealing step is replaced by a nick translation step. In one embodiment, the filling-in step is replaced by a phosphatase step. In another embodiment the phosphorylation and ligation steps are replaced by a nick translation step.

In one embodiment, the first and second half-adaptors are linear. In another embodiment, the first and second half-adaptors are looped half-adaptors. In yet another embodiment, one of the first and second half-adaptors is a linear half-adaptor and the other is a looped half-adaptor. In yet a further embodiment, one of the first and second half-adaptors is conjugated to biotin.

In another embodiment, the third ligation product is purified before the analysis and/or detection step. In one embodiment, the purifying step comprises incubating the ligation product with magnetic beads for a period of time sufficient to allow the ligation product to bind to the magnetic beads. The bound ligation product is collected by centrifugation or by the addition of a magnetic field. The bound ligation product is then eluted from the beads.

Figure 7A:
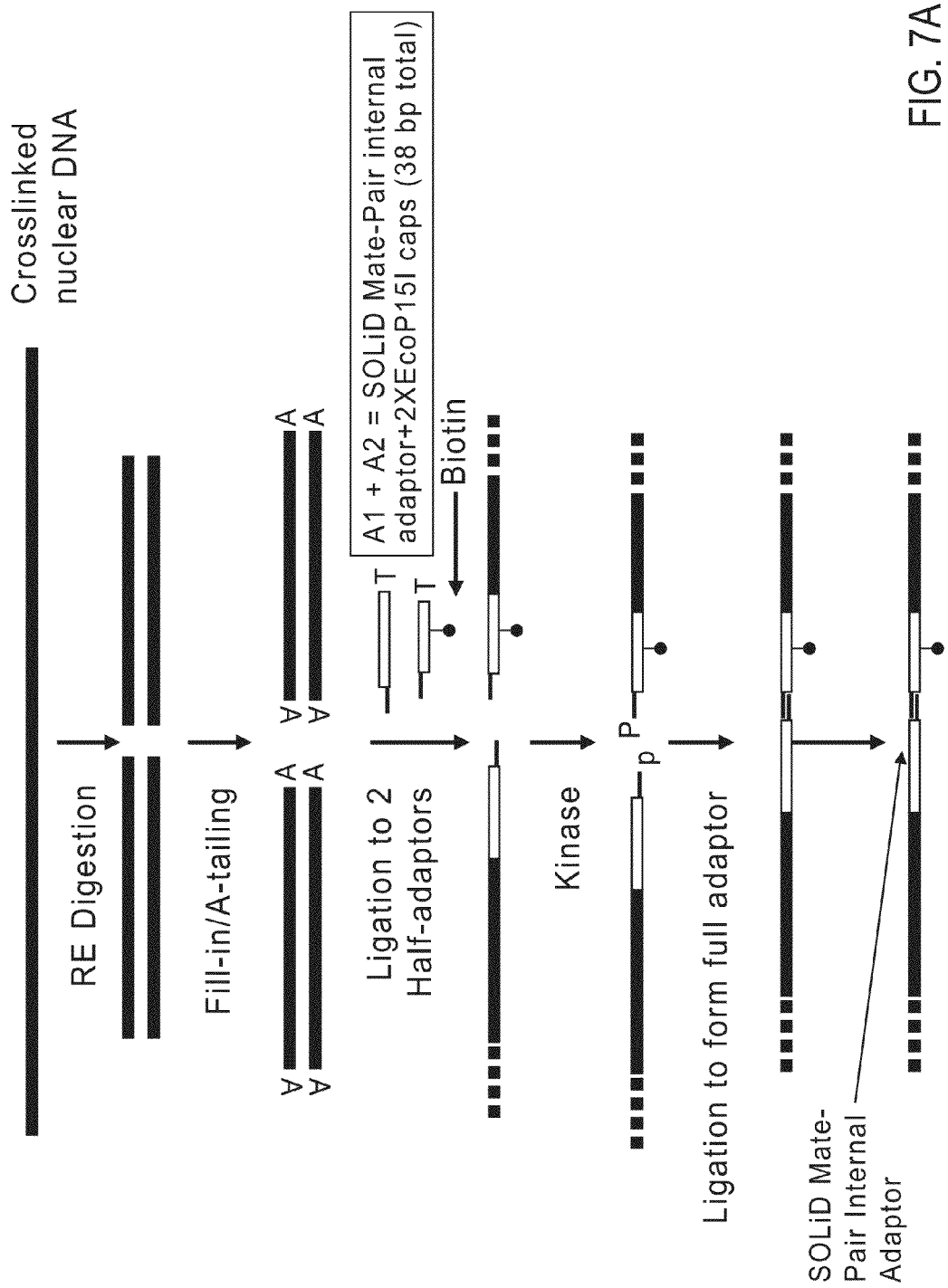
FIGS. 7A and 7B: A schematic representation of universal 3C library construction to be used in the methods disclosed herein, according to an embodiment of the present teachings.
Figure 7B:
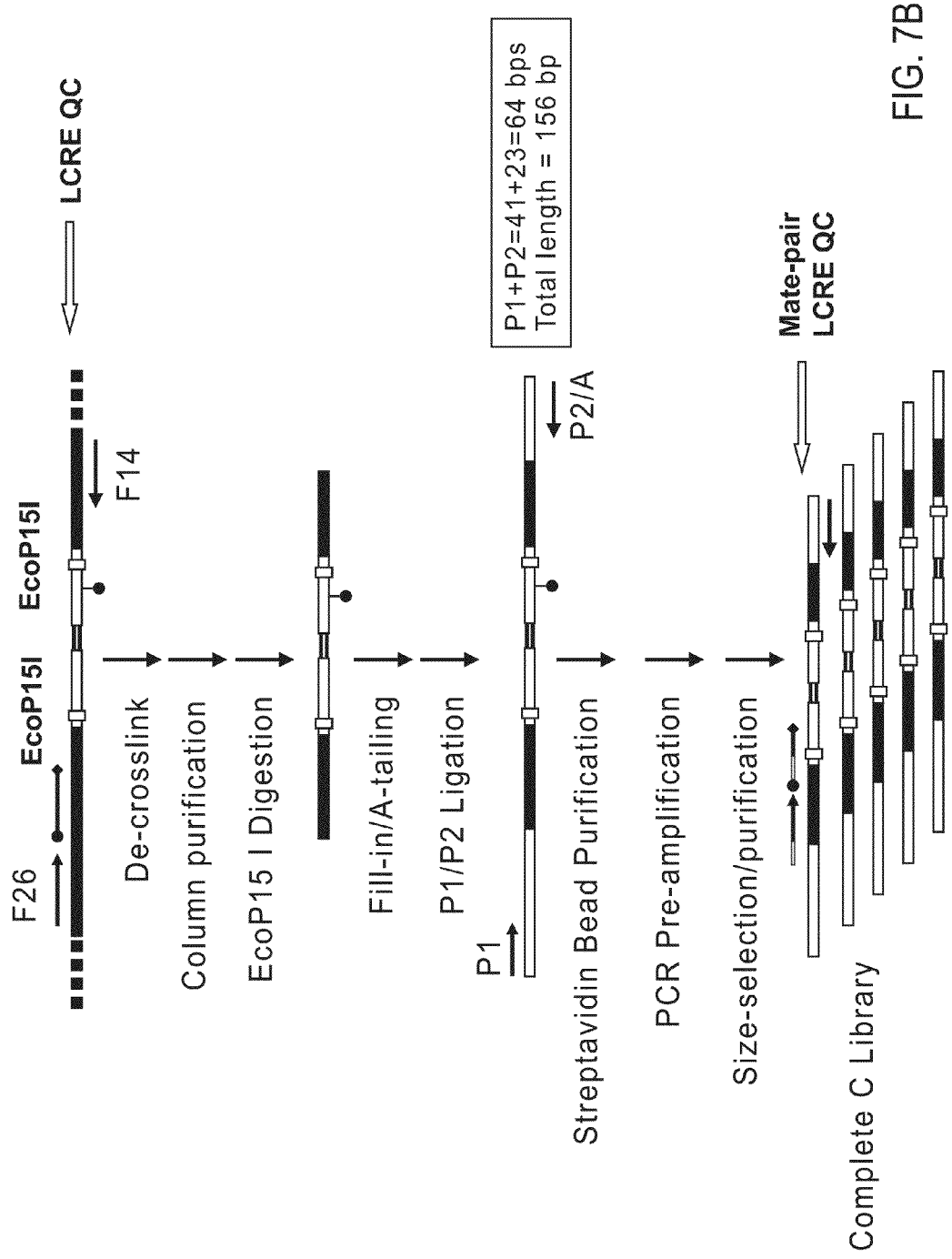

Another embodiment provides a method of creating a library for chromosome conformation analysis (see, FIG. 7), the method including the steps of:

a) isolating cells from a biological sample;

b) incubating the cells with a cross-linking agent to cross-link proteins and DNA (e.g., chromatin or gDNA), thereby forming a cross-linked product;

c) lysing the cells;

d) digesting the DNA with a restriction endonuclease;

e) filling-in and A-tailing the free ends of the digested DNA;

f) optionally methylating the digested DNA;

g) ligating a first half-adaptor to the digested DNA thereby forming a first ligation product and a second half-adaptor to the digested DNA thereby forming a second ligation product, wherein the first and second half-adaptors are different from each other and each half-adaptor comprises a non-palindromic overhang on one end and a T overhang on the other end, wherein the non-palindromic overhang of the first adaptor is complementary to the non-palindromic overhang of the second adaptor, further wherein the first or the second half-adaptor is biotinylated;

h) phosphorylating the ligated half-adaptors;

i) nick ligating the first and second ligation products, thereby forming a third ligation product;

j) reversing the cross-linking;

k) purifying the third ligation product;

l) digesting the third ligation product with a restriction endonuclease;

m) filling-in and A-tailing the free ends of the digested DNA;

n) isolating the digested DNA using streptavidin beads;

o) ligating the digested DNA with sequencing primers;

p) analyzing the DNA.

In one embodiment, the cross-linked product is optionally incubated with a cross-linking quencher. In another embodiment, the cross-linked product is removed from the cross-linking agent by washing or separating the quencher from the cross-linked product. In one embodiment, the cells are in suspension. In another embodiment, the cells are adherent. The cells may be intact, live, permeabilized or otherwise treated depending on the method of isolation.

In one embodiment, the ligation products are analyzed by the polymerase chain reaction (PCR). In preferred embodiments, the PCR can be endpoint PCR, real-time PCR, qPCR and dPCR, most preferably, the PCR is real-time PCR and qPCR. In one embodiment, the ligation products are analyzed by DNA sequencing methods including, but not limited to, fragment analysis, dideoxy sequencing (i.e., Sanger sequencing), Maxam-Gilbert chain termination sequencing, dye terminator sequencing, dye primer sequencing, pyrosequencing, next generation sequencing methods including, high-throughput sequencing, including massively parallel signature sequencing, SOLiD sequencing (e.g., sequencing by ligation), sequencing by hybridization, proton ion semiconductor sequencing, DNA nanoball sequencing, single molecule sequencing, and nanopore sequencing.

In one embodiment, the restriction enzyme is selected from a Type IIS or Type III restriction endonuclease. In a preferred embodiment, the restriction enzyme is selected from MmeI and EcoP15I. In another embodiment, the restriction enzyme yields a blunt end. In another embodiment, the filling-in step uses Klenow (exo–) DNA polymerase.

In one embodiment, the first and second half-adaptors are linear. In another embodiment, the first and second half-adaptors are looped half-adaptors. In yet another embodiment, one of the first and second half-adaptors is a linear half-adaptor and the other is a looped half-adaptor.

In another embodiment, the third ligation product is purified before the analysis and/or detection step. In one embodiment, the purifying step comprises incubating the ligation product with magnetic beads for a period of time sufficient to allow the ligation product to bind to the magnetic beads. The bound ligation product is collected by centrifugation or by the addition of a magnetic field. The bound ligation product is then eluted from the beads.

A further embodiment provides kits for analysis of chromosome conformation, the kits comprising in one or more separate containers: a cross-linking agent, a lysing solution, a DNA ligase, and a protease. In another embodiment, the kit further provides a cross-linking quencher. In yet another embodiment, the kit further provides magnetic beads, a DNA binding solution, a DNA washing solution, and a DNA elution solution. In yet another embodiment, the kit further provides a protease inhibitor cocktail, a restriction enzyme stop solution, and a neutralization solution. In another embodiment, the kit comprises control assays, wherein the control assays include Assay 1 and Assay 2, and a first and second half-adaptor. In a further embodiment, the kits disclosed herein may further comprise one or more of the following: a buffer, such as phosphate buffer saline, and RNase A. In a further embodiment, the kits disclosed herein may further comprise instructions for carrying out the methods disclosed herein.

A further embodiment provides for the use of any of the chromosomal conformation analysis methods disclosed herein in the diagnosis of diseases, for example, cancer, including but not limited to breast cancer, prostate cancer, lung cancer, skin cancer, cancers of the reproductive tract, brain cancer, liver cancer, pancreatic cancer, stomach cancer, blood cancers (e.g., leukemia and lymphoma), sarcomas, melanomas, and the like; cardiovascular diseases; autoimmune diseases and disorders; and metabolic diseases and disorders. Another embodiment provides for the use of any of the chromosomal conformation analysis methods disclosed herein in the diagnosis or determination of responsiveness to drugs and medical treatment.

Other embodiments and illustrative aspects, features and advantages of the present disclosure will become apparent from the following detailed description. It should be understood that the detailed description and the specific examples, while indicating preferred embodiments, are given by way of illustration only, since various changes and modifications within the spirit and scope of the present disclosure will become apparent to those skilled in the art from this detailed description.

DETAILED DESCRIPTION

Provided herein are methods, compositions and kits that are useful for analyzing the physical interactions between various genomic elements that affect gene regulation, DNA replication and genome organization. Through structures such as loops and bridges, chromatin fibers make multiple physical contacts with genetic elements that can be tens to hundreds of kilobases apart or more. To study these contacts, specifically to analyze the frequency of interaction and proximity between any two genomic loci, chromosome conformation capture methods provided herein may be used. The chromosome conformation capture methods provided herein convert physical interactions between genomic loci into unique ligation products and the concentration of a individual ligation product is correlated to the frequency of looping between the two genomic regions. The abundance of the ligation products can be quantified by methods such as the polymerase chain reaction (PCR), including endpoint PCR, real-time PCR, quantitative PCR (qPCR) and digital PCR (dPCR), and sequencing methods, including, but not limited to, fragment analysis, dideoxy sequencing (i.e., Sanger sequencing), Maxam-Gilbert chain termination sequencing, dye terminator sequencing, dye primer sequencing, pyrosequencing, next generation sequencing methods including, high-throughput sequencing, including massively parallel signature sequencing, SOLiD sequencing (e.g., sequencing by ligation), sequencing by hybridization, proton ion semiconductor sequencing, DNA nanoball sequencing, single molecule sequencing, and nanopore sequencing.

Eukaryotic genomes are organized non-randomly in the nucleus. The arrangement of genomic loci not only depends on cell stage and cell lineage, but also plays an important role in gene regulation. The studies of genome organization and DNA interaction have relied on the Chromosome Conformation Capture (3C) method (Dekker et al, supra); however, its applications are hindered by many challenges including: (1) non-optimized and variable results; (2) reagent quality is not controlled; (3) large reaction volumes; (4) the lack of process controls; (5) the lack of a quantitative readout; and (6) the process itself takes at least five days. The protocols and reagents for key steps of the process, the methods, compositions and kits provided herein improve the 3C process and overcome the above-mentioned obstacles. Furthermore, the methods, compositions and kits disclosed herein result in an increase in library yield and a several fold increase in ligation efficiency. The present teachings also accommodate a wide range of cell input in a much smaller reaction volume. The present teachings also provide validated TaqMan® control assays that allow for the quantitative measurement and control of digestion and ligation efficiencies. The methods, compositions and kits provided herein also are useful for higher-order genome analysis.

In addition, the 3C analysis methods currently available are not capable of high throughput analysis and therefore can only analyze a limited number of loci. Other methods for three-dimensional analysis of chromatin structure are limited in their ability to capture and identify long-range interactions and are biased towards proximal genomic interactions.

The methods, compositions and kits disclosed herein overcome these and other limitations by connecting DNA fragments cross-linked through protein complexes with short non-palindromic DNA half-adaptors. The resulting library is estimated to include millions of DNA molecules in which the ligation of two half-adaptors connects two DNA fragments. The resulting full adaptor (ligation of two complementary half-adaptors) may then serve as a primer template to analyze the library by DNA sequencing to identify potentially interacting genomic loci joined at each end of the full adaptor. Alternatively, the library may be sequenced from both ends to identify the interacting loci. In addition, the DNA fragments linked by an adaptor molecule may be analyzed by the polymerase chain reaction (PCR). The methods, compositions and kits of the present teachings may be used to capture the interaction of all or a significant fraction of genomic elements that are proximal and long-range and cross-linked in vivo. This approach allows for the detection of genomic-wide binary contact in a high-throughput and unbiased manner.

Aspects of the present teachings may be further understood in light of the following detailed description and examples, which should not be construed as limiting the scope of the present teachings in any way. The section headings used herein are for organizational purposes only and are not to be construed as limiting the described subject matter in any way. All literature and similar materials cited in this specification, including, but not limited to, patents, patent applications, articles, books, treatises and Internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc. discussed in the present teaching, such that slight and insubstantial deviations are within the scope of the present teachings herein. In this application, the use of the singular includes the plural unless specifically stated otherwise. For example, "a primer" means that more than one primer can, but need not, be present; for example, but without limitation, one or more copies of a particular primer species, as well as one or more versions of a particular primer type, for example but not limited to, a multiplicity of different forward primers. Also, the use of "comprise," "comprises," "comprising," "contain," "contains," "containing," "include," "includes," and "including" are not intended to be limiting. It is to be understood that both the foregoing general description and the following detailed description are exemplary and explanatory only and are not restrictive of the invention of the present teachings.

A comparison of the methods disclosed herein to the 3C method of Dekker et al., (supra) reveals a shorter, more streamlined process resulting in increased efficiency. The 3C method of Dekker et al. is a five-day process whereas the methods disclosed herein require only two days to obtain a result (see, Table 1 below).

e) ligating the digested DNA by incubating with a ligating agent thereby creating a ligation product;

f) reversing the cross-linking;

g) purifying the ligated DNA; and h) analyzing the ligation product.

In one embodiment, the cross-linked product is optionally incubated with a cross-linking quencher. In another embodiment, the cross-linked product is removed from the cross-linking agent by washing or separating the quencher from the cross-linked product. In one embodiment, the cells are in suspension. In another embodiment, the cells are adherent. The cells may be intact, live, permeabilized or otherwise treated depending on the method of isolation.

In one embodiment, the ligation products are analyzed by the polymerase chain reaction (PCR). In preferred embodiments, the PCR can be endpoint PCR, real-time PCR, qPCR and dPCR, most preferably, the PCR is real-time PCR and qPCR. In one embodiment, the ligation products are analyzed by DNA sequencing methods including, but not limited to, fragment analysis, dideoxy sequencing (i.e., Sanger sequencing), Maxam-Gilbert chain termination sequencing, dye terminator sequencing, dye primer sequencing, pyrosequencing, next generation sequencing methods including, high-throughput sequencing, including massively parallel

TABLE 1

Comparison of Chromosomal Conformation Analysis Methods

| Protocol | Day 1 | Day 2 | Day 3 | Day 4 | Day 5 |
|---|---|---|---|---|---|
| 3C (Dekker) | Cross-linking Cell lysis Homogenization Split into 20 tubes Wash in restriction buffer 3× Restriction enzyme digestion overnight (37° C.) | Restriction enzyme inactivation Change to 8-15 ml tubes Ligation (16° C., 2 h) Proteinase K (65° C., 2 h, then overnight) Phenol plus buffer overnight | Pool & transfer to 3-50 ml tubes Phenol extraction Phenol: Chloroform 1:1 extraction Pool & transfer to 250 ml bottles Ethanol precipitate (−80° C. overnight) | Spin bottles at high speed, 20 min (4° C.) Resuspend in 500 µl Tris/EDTA buffer Phenol extraction Phenol: Chloroform 1:1 extraction Ethanol precipitate Wash in 70% ethanol, 7× | Template input titration PCR setup PCR Separate on 1.5% agarose gel Gel imaging & band quantitation |
| Embodiments of the methods described herein | Cross-linking Cell lysis Wash in restriction buffer 3× Restriction enzyme digestion (37° C., 2 h) Restriction enzyme inactivation Ligation (16° C., 60 min) Proteinase K (65° C., overnight) | Purification with beads Template quality check | N/A | N/A | N/A |

One embodiment provides a method of chromosome conformation analysis (see, FIG. 1), the method including the steps of:

a) isolating cells from a biological sample;

b) incubating the cells with a cross-linking agent to cross-link proteins and DNA (e.g., chromatin or gDNA), thereby forming a cross-linked product;

c) lysing the cells;

d) digesting the DNA with a restriction endonuclease;

signature sequencing, SOLiD sequencing (e.g., sequencing by ligation), sequencing by hybridization, proton ion semiconductor sequencing, DNA nanoball sequencing, single molecule sequencing, and nanopore sequencing.

In one embodiment of the methods disclosed herein, cross-linking the DNA and the proteins interacting with the DNA is performed by using a cross-linking reagent, such as an agent that can reversibly cross-link primary amino groups in proteins with other nearby nitrogen atoms in other proteins or DNA. Such cross-linking agents include, but are not limited to, formaldehyde, paraformaldehyde, formalin, other similar aldehyde compounds, and other bi-functional cross-linking reagents that can covalently cross-link protein-protein and protein-DNA molecules together. The cross-linking reaction may be quenched, or inhibited, by the addition of an amine-containing quenching reagent. Exemplary amine-containing quenching reagents include, any compound that contains an available amine group including, but not limited to, methylamine, ethanolamine, Tris, dimethylamine, methylethanolamine, trimethylamine, aziridine, piperidiene, amiline, glycine, asparagine, and glutamine.

In the methods disclosed herein, the cross-linked DNA may be lysed in a detergent-containing solution. The detergents that may be used in embodiments of the methods disclosed herein include, but are not limited to, anionic detergents, cationic detergents, non-ionic detergents and zwitterionic detergents, or combinations thereof. Such combinations include: one or more cationic detergents with one or more anionic detergents; one or more cationic detergents with one or more non-ionic detergents; one or more cationic detergents with one or more zwitterionic detergents; one or more anionic detergents with one or more non-ionic detergents; one or more anionic detergents with one or more zwitterionic detergents; and one or more non-ionic detergents with one or more zwitterionic detergents. In a preferred embodiment, one or more anionic detergents are combined with one or more non-ionic detergents. Non-limiting examples of anionic detergents include alkyl sulfates (e.g., sodium dodecylsulfate), alkyl sulfonates (e.g., octane sulfonic acid), bile salts, docusate sodium salt, and N-laurylsarcosine. Non-limiting examples of cationic detergents include bezalkonium chloride, cetyl pyridium chloride, dodecyltrimethylammonium chloride, Girard's reagent, and Hyamine® 1622. Non-limiting examples of non-ionic detergents include Tween®-20, Tween®-80, Triton® X-100, Triton® X-114, PEGylates, IGEPAL, Nonidet™-P40, Pluronic® F-68, Poloxamer 407, saponin and Tergitol®. Non-limiting examples of zwitterionic detergents include CHAPS, L-α-lysophosphatidyl choline, DDMAB, and miltefosine.

After the lysis step, the cross-linked DNA may be digested using restriction endonucleases. As used herein, the terms "restriction endonuclease" and "restriction enzyme" are equivalent and are used interchangeably. Any type of restriction endonuclease may be used to digest the cross-linked DNA. Preferably, the restriction endonuclease has a six base recognition sequence, but it may have an eight base recognition sequence, a seven base recognition sequence, a five base recognition sequence or a four base recognition sequence. Such restriction endonucleases that may be used in the methods described herein include, but are not limited to, Alu I, Apo I, Ase I, BamH I, BfuC I, Bgl II, BsaJ I, BstKT I, BstY I, Btg I, Cla I, CviKI-1, Dpn I, Dpn II, Eco47 III, EcoR I, EcoR V, EcoP15I, Fai I, Hae III, Hind III, Hpa II, HpyCH4 III, Kpn I, Mbo I, Mnl I, Mse I, Msp I, Nco I, Nde I, Nhe I, Not I, Pst I, Rsa I, Sac I, Sac II, Sal I, Sau3A I, Sfi I, Sma I, Taq I, Tsp509 I, Xba I, Xho I and Xma I. In a preferred embodiment, the restriction enzyme is EcoRI and HindIII. The restriction endonuclease digestion may be terminated by the addition of a restriction stop solution and a neutralizing solution. In another embodiment, the restriction endonuclease digestion may be terminated by heat treatment.

After the digestion step, the cross-linked DNA fragments may be ligated using a ligase that is specific for double-stranded DNA. Such ligases include, but are not limited to, T4 DNA ligase, Tfi DNA ligase, DNA ligase I, DNA ligase II, DNA ligase III, DNA ligase IV, and small footprint DNA ligases.

Once the ligation step is completed, the cross-linking is reversed using for example, a protease such as, but not limited to, serine proteases, such as Proteinase K, chymotrypsin, trypsin, elastin, subtilisin; threonine proteases; cysteine proteases, such as caspase, cathepsins, papain; aspartate proteases, such as rennin, chymosin, cathepsin D, pepsin; metalloproteases, such as aminopeptidase, dipeptidylpeptidase, angiotensin converting enzyme, carboxypeptidase; and glutamic acid peptidases. In preferred embodiments, the protease is Proteinase K. Following reversal of cross-linking, the ligated DNA is purified.

In one embodiment, the purifying step includes purifying the ligation product using column purification. In another embodiment, the purifying step includes incubating the ligation product with magnetic beads for a period of time sufficient to allow the ligation product to bind to the magnetic beads. The bound ligation product may be collected either by centrifugation or addition of a magnetic field. The beads are subsequently washed and the ligated DNA is eluted.

The use of magnetic beads replaces the phenol/chloroform DNA precipitation steps and advantageously results in a higher yield of cross-linked product due to the omission of the multiple extraction and dilution steps. In addition, incubation with the magnetic beads replaces the need for the lengthy phenol:chloroform extraction and results in avoiding the use of toxic chemicals.

Another embodiment provides a chromosome conformation analysis method that includes a control assay that monitors the undigested template DNA, herein denoted "Assay 1." (see, FIG. 2) Assay 1 uses oligonucleotide primers that specifically hybridize to regions either upstream (herein denoted "forward primer") or downstream (herein denoted "reverse primer") of the restriction endonuclease cutting site in the template DNA. If the restriction site is not digested, the sequence will be amplified. An oligonucleotide probe that hybridizes to a sequence upstream of the restriction site may be used to monitor the presence of the undigested template DNA. In a preferred embodiment, the restriction endonuclease recognizes a six-base cutting sequence. In a more preferred embodiment, the restriction endonuclease is selected from EcoRI and HindIII.

Yet another embodiment provides a chromosome conformation analysis method that includes a control assay that monitors the digested template DNA, herein denoted "Assay 2." (see, FIG. 2) Assay 2 uses oligonucleotides, herein referred to as "bridge oligos" that have a blocked 3' end, a template binding region that hybridizes to the 3' end of the template DNA, and a 5' region that hybridizes to the primer and probe sequences. In the first cycle of PCR, the bridge oligo anneals to the template DNA via the template DNA binding region and the bridge oligo sequence is amplified resulting in a first amplification product. In the second cycle of PCR, first amplification product is incubated with a forward primer that hybridizes to the 5' end of the bridge oligo that contains the primer binding site which is upstream of the restriction endonuclease cutting site, and a reverse primer that hybridizes to the template DNA which contains the complement of the bridge oligo, and corresponds to a region downstream of the restriction endonuclease cutting site, to amplify the bridge oligo if the template DNA is digested. An oligonucleotide probe that hybridizes to a sequence that contains the restriction endonuclease cutting site, which is contained within the bridge oligo, may be used to monitor the presence of the digested DNA. In a preferred embodiment, the restriction endonuclease recognizes a six-base cutting sequence. In a preferred embodiment, the restriction endonuclease is selected from EcoRI and HindIII.

Another embodiment of the chromosomal conformation methods disclosed herein provides a method for analyzing non-specific between-cell ligation (see, FIG. 3), the method including the steps of:

a) isolating cells from a biological sample;

b) incubating the cells with a cross-linking agent to cross-link proteins and DNA (e.g., chromatin or gDNA), thereby forming a cross-linked product;

c) lysing the cells;

d) digesting the DNA with a restriction enzyme;

e) filling-in and A-tailing the free ends of the digested DNA;

f) dividing the digested DNA into two separate aliquots resulting in a first aliquot and a second aliquot;

g) ligating a first half-adaptor to the digested DNA of the first aliquot thereby forming a first ligation product and a second half-adaptor to the digested DNA of the second aliquot thereby forming a second ligation product, wherein the first and second half-adaptors are different from each other and each half-adaptor contains a non-palindromic overhang on one end and a T overhang on the other end, wherein the non-palindromic overhang of the first half-adaptor is complementary to the non-palindromic overhang of the second half-adaptor;

h) combining the first and second ligation products;

i) ligating the first and second ligation products thereby forming a third ligation product; and j) detecting and/or quantitating the third ligation product.

In one embodiment, the cross-linked product is optionally incubated with a cross-linking quencher. In another embodiment, the cross-linked product is removed from the cross-linking agent by washing or separating the quencher from the cross-linked product. In one embodiment, the cells are in suspension. In another embodiment, the cells are adherent. The cells may be intact, live, permeabilized or otherwise treated depending on the method of isolation.

In one embodiment, the ligation products are analyzed by the polymerase chain reaction (PCR). In preferred embodiments, the PCR can be endpoint PCR, real-time PCR, qPCR and dPCR, most preferably, the PCR is real-time PCR and qPCR. In one embodiment, the ligation products are analyzed by DNA sequencing methods including, but not limited to, fragment analysis, dideoxy sequencing (i.e., Sanger sequencing), Maxam-Gilbert chain termination sequencing, dye terminator sequencing, dye primer sequencing, pyrosequencing, next generation sequencing methods including, high-throughput sequencing, including massively parallel signature sequencing, SOLiD sequencing (e.g., sequencing by ligation), sequencing by hybridization, proton ion semiconductor sequencing, DNA nanoball sequencing, single molecule sequencing, and nanopore sequencing.

In one embodiment, the restriction enzyme recognizes a six-base cutting sequence. In a preferred embodiment, the restriction enzyme is selected from EcoRI and HindIII. In another embodiment, the restriction enzyme yields a blunt end. In another embodiment, the filling-in step uses Klenow (exo–) DNA polymerase.

In another embodiment, the third ligation product is purified before the analysis and/or detection step. In one embodiment, the purifying step comprises incubating the ligation product with magnetic beads for a period of time sufficient to allow the ligation product to bind to the magnetic beads. The bound ligation product is then eluted from the beads.

Figure 3:
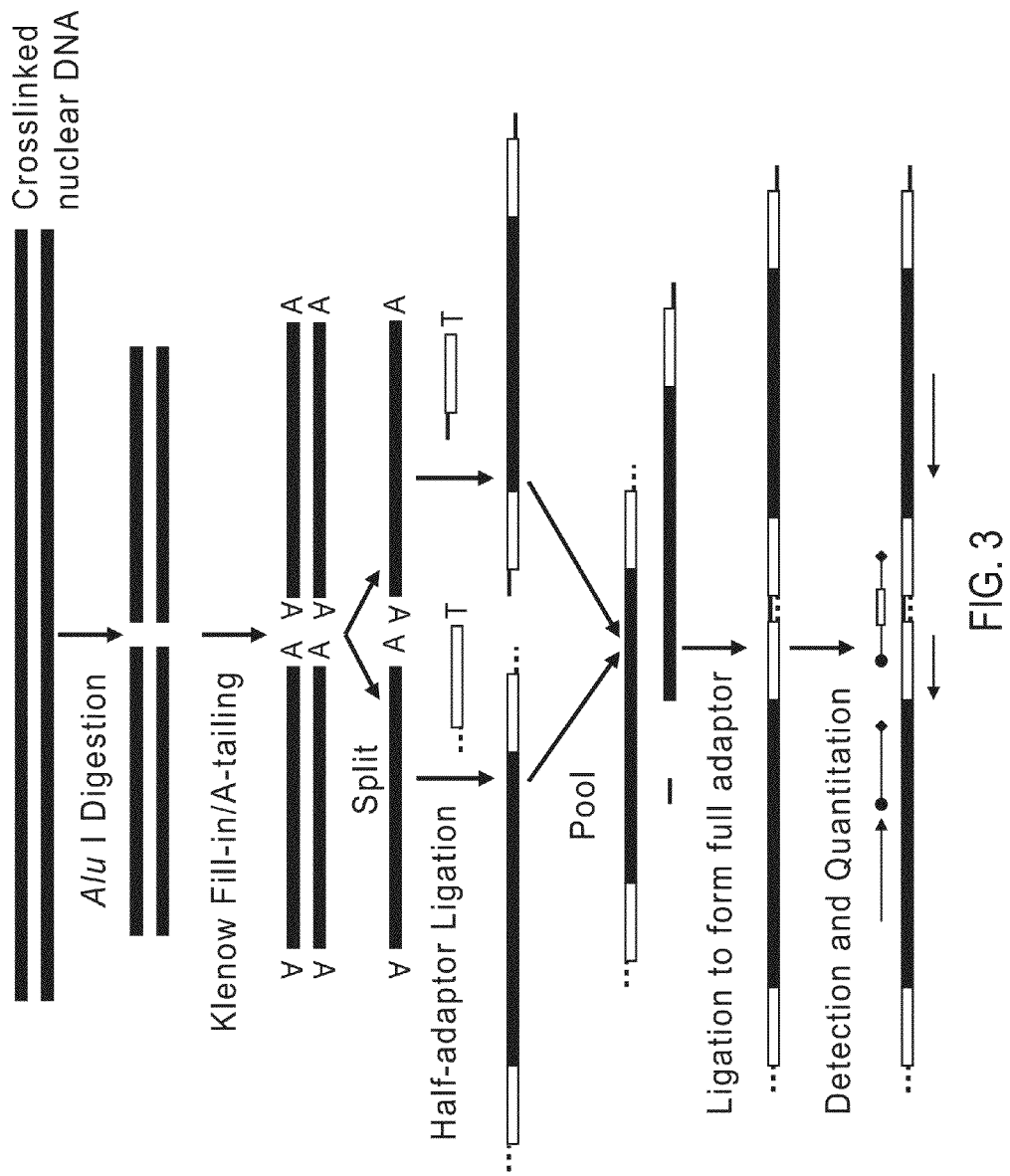
FIG. 3: A schematic representation of a method of analyzing non-specific ligation according to an embodiment of the present teachings.

In one embodiment of the methods disclosed herein, half-adaptors are provided. As provided herein, half-adaptors are double-stranded DNA molecules that have a T overhang on one end and a non-palindromic or cohesive overhang on the other end (FIG. 3). A full adaptor is formed in the following manner: half-adaptors are ligated to free ends of the DNA generated by restriction digestion of the cross-linked DNA through T:A ligation and ligation of two half-adaptors joined by their cohesive (e.g., non-palindromic) overhangs.

Another embodiment provides a method for determining the three-dimensional arrangement of chromatin in a cell (see, FIG. 4), the method including the steps of:

a) isolating cells from a biological sample;

b) incubating the cells with a cross-linking agent to cross-link proteins and DNA (e.g., chromatin or gDNA), thereby forming a cross-linked product;

c) lysing the cells;

d) digesting the DNA with a restriction enzyme;

e) filling-in and A-tailing the free ends of the digested DNA;

f) ligating a first half-adaptor to the digested DNA thereby forming a first ligation product and a second half-adaptor to the digested DNA thereby forming a second ligation product, wherein the first and second half-adaptors are different from each other and each half-adaptor comprises a non-palindromic overhang on one end and a T overhang on the other end, wherein the non-palindromic overhang of the first adaptor is complementary to the non-palindromic overhang of the second adaptor;

g) phosphorylating the first and second ligation products;

h) ligating the first and second ligation products to form a third ligation product; and i) analyzing the third ligation product.

In one embodiment, the cross-linked product is optionally incubated with a cross-linking quencher. In another embodiment, the cross-linked product is removed from the cross-linking agent by washing or separating the quencher from the cross-linked product. In one embodiment, the cells are in suspension. In another embodiment, the cells are adherent. The cells may be intact, live, permeabilized or otherwise treated depending on the method of isolation.

In one embodiment, the ligation products are analyzed by the polymerase chain reaction (PCR). In preferred embodiments, the PCR can be endpoint PCR, real-time PCR, qPCR and dPCR, most preferably, the PCR is real-time PCR and qPCR. In one embodiment, the ligation products are analyzed by DNA sequencing methods including, but not limited to, fragment analysis, dideoxy sequencing (i.e., Sanger sequencing), Maxam-Gilbert chain termination sequencing, dye terminator sequencing, dye primer sequencing, pyrosequencing, next generation sequencing methods including, high-throughput sequencing, including massively parallel signature sequencing, SOLiD sequencing (e.g., sequencing by ligation), sequencing by hybridization, proton ion semiconductor sequencing, DNA nanoball sequencing, single molecule sequencing, and nanopore sequencing.

In one embodiment, the restriction enzyme recognizes a six-base cutting sequence. In a preferred embodiment, the restriction enzyme is selected from EcoRI and HindIII. In another embodiment, the restriction enzyme yields a blunt end. In another embodiment, the filling-in step uses Klenow (exo–) DNA polymerase.

In one embodiment, the first and second half-adaptors are linear. In another embodiment, the first and second half-adaptors have a stem-loop structure. In yet another embodiment, one of the first and second half-adaptors is linear and the other has a stem-loop structure. In yet a further embodiment, one of the first and second half-adaptors is conjugated to biotin.

In another embodiment, the third ligation product is purified before the analysis and/or detection step. In one embodiment, the purifying step comprises incubating the ligation product with magnetic beads for a period of time sufficient to allow the ligation product to bind to the magnetic beads. The bound ligation product is then eluted from the beads.

Yet another embodiment (see, FIG. 5) provides a chromosome conformation method including the steps of:
a) isolating cells from a biological sample;
b) incubating the cells with a cross-linking agent to cross-link proteins and DNA (e.g., chromatin or gDNA), thereby forming a cross-linked product;
c) lysing the cells;
d) digesting the DNA with a restriction enzyme;
e) incubating the digested DNA with a phosphatase;
f) ligating a first looped half-adaptor to the digested DNA thereby forming a first ligation product and a second looped half-adaptor to the digested DNA thereby forming a second ligation product, wherein the first and second looped half-adaptors are different from each other and each looped half-adaptor comprises a stem-loop structure, wherein the 5' end of the stem comprises a cohesive (i.e., non-palindromic) end that terminates in a phosphate group;
g) heating the first and second ligation products thereby allowing the cohesive ends of each looped half-adaptors to anneal to each other;
h) phosphorylating the free ends of each of the looped half-adaptors;
i) ligating the looped half-adaptors to the DNA fragment thereby forming a third ligation product; and
i) analyzing the third ligation product.

In one embodiment, the cross-linked product is optionally incubated with a cross-linking quencher. In another embodiment, the cross-linked product is removed from the cross-linking agent by washing or separating the quencher from the cross-linked product. In one embodiment, the cells are in suspension. In another embodiment, the cells are adherent. The cells may be intact, live, permeabilized or otherwise treated depending on the method of isolation.

In one embodiment, the ligation products are analyzed by the polymerase chain reaction (PCR). In preferred embodiments, the PCR can be endpoint PCR, real-time PCR, qPCR and dPCR, most preferably, the PCR is real-time PCR and qPCR. In one embodiment, the ligation products are analyzed by DNA sequencing methods including, but not limited to, fragment analysis, dideoxy sequencing (i.e., Sanger sequencing), Maxam-Gilbert chain termination sequencing, dye terminator sequencing, dye primer sequencing, pyrosequencing, next generation sequencing methods including, high-throughput sequencing, including massively parallel signature sequencing, SOLiD sequencing (e.g., sequencing by ligation), sequencing by hybridization, proton ion semiconductor sequencing, DNA nanoball sequencing, single molecule sequencing, and nanopore sequencing.

In one embodiment, the restriction enzyme recognizes a six-base cutting sequence. In a preferred embodiment, the restriction enzyme is selected from EcoRI and HindIII. In another embodiment, the restriction enzyme yields a blunt end. In another embodiment, the filling-in step uses Klenow (exo–) DNA polymerase. In one embodiment, the heating and annealing step is replaced by a nick translation step.

In one embodiment, the first and second half-adaptors are linear. In another embodiment, the first and second half-adaptors have a stem-loop structure. In yet another embodiment, one of the first and second half-adaptors is linear and the other has a stem-loop structure. In yet a further embodiment, one of the first and second half-adaptors is conjugated to biotin.

In another embodiment, the third ligation product is purified before the analysis and/or detection step. In one embodiment, the purifying step comprises incubating the ligation product with magnetic beads for a period of time sufficient to allow the ligation product to bind to the magnetic beads. The bound ligation product is then eluted from the beads.

Yet a further embodiment (see, FIG. 6) provides a chromosomal conformation method including the steps of:
a) isolating cells from a biological sample;
b) incubating the cells with a cross-linking agent to cross-link proteins and DNA (e.g., chromatin or gDNA), thereby forming a cross-linked product;
c) lysing the cells;
d) digesting the DNA with a restriction enzyme;
e) filling-in and A-tailing the free ends of the digested DNA;
f) ligating a first looped half-adaptor to the digested DNA thereby forming a first ligation product and a second looped half-adaptor to the digested DNA thereby forming a second ligation product, wherein the first and second looped half-adaptors are different from each other and each looped half-adaptor comprises a stem-loop structure, wherein the 5' end of the stem comprises an —OH group and a 3' T overhang;
g) heating the first and second ligation products thereby allowing each of the looped half-adaptors to anneal to each other;
h) phosphorylating the free ends of each of the looped half-adaptors;
i) ligating the half-adaptors to the DNA fragment thereby forming a third ligation product; and
i) analyzing the third ligation product.

In one embodiment, the cross-linked product is optionally incubated with a cross-linking quencher. In another embodiment, the cross-linked product is removed from the cross-linking agent by washing or separating the quencher from the cross-linked product. In one embodiment, the cells are in suspension. In another embodiment, the cells are adherent. The cells may be intact, live, permeabilized or otherwise treated depending on the method of isolation.

In one embodiment, the ligation products are analyzed by the polymerase chain reaction (PCR). In preferred embodiments, the PCR can be endpoint PCR, real-time PCR, qPCR and dPCR, most preferably, the PCR is real-time PCR and qPCR. In one embodiment, the ligation products are analyzed by DNA sequencing methods including, but not limited to, fragment analysis, dideoxy sequencing (i.e., Sanger sequencing), Maxam-Gilbert chain termination sequencing, dye terminator sequencing, dye primer sequencing, pyrosequencing, next generation sequencing methods including, high-throughput sequencing, including massively parallel signature sequencing, SOLiD sequencing (e.g., sequencing by ligation), sequencing by hybridization, proton ion semiconductor sequencing, DNA nanoball sequencing, single molecule sequencing, and nanopore sequencing.

In one embodiment, the restriction enzyme recognizes a six-base cutting sequence. In a preferred embodiment, the restriction enzyme is selected from EcoRI and HindIII. In another embodiment, the restriction enzyme yields a blunt end. In another embodiment, the filling-in step uses Klenow (exo–) DNA polymerase. In one embodiment, the filling-in step is replaced by a phosphatase step. In another embodiment the phosphorylation and ligation steps are replaced by a nick translation step.

In one embodiment, the first and second half-adaptors are linear. In another embodiment, the first and second half-adaptors have a stem-loop structure. In yet another embodiment, one of the first and second half-adaptors is linear and the other has a stem-loop structure. In yet a further embodiment, one of the first and second half-adaptors is conjugated to biotin.

In another embodiment, the third ligation product is purified before the analysis and/or detection step. In one embodiment, the purifying step comprises incubating the ligation product with magnetic beads for a period of time sufficient to allow the ligation product to bind to the magnetic beads. The bound ligation product is then eluted from the beads.

Another embodiment provides a method of creating a library for chromosome conformation analysis (see, FIG. 7), the method including the steps of:
a) isolating cells from a biological sample;
b) incubating the cells with a cross-linking agent to cross-link proteins and DNA (e.g., chromatin or gDNA), thereby forming a cross-linked product;
c) lysing the cells;
d) digesting the DNA with a restriction enzyme;
e) filling-in and A-tailing the free ends of the digested DNA;
f) optionally methylating the digested DNA;
g) ligating a first half-adaptor to the digested DNA thereby forming a first ligation product and a second half-adaptor to the digested DNA thereby forming a second ligation product, wherein the first and second half-adaptors are different from each other and each half-adaptor comprises a non-palindromic overhang on one end and a T overhang on the other end, wherein the non-palindromic overhang of the first adaptor is complementary to the non-palindromic overhang of the second adaptor, further wherein the first or the second half-adaptor is biotinylated;
h) phosphorylating the ligated half-adaptors;
i) nick ligating the first and second ligation products, thereby forming a third ligation product;
j) reversing the cross-linking;
k) purifying the third ligation product;
l) digesting the third ligation product with a restriction endonuclease;
m) filling-in and A-tailing the free ends of the digested DNA
n) isolating the digested DNA using streptavidin beads;
o) ligating the digested DNA with sequencing primers;
p) analyzing the DNA.

In one embodiment, the cross-linked product is optionally incubated with a cross-linking quencher. In another embodiment, the cross-linked product is removed from the cross-linking agent by washing or separating the quencher from the cross-linked product. In one embodiment, the cells are in suspension. In another embodiment, the cells are adherent. The cells may be intact, live, permeabilized or otherwise treated depending on the method of isolation.

In one embodiment, the ligation products are analyzed by the polymerase chain reaction (PCR). In preferred embodiments, the PCR can be endpoint PCR, real-time PCR, qPCR and dPCR, most preferably, the PCR is real-time PCR and qPCR. In one embodiment, the ligation products are analyzed by DNA sequencing methods including, but not limited to, fragment analysis, dideoxy sequencing (i.e., Sanger sequencing), Maxam-Gilbert chain termination sequencing, dye terminator sequencing, dye primer sequencing, pyrosequencing, next generation sequencing methods including, high-throughput sequencing, including massively parallel signature sequencing, SOLiD sequencing (e.g., sequencing by ligation), sequencing by hybridization, proton ion semiconductor sequencing, DNA nanoball sequencing, single molecule sequencing, and nanopore sequencing.

In one embodiment, the restriction enzyme is selected from a Type IIS or Type III restriction endonuclease. In a preferred embodiment, the restriction enzyme is selected from MmeI and EcoP15I. In another embodiment, the restriction enzyme yields a blunt end. In another embodiment, the filling-in step uses Klenow (exo–) DNA polymerase.

In one embodiment, the first and second half-adaptors are linear. In another embodiment, the first and second half-adaptors have a stem-loop structure. In yet another embodiment, one of the first and second half-adaptors is linear and the other has a stem-loop structure.

In another embodiment, the third ligation product is purified before the analysis and/or detection step. In one embodiment, the purifying step comprises incubating the ligation product with magnetic beads for a period of time sufficient to allow the ligation product to bind to the magnetic beads. The bound ligation product is then eluted from the beads.

In one embodiment of the methods disclosed herein, cross-linking the DNA and the proteins interacting with the DNA is performed by using a cross-linking reagent, such as an agent that can reversibly cross-link primary amino groups in proteins with other nearby nitrogen atoms in other proteins or DNA. Such cross-linking agents include, but are not limited to, formaldehyde, paraformaldehyde, formalin, other similar aldehyde compounds, and other bi-functional cross-linking reagents that can covalently cross-link protein-protein and protein-DNA molecules together. The cross-linking reaction may be quenched, or inhibited, by the addition of an amine quenching reagent. Exemplary amine quenching reagents include, but are not limited to, methylamine, ethanolamine, Tris, dimethylamine, methylethanolamine, trimethylamine, aziridine, piperidiene, amiline, glycine, asparagine, and glutamine.

In the methods disclosed herein, the cross-linked cells and DNA complexes may be lysed. In preferred embodiments, the cells are lysed in a detergent-containing solution. The detergents that may be used in embodiments of the methods disclosed herein include, but are not limited to, anionic detergents, cationic detergents, non-ionic detergents and zwitterionic detergents, or combinations thereof. Such combinations include: one or more cationic detergents with one or more anionic detergents; one or more cationic detergents with one or more non-ionic detergents; one or more cationic detergents with one or more zwitterionic detergents; one or more anionic detergents with one or more non-ionic detergents; one or more anionic detergents with one or more zwitterionic detergents; and one or more non-ionic detergents with one or more zwitterionic detergents. Preferred combinations are one or more ionic detergent with one or more non-ionic detergent. Non-limiting examples of anionic detergents include alkyl sulfates (e.g., sodium dodecylsulfate), alkyl sulfonates (e.g., octane sulfonic acid), bile salts, docusate sodium salt, and N-laurylsarcosine. Non-limiting examples of cationic detergents include bezalkonium chloride, cetyl pyridium chloride, dodecyltrimethylammonium chloride, Girard's reagent, and Hyamine® 1622. Non-limiting examples of non-ionic detergents include Tween®-20, Tween® 80, Triton® X-100, Triton® X-114, PEGylates, IGEPAL, Nonidet™-P40, Pluronic® F-68, Poloxamer 407, saponin and Tergitol®. Non-limiting examples of zwitterionic detergents include CHAPS, L-α-lysophosphatidyl choline, DDMAB, and miltefosine.

After the lysis step, the cross-linked DNA may be digested. In preferred embodiments, the DNA is digested using restriction endonucleases. Any type of restriction endonuclease may be used to digest the cross-linked DNA. Preferably, the restriction endonuclease has a six base recognition sequence, but it may have an eight base recognition sequence, a seven base recognition sequence, a five base recognition sequence or a four base recognition sequence. Such restriction endonucleases that may be used in the methods described herein include, but are not limited to, Alu I, Apo I, Ase I, BamH I, BfuC I, Bgl II, BsaJ I, BstKT I, BstY I, Btg I, Cla I, CviKI-1, Dpn I, Dpn II, Eco47 III, EcoR I, EcoR V, EcoP15I, Fai I, Hae III, Hind III, Hpa II, HpyCH4 III, Kpn I, Mbo I, Mnl I, Mse I, Msp I, Nco I, Nde I, Nhe I, Not I, Pst I, Rsa I, Sac I, Sac II, Sal I, Sau3A I, Sfi I, Sma I, Taq I, Tsp509 I, Xba I, Xho I and Xma I. After digestion, the restriction endonuclease digestion may be terminated. In preferred embodiments, the digestion may be terminated by the addition of a restriction stop solution and a neutralizing solution. In another embodiment, the endonuclease digestion may be stopped by heat treatment.

After the digestion step, the free ends of the digested DNA fragments that have a 5'-overhang may be filled in with a dNTP. In preferred embodiments, the overhang is filled-in using Klenow enzyme (exo⁻). By adding the dA moiety to the free ends of the digested DNA fragments, ligation to the half-adaptors with a T overhang is facilitated.

In one embodiment, each half-adaptor is a double-stranded DNA molecule that has a T overhang on one end and a non-palindromic or cohesive overhang on the other end (see FIGS. 3-7). A full adaptor can be generated in the following manner: half-adaptors are ligated to free DNA ends generated by restriction digestion of cross-linked chromatin through T:A ligation and by ligating two half-adaptors joined by their cohesive (i.e., non-palindromic) overhangs. Other methods of ligation, including blunt-ended ligation and cohesive overhang ligation may be used depending on the restriction enzyme used.

In another embodiment, each half-adaptor is a double-stranded DNA molecule that comprises a stem-loop conformation (herein referred to as a "looped adaptor"), wherein the 5' end of the stem comprises a cohesive (or non-palindromic) overhang that terminates in a 5' phosphate group. Furthermore, the overhang portion of each looped half-adaptor is complementary to the other (see FIG. 5). In this embodiment, a full adaptor is formed by the overhang portions of the two looped half-adaptors annealing with each other (e.g., the overhang portion of looped half-adaptor "A" is complementary to and anneals with the overhang portion of looped half-adaptor "B").

In another embodiment, each half-adaptor is a looped half-adaptor, wherein the 5' end of the stem comprises a 5'-OH group and a 3' T-overhang. In addition, the overhang portion of each looped half-adaptor is complementary to the other (see FIG. 6). In this embodiment, a full adaptor is formed by the overhang portions of the two looped half-adaptors annealing with each other (e.g., the overhang portion of looped half-adaptor "A" is complementary to and anneals with the overhang portion of looped half-adaptor "B").

The use of half-adaptors with non-palindromic overhangs removes the bias for ligation of proximal sites and allows for increased ligation of long-range interacting sites because each free end of the digested DNA can ligate to either of the two types of half-adaptors. For example, each free end of the digested DNA may be ligated to half-adaptor "A" or half-adaptor "B"; however, only half-adaptors A and B will ligate with each other to form a full adaptor. The other combinations of half-adaptors, e.g., A-A and B-B will not form a full adaptor. Therefore, only 50% of the possible half-adaptor ligation events will result in the formation of a full adaptor. Accordingly, if the most proximal half-adaptor is not capable of forming a full adaptor, the half-adaptor will ligate with the next available half-adaptor that will form a full adaptor.

After digestion and dA tailing, the cross-linked DNA fragments may be ligated using a ligase that is specific for double-stranded DNA. Such ligases include, but are not limited to, T4 DNA ligase, Tfi DNA ligase, DNA ligase I, DNA ligase II, DNA ligase III, DNA ligase IV, and small footprint DNA ligases.

In addition, depending on the type of half-adaptors used, the adaptors may be phosphorylated in order to facilitate the ligation. Kinases useful for phosphorylating polynucleotides include, but are not limited to, T7 polynucleotide kinase and T4 polynucleotide kinase (PNK). Preferably, the kinase is T4 polynucletoide kinase.

In other embodiments of the present teachings, nick-translation with, for example, *E. coli* DNA polymerase I, is carried out instead of the phosphorylation and ligation of annealed looped adaptors. In nick translation, free 3'-hydroxyl groups are created within the DNA by "nicks" caused by DNase I treatment or by the free 3'-OH groups resulting from the annealed looped adaptors. DNA polymerase I then catalyzes the addition of a nucleotide (labeled or unlabeled) to the 3'-hydroxyl terminus of the nick. At the same time, the 5'-to-3' exonuclease activity of this enzyme eliminates the nucleotide unit from the 5'-phosphoryl terminus of the nick. A new nucleotide with a free 3'-OH group is incorporated at the position of the original excised nucleotide unit in the 3' direction.

Once ligation of the digested genomic DNA with half-adaptors to create a full adaptor is completed, the cross-linking is reversed, for example with Proteinase K, and the ligated DNA is purified. Purification may be performed using several methods known in the art including, but not limited to, magnetic beads, spin columns, gel purification, and affinity purification using, for example, biotin/streptavidin.

As used herein, the term "DNA" refers to deoxyribonucleic acid in its various forms as understood in the art, such as genomic DNA (gDNA), cDNA, isolated nucleic acid molecules, vector DNA, chromosomal DNA and chromatin. "Nucleic acid" refers to DNA or RNA in any form.

As used herein, the term "enzymatically active mutant or variant thereof," when used in reference to an enzyme such as a polymerase or a ligase, means a protein with appropriate enzymatic activity. Thus, for example, but without limitation, an enzymatically active mutant or variant of a DNA polymerase is a protein that is able to catalyze the stepwise addition of appropriate deoxynucleoside triphosphates into a nascent DNA strand in a template-dependent manner. An enzymatically active mutant or variant differs from the "generally-accepted" or consensus sequence for that enzyme by at least one amino acid, including, but not limited to, substitutions of one or more amino acids, addition of one or more amino acids, deletion of one or more amino acids, and alterations to the amino acids themselves. With the change, however, at least some catalytic activity is retained. In certain embodiments, the changes involve conservative amino acid substitutions. Conservative amino acid substitution may involve replacing one amino acid with another that has, for example, similar hydrophobicity, hydrophilicity, charge, or aromaticity. In certain embodiments, conservative amino acid substitutions may be made on the basis of similar hydropathic indices. A hydropathic index takes into account the hydrophobicity and charge characteristics of an amino acid, and in certain embodiments, may be used as a guide for selecting conservative amino acid substitutions. It is understood in the art that conservative amino acid substitutions may be made on the basis of any of the aforementioned characteristics.

Alterations to the amino acids may include, but are not limited to, glycosylation, methylation, phosphorylation, biotinylation, and any covalent and noncovalent additions to a protein that do not result in a change in amino acid sequence. "Amino acid" as used herein refers to any amino acid, natural or nonnatural, that may be incorporated, either enzymatically or synthetically, into a polypeptide or protein.

Fragments, for example, but without limitation, proteolytic cleavage products, are also encompassed by this term, provided that at least some enzyme catalytic activity is retained.

The skilled artisan will readily be able to measure catalytic activity using an appropriate well-known assay. Thus, an appropriate assay for polymerase catalytic activity might include, for example, measuring the ability of a variant to incorporate, under appropriate conditions, rNTPs or dNTPs into a nascent polynucleotide strand in a template-dependent manner. Likewise, an appropriate assay for ligase catalytic activity might include, for example, the ability to ligate adjacently hybridized oligonucleotides comprising appropriate reactive groups.

The term "sample" refers to any substance comprising nucleic acid material.

As used herein, the term "probe" comprises a polynucleotide that comprises a specific portion designed to hybridize in a sequence-specific manner with a complementary region of a specific nucleic acid sequence, e.g., a target nucleic acid sequence. In certain embodiments, the specific portion of the probe may be specific for a particular sequence, or alternatively, may be degenerate, e.g., specific for a set of sequences. In certain embodiments, the probe is labeled.

As used herein, the term "hybridization" refers to the complementary base-pairing interaction of one nucleic acid with another nucleic acid that results in the formation of a duplex, triplex or other higher-ordered structure.

As used herein, the term "anneal" refers to specific interactions between strands of nucleotides wherein the strands bind to one another substantially based on complementarity between the strands as determined by Watson-Crick base pairing or Hoogstein-type hydrogen bonding. Base-stacking and hydrophobic interactions may also contribute to duplex stability. Conditions for hybridizing probes and primers to complementary and substantially complementary target sequences are well known. In general, whether such annealing takes place is influenced by, among other things, the length of the polynucleotides and the complementarity between the bases, the pH, the temperature, the presence of mono- and divalent cations, the proportion of G and C nucleotides in the hybridizing region, the viscosity of the medium, and the presence of denaturants. Such variables influence the time required for hybridization. Thus, the preferred annealing conditions will depend upon the particular application. Such conditions, however, may be routinely determined by the person of ordinary skill in the art without undue experimentation. It will be appreciated that complementarity need not be perfect; there can be a small number of base pair mismatches that will minimally interfere with hybridization between the target sequence and the single-stranded nucleic acids of the present teachings. However, if the number of base pair mismatches is so great that no hybridization can occur under minimally stringent conditions, then the sequence is generally not a complementary target sequence. Thus, "complementarity" herein is meant that the probes or primers are sufficiently complementary to the target sequence to hybridize under the selected reaction conditions to achieve the ends of the present teachings.

As used herein, the term "amplifying" refers to any means by which at least a part of a nucleotide sequence, target polynucleotide, target polynucleotide surrogate, or combinations thereof, is reproduced, typically in a template-dependent manner, including without limitation, a broad range of techniques for amplifying nucleic acid sequences, either linearly or exponentially. Any of several methods may be used to amplify the target polynucleotide. These include linear, logarithmic, or any other amplification method. Exemplary methods include polymerase chain reaction (PCR; see, e.g., U.S. Pat. Nos. 4,683,202; 4,683,195; 4,965,188; and 5,035,996), isothermal procedures (using one or more RNA polymerases (see, e.g., WO 2006/081222), strand displacement (see, e.g., U.S. Pat. No. RE39,007), partial destruction of primer molecules (see, e.g., WO 2006/087574)), ligase chain reaction (LCR) (see, e.g., Wu, et al. Genomics 4:560-569 (1990) and Barany, et al. Proc. Natl. Acad. Sci. USA 88:189-193 (1991)), Qβ RNA replicase systems (see, e.g., WO 1994/016108), RNA transcription-based systems (e.g., TAS, 3SR), rolling circle amplification (RCA) (see, e.g., U.S. Pat. No. 5,854,033; U.S. Pub. No. 2004/265897; Lizardi, et al. Nat. Genet. 19:225-232 (1998); and Bailer, et al. Nucleic Acid Res. 26:5073-5078 (1998)), and strand displacement amplification (SDA) (Little, et al. Clin. Chem. 45:777-784 (1999)), among others. Many systems are suitable for use in amplifying target nucleic acids and are contemplated herein as would be understood by one of skill in the art.

In one embodiment, the amplification reaction is a 5'-nuclease assay (also commercially known as TaqMan®) performed using a nucleic acid polymerase, such as DNA polymerase, at least one oligonucleotide primer capable of specifically hybridizing to a target polynucleotide (from which the amplified target nucleic acid is amplified), at least one detectable probe that hybridizes to the amplified target nucleic acid, and which may be incorporated into the at least one primer), and at least one detectable nucleic acid binding agent (e.g., an intercalating or non-intercalating dye) which may be introduced before, during or after amplification. The probe typically contains a detectable label capable of emitting a signal that may be monitored to ascertain whether the target nucleic acid has been amplified. In some embodiments, the probe is an oligonucleotide that hybridizes to the target nucleic acid 3' relative to the at least one primer. In some embodiments, the polymerase has nuclease activity (i.e., 5'-to-3' nuclease activity) for releasing the probe from the amplified nucleic acid. In some embodiments, release from the amplified nucleic acid renders the probe detectable. In some embodiments, the probe comprises a detectable label and a quencher molecule that quenches the detectable label when free but does not quench when the probe is hybridized to the amplified nucleic acid. In some embodiments, two or more probes may be used where at least one probe has a detectable label and at least one other probe has a quencher molecule. When in sufficiently close proximity to one another, the quencher molecule typically suppresses the signal of the detectable label on the other probe. In some embodiments, two or more probes, each having a different detectable label, may be used without quencher molecules. In such embodiments, the probes are rendered detectable, either de novo or by exhibiting a different signal than either probe alone, when in sufficiently close proximity to one another. Typically, the detectable label and quencher molecule are part of a single probe. As amplification proceeds, the polymerase digests the probe to separate the detectable label from the quencher molecule. The detectable label (e.g., a fluorophore) is monitored during the reaction, where detection of the label corresponds to the occurrence of nucleic acid amplification (i.e., the higher the signal the greater the amount of amplification).

Additional reagents, systems, or detectable labels that may be used in the methods described herein include, for example, detectable label-quencher systems (e.g., FRET, salicylate/ DTPA ligand systems (see, e.g., Oser, et al. Angew. Chem. Int. Ed. Engl. 29:1167-1169 (1990), displacement hybridization, homologous probes, assays described in EP 070685), molecular beacons (e.g., NASBA), Scorpion® probes, locked nucleic acid (LNA) bases (Singh, et al. Chem. Commun. 4:455-456 (1998)), peptide nucleic acid (PNA) probes (Pellestor, et al. Eur. J. Hum. Gen. 12:694-700 (2004)), Eclipse probes (Afonina, et al. Biotechniques 32:940-949 (2002)), light-up probes (Svanvik, et al. Anal. Biochem. 281: 26-35 (2000)), molecular beacons (Tyagi, et al. Nat. Biotechnol. 14:303-308 (1996)), tripartite molecular beacons (Nutiu, et al. Nucleic Acids Res. 30:E94 (2002)), QuantiProbes (www.qiagen.com), HyBeacons® (French, et al. Mol. Cell. Probes 15:363-374 (2001)), displacement probes (Li, et al. Nucleic Acids Res. 30:E5 (2002)), HybProbes (Cardullo, et al. Proc. Natl. Acad. Sci. USA 85:8790-8794 (1988)), MGB Alert (www.nanogen.com), Q-PNA (Fiandaca, et al. Genome Res. 11:609-613 (2001)), Plexor® technology (www.Promega.com), LUX™ primers (Nazarenko, et al. Nucleic Acids Res. 30:E37 (2002)), Scorpion® primers (Whitcombe, et al. Nat. Biotechnol. 17:804-807 (1999)), AmpliFluor® (Sunrise) primers (Nazarenko, et al. Nucleic Acids Res. 25:2516-2521 (1997)), DzyNA primers (Todd, et al. Clin. Chem. 46:625-630 (2000)), and the like. In each of these assays, the generation of amplification products may be monitored while the reaction is in progress. An apparatus for detecting the signal generated by the detectable label may be used to detect, measure, and quantify the signal before, during, or after amplification. The particular type of signal may dictate the choice of detection method. For example, in some embodiments, fluorescent dyes are used to label probes or amplified products. The probes bind to single-stranded or double-stranded amplified products, or the dyes intercalate into the double-stranded amplified products, and consequently, the resulting fluorescence increases as the amount of amplified product increases. The use of other methods or reagents is also contemplated herein as would be understood by one of skill in the art.

As mentioned above, in some embodiments the detectable label may be attached to a probe which may be incorporated into a primer or may otherwise bind to amplified target nucleic acid (for example, a detectable nucleic acid binding agent such as an intercalating or non-intercalating dye). When using more than one detectable label, each label should differ in its spectral properties such that the labels may be distinguished from each other, or such that together the detectable labels emit a signal that is not emitted by either detectable label alone. Exemplary detectable labels include, but are not limited to, a fluorescent dye or fluorophore (i.e., a chemical group that may be excited by light to emit fluorescence or phosphorescence), "acceptor dyes" capable of quenching a fluorescent signal from a fluorescent donor dye, and the like.

Suitable detectable labels include, for example, fluoresceins (e.g., 5-carboxy-2,7-dichlorofluorescein; 5-Carboxyfluorescein (5-FAM); 5-HAT (Hydroxy Tryptamine); 6-HAT; 6-JOE; 6-carboxyfluorescein (6-FAM); FITC); Alexa fluors (e.g., 350, 405, 430, 488, 500, 514, 532, 546, 555, 568, 594, 610, 633, 635, 647, 660, 680, 700, 750); BODIPY® fluorophores (e.g., 492/515, 493/503, 500/510, 505/515, 530/550, 542/563, 558/568, 564/570, 576/589, 581/591, 630/650-X, 650/665-X, 665/676, FL, FL ATP, Fl-Ceramide, R6G SE, TMR, TMR-X conjugate, TMR-X, SE, TR, TR ATP, TR-X SE), coumarins (e.g., 7-amino-4-methylcoumarin, AMC, AMCA, AMCA-S, AMCA-X, ABQ, CPM methylcoumarin, coumarin phalloidin, hydroxycoumarin, CMFDA, methoxy- coumarin), calcein, calcein AM, calcein blue, calcium dyes (e.g., calcium crimson, calcium green, calcium orange, calcofluor white), Cascade Blue, Cascade Yellow; Cy™ dyes (e.g., 3, 3.18, 3.5, 5, 5.18, 5.5, 7), cyan GFP, cyclic AMP Fluorosensor (FiCRhR), fluorescent proteins (e.g., green fluorescent protein (e.g., GFP. EGFP), blue fluorescent protein (e.g., BFP, EBFP, EBFP2, Azurite, mKalama1), cyan fluorescent protein (e.g., ECFP, Cerulean, CyPet), yellow fluorescent protein (e.g., YFP, Citrine, Venus, YPet), FRET donor/acceptor pairs (e.g., fluorescein/tetramethylrhodamine, IAEDANS/fluorescein, EDANS/dabcyl, fluorescein/fluorescein, BODIPY® FL/BODIPY® FL, Fluorescein/QSY7 and QSY9), LysoTracker and LysoSensor (e.g., LysoTracker Blue DND-22, LysoTracker Blue-White DPX, LysoTracker Yellow HCK-123, LysoTracker Green DND-26, LysoTracker Red DND-99, LysoSensor Blue DND-167, LysoSensor Green DND-189, LysoSensor Green DND-153, LysoSensor Yellow/Blue DND-160, LysoSensor Yellow/Blue 10,000 MW dextran), Oregon Green (e.g., 488, 488-X, 500, 514); rhodamines (e.g., 110, 123, B, B 200, BB, BG, B extra, 5-carboxytetramethylrhodamine (5-TAMRA), 5 GLD, 6-Carboxyrhodamine 6G, Lissamine, Lissamine Rhodamine B, Phallicidine, Phalloidine, Red, Rhod-2,5-ROX (carboxy-X-rhodamine), Sulphorhodamine B can C, Sulphorhodamine G Extra, Tetramethylrhodamine (TRITC), WT), Texas Red, Texas Red-X, VIC and other labels described in, e.g., US Pub. No. 2009/0197254), among others as would be known to those of skill in the art. Other detectable labels can also be used (see, e.g., US Pub. No. 2009/0197254), as would be known to those of skill in the art.

As used herein, the term "incubating" refers to maintaining a state of controlled conditions such as temperature over a period of time.

As used herein, the term "denaturation" refers to the separation of nucleotide strands from an annealed state. Denaturation may be induced by a number of factors including ionic strength of a buffer, temperature, or chemicals that disrupt base pairing interactions.

As used herein, the term "sufficient amount of time" when referring to time for an enzymatic reaction, refers to the time which allows the enzyme used to complete a reaction, such as amplification, ligation or digestion. The amount of time required varies depending on several factors which are known in the art.

The term "or combinations thereof" as used herein refers to all permutations and combinations of the listed items preceding the term. For example, "A, B, C or combinations thereof" is intended to include at least one of: A, B, C, AB, AC, BC or ABC, and if order is important in a particular context, also BA, CA, CB, CBA, BCA, ACB, BAC or CAB. Continuing with this example, expressly included are combinations that contain repeats of one or more item or term, such as BB, AAA, AAB, BBA, AAABCCCC, CBBAAA, CABABB, and so forth. The skilled artisan will understand that typically there is no limit on the number of items or terms in any combination, unless otherwise apparent from the context.

As used herein, the term "reaction vessel" generally refers to any container in which a reaction may occur in accordance with the present teachings. In some embodiments, a reaction vessel may be a microcentrifuge tube or other containers of the sort in common practice in modern molecular biology laboratories.

As used herein, the term "detection" refers to any of a variety of ways of determining the presence and/or quantity and/or identity of a target polynucleotide. In some embodiments employing a donor moiety and signal moiety, one may use certain energy-transfer fluorescent dyes. Certain nonlimiting exemplary pairs of donors (donor moieties) and acceptors (signal moieties) are illustrated, e.g., in U.S. Pat. Nos. 5,863,727; 5,800,996; and 5,945,526. Use of some combinations of a donor and an acceptor have been called FRET (Fluorescent Resonance Energy Transfer). In some embodiments, fluorophores that may be used as signaling probes include, but are not limited to, rhodamine, cyanine 3 (Cy3), cyanine 5 (Cy5), fluorescein, VIC™, LIZ™, TAMRA™, 5-FAM™, 6-FAM™, and Texas Red (Molecular Probes, Eugene, Oreg.). (VIC™, LIZ™, TAMRA™, 5-FAM™, and 6-FAM™ (all available from Life Technologies, Foster City, Calif.). In some embodiments, the amount of detector probe that gives a fluorescent signal in response to an excited light typically relates to the amount of nucleic acid produced in the amplification reaction. Thus, in some embodiments, the amount of fluorescent signal is related to the amount of product created in the amplification reaction. In such embodiments, one can therefore measure the amount of amplification product by measuring the intensity of the fluorescent signal from the fluorescent indicator.

Any quencher may be used without limitation in the methods and compositions provided herein. The quencher may be located on either the primer or the probe. Any quencher may be used as long as it decreases the fluorescence intensity of the fluorophore that is being used. Quenchers commonly used for FRET include, but are not limited to, Deep Dark Quencher DDQ-I, DABCYL, Eclipse® Dark quencher, Iowa Black® FQ, BHQ-1, QSY-7, BHQ-2, DDQ-II, Iowa Black® RQ, QSY-21, and Black Hole Quencher® BHQ-3. Quenchers for use in the methods and compositions provided herein may be obtained commercially, for example, from Eurogentec (Belgium), Epoch Biosciences (Bothell, Wash.), Biosearch Technologies (Novato Calif.), Integrated DNA Technologies (Coralville, Iowa) and Life Technologies (Carlsbad, Calif.).

According to some embodiments, one may employ an internal standard to quantify the amplification product indicated by the fluorescent signal. See, e.g., U.S. Pat. No. 5,736, 333. Devices have been developed that may perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670, and include, but are not limited to the ABI Prism® 7700 Sequence Detection System, the ABI GeneAmp® 5700 Sequence Detection System, the ABI GeneAmp® 7300 Sequence Detection System, and the ABI GeneAmp® 7500 Sequence Detection System (all available from Life Technologies, Foster City, Calif.). In some embodiments, each of these functions may be performed by separate devices. For example, if one employs a Q-beta replicase reaction for amplification, the reaction may not take place in a thermal cycler, but could include a light beam emitted at a specific wavelength, detection of the fluorescent signal, and calculation and display of the amount of amplification product.

Any of the oligonucleotides provided herein (e.g., the primers or the probes) may be DNA or RNA or chimeric mixtures or derivatives or modified versions thereof, so long as the oligonucleotide is still capable of priming the desired polymerization reaction. The oligonucleotide may be modified at the base moiety, sugar moiety, or phosphate backbone, and may include other appending groups or labels, so long as the substrate is still capable of priming the desired polymerization reaction.

For example, the oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxyethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the oligonucleotide comprises at least one modified sugar moiety selected from the group including, but not limited to, arabinose, 2-fluoroarabinose, xylulose, and hexose.

In some embodiments, the oligonucleotide comprises at least one modified phosphate backbone selected from the group including, but not limited to a phosphorothioate, a phosphorodithioate, a phosphoramidothioate, a phosphoramidate, a phosphordiamidate, a methylphosphonate, an alkyl phosphotriester, and a formacetal or analog thereof.

In some embodiments, the oligonucleotides may be modified to more strongly bind to their complementary oligonucleotide. Examples of modifications that may enhance the binding or an RNA or DNA or to its complementary oligonucleotide include, but are not limited to, 2'-O-alkyl modified ribonucleotides, 2'-O-methyl ribonucleotides, 2'-orthoester modifications (including but not limited to 2'-bis (hydroxylethyl), and 2' halogen modifications and locked nucleic acids (LNAs).

As used herein "polymerase" refers to any enzyme having a nucleotide polymerizing activity. Polymerases (including DNA polymerases and RNA polymerases) useful in accordance with the present teachings include, but are not limited to, commercially available or natural DNA-directed DNA polymerases, DNA-directed RNA polymerases, RNA-directed DNA polymerases, and RNA-directed RNA polymerases. Polymerases used in accordance with the invention may be any enzyme that can synthesize a nucleic acid molecule from a nucleic acid template, typically in the 5' to 3' direction.

Exemplary DNA polymerases that may be used in the methods, kits and compositions provided herein include, but are not limited to: *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu) DNA polymerase, DEEPVENT™ DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, mycobacterium DNA polymerase (Mtb, Mlep), and mutants, and variants and derivatives thereof. RNA polymerases such as T3, T5 and SP6 and mutants, variants and derivatives thereof may also be used in accordance with the present teachings. Generally, any type I DNA polymerase may be used in accordance with the present teachings although other DNA polymerases may be used including, but not limited to, type III or family A, B, C etc., DNA polymerases.

The nucleic acid polymerases used in the methods, kits and compositions provided herein may be mesophilic or thermophilic. Exemplary mesophilic DNA polymerases include T7 DNA polymerase, T5 DNA polymerase, Klenow fragment DNA polymerase, DNA polymerase III and the like. Exemplary thermostable DNA polymerases include Taq, Tne, Tma, Pfu, Tfl, Tth, Stoffel fragment, VENT™ and DEEPVENT™ DNA polymerases, and mutants, variants and derivatives thereof (U.S. Pat. No. 5,436,149; U.S. Pat. No. 4,889,818; U.S. Pat. No. 4,965,188; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; WO 92/06188; WO 92/06200; WO 96/10640; Barnes, W. M., Gene 112:29-35 (1992); Lawyer, F. C., et al., PCR Meth. Appl. 2:275-287 (1993); Flaman, J.-M, et al., Nucl. Acids Res. 22(15):3259-3260 (1994)). Examples of DNA polymerases substantially lacking in 3' exonuclease activity include, but are not limited to, Taq, Tne (exo$^-$), Tma (exo$^-$), Pfu (exo$^-$), Pwo (exo$^-$) and Tth DNA polymerases, and mutants, variants and derivatives thereof.

DNA polymerases for use in the present teachings may be obtained commercially, for example, from Life Technologies, Inc. (Carlsbad, Calif.), Pharmacia (Piscataway, N.J.), Sigma (St. Louis, Mo.) and Boehringer Mannheim. Exemplary commercially available DNA polymerases for use in the present disclosure include, but are not limited to, Tsp DNA polymerase from Life Technologies, Inc.

In some embodiments, combined thermal cycling and fluorescence detecting devices may be used for precise quantification of target nucleic acid sequences in samples. In some embodiments, fluorescent signals may be detected and displayed during and/or after one or more thermal cycles, thus permitting monitoring of amplification products as the reactions occur in "real time." In some embodiments, one may use the amount of amplification product and number of amplification cycles to calculate how much of the target nucleic acid sequence was present in the sample prior to amplification. In some embodiments, one may simply monitor the amount of amplification product after a predetermined number of cycles sufficient to indicate the presence of the target nucleic acid sequence in the sample. One skilled in the art may easily determine, for any given sample type, primer sequence, and reaction condition, how many cycles are sufficient to determine the presence of a given target polynucleotide. As used herein, determining the presence of a target may comprise identifying it, as well as optionally quantifying it. In some embodiments, the amplification products may be scored as positive or negative as soon as a given number of cycles is complete. In some embodiments, the results may be transmitted electronically directly to a database and tabulated. Thus, in some embodiments, large numbers of samples may be processed and analyzed with less time and labor when such an instrument is used.

In some embodiments, the ligation products may be analyzed by fragment analysis. In a preferred category of methods referred to herein as "fragment analysis" methods, labeled oligonucleotide fragments are generated through template-directed enzymatic synthesis using labeled primers or nucleotides, e.g., by ligation or polymerase-directed primer extension; the fragments are subjected to a size-dependent separation process, e.g., electrophoresis or chromatography; and, the separated fragments are detected subsequent to the separation, e.g., by laser-induced fluorescence. In a preferred embodiment, multiple classes of oligonucleotides are separated simultaneously and the different classes are distinguished by spectrally resolvable labels.

One exemplary fragment analysis method is DNA sequencing. In general, DNA sequencing involves an extension/termination reaction of an oligonucleotide primer. Included in the reaction mixture are deoxynucleoside triphosphates (dNTPs) which are used to extend the primer. Also included in the reaction mixture is at least one dideoxynucleoside triphosphates (ddNTP) which when incorporated onto the extended primer prevents the further extension of the primer. After the extension reaction has been terminated, the different termination products that are formed are separated and analyzed in order to determine the positioning of the different nucleosides.

Fluorescent DNA sequencing may generally be divided into two categories: "dye primer sequencing" and "dye terminator sequencing." In dye primer sequencing, a fluorescent dye is incorporated onto the primer being extended. Four separate extension/termination reactions are then run in parallel, each extension reaction containing a different dideoxynucleoside triphosphates (ddNTP) to terminate the extension reaction. After termination, the reaction products are separated by gel electrophoresis and analyzed. See, for example, Ansorage et al., Nucl. Acids Res. 15:4593-4602 (1987).

In one variation of dye primer sequencing, different primers are used in the four separate extension/termination reactions, each primer containing a different spectrally resolvable dye. After termination, the reaction products from the four extension/termination reactions are pooled, electrophoretically separated, and detected in a single lane. See, for example, Smith et al., Nature 321:674-679 (1986). Thus, in this variation of dye primer sequencing, by using primers containing a set of spectrally resolvable dyes, products from more than one extension/termination reactions can be simultaneously detected. According to this method, a mixture of extended labeled primers are formed by hybridizing a nucleic acid sequence with a fluorescently labeled oligonucleotide primer in the presence of deoxynucleoside triphosphates, at least one dideoxynucleoside triphosphates and a DNA polymerase. The fluorescently labeled oligonucleotide primer includes an oligonucleotide sequence complementary to a portion of the nucleic acid being sequenced, and a fluorescent dye attached to the oligonucleotide, preferably an energy transfer dye. According to this method, the DNA polymerase extends the primer with the deoxynucleoside triphosphates until a dideoxynucleoside triphosphate is incorporated with terminates extension of the primer. After termination, the mixture of extended primers is separated. The sequence of the nucleic acid sequence is then determined by fluorescently detecting the mixture of extended primers formed.

In dye terminator sequencing, a fluorescent dye is attached to each of the dideoxynucleoside triphosphates. An extension/termination reaction is then conducted where a primer is extended using deoxynucleoside triphosphates until the labeled dideoxynucleoside triphosphates is incorporated onto the extended primer to prevent further extension of the primer. Once terminated, the reaction products for each dideoxynucleoside triphosphates are separated and detected. In one embodiment, separate extension/termination reactions are conducted for each of the four dideoxynucleoside triphosphates. In another embodiment, a single extension/termination reaction is conducted which contains the four dideoxynucleoside triphosphates, each labeled with a different, spectrally resolvable, fluorescent dye. According to this method, a mixture of extended primers is formed by hybridizing a nucleic acid sequence with an oligonucleotide primer in the presence of deoxynucleoside triphosphates, at least one fluorescently labeled dideoxynucleotide triphosphates, and a DNA polymerase. The fluorescently labeled dideoxynucleotide triphosphates include a dideoxynucleoside triphosphates labeled with a fluorescent dye, preferably an energy transfer dye. According to this method, the DNA polymerase extends the primer with the deoxynucleoside triphosphates until a fluorescently labeled dideoxynucleoside triphosphates is incorporated onto the extended primer. After termination, the mixture of extended primers is separated. The sequence of the nucleic acid sequence is then determined by detecting the fluorescently labeled dideoxynucleoside attached to the extended primer.

In some embodiments, the sequence of at least part of the ligation product is determined thereby detecting the intra- and interchromosomal interactions. The term "DNA sequencing" is used in a broad sense herein and refers to any technique known in the art that allows the order of at least some consecutive nucleotides in at least part of a DNA to be identified. Some non-limiting examples of DNA sequencing techniques include Sanger's dideoxy terminator method and the chemical cleavage method of Maxam and Gilbert, including variations of those methods; sequencing by hybridization, for example, but not limited to, hybridization of amplified products to a microarray or a bead, such as a bead array; pyrosequencing, and restriction mapping. Some DNA sequencing methods comprise electrophoresis, including without limitation, capillary electrophoresis and gel electrophoresis; mass spectroscopy; and single molecule detection. In some embodiments, DNA sequencing comprises direct sequencing, duplex sequencing, cycle sequencing, single-base extension sequencing (SBE), solid-phase sequencing, or combinations thereof. In some embodiments, DNA sequencing comprises detecting the sequencing product using an instrument, for example, but not limited to, an ABI PRISM® 377 DNA Sequencer, an ABI PRISM® 310, 3100, 3100-Avant, 3730 or 3730×1 Genetic Analyzer, an ABI PRISM® 3700 DNA Analyzer or an Applied Biosystems SOLiD™ System, or an Ion PGM™ sequencer (all available from Life Technologies, Carlsbad, Calif.), a Genome Sequencer 20 System (Roche Applied Science), or a mass spectrometer. In certain embodiments, DNA sequencing comprises emulsion PCR (see, e.g., Williams et al, Nat. Methods 3:545-550 (2006)). In certain embodiments, DNA sequencing comprises a high throughput sequencing technique, for example, but not limited to, massively parallel signature sequencing (MPSS). Descriptions of MPSS can be found, among other places, in Zhou et al, Methods of Molecular Biology, 331:285-311, Humana Press Inc.; Reinartz et al, Briefings in Functional Genomics and Proteomics, 1:95-104 (2002); Jongeneel et al., Genome Research 15:1007-14 (2005)). In some embodiments, DNA sequencing comprises incorporating a dNTP, including without limitation, a dATP, a dCTP, a dGTP, a dTTP, a dUTP, a dITP, or combinations thereof, and including dideoxyribonucleotide versions of dNTPs, into an amplified product.

Further exemplary techniques that are useful for determining the sequence of at least a portion of a nucleic acid molecule include, without limitation, emulsion-based PCR followed by any suitable massively parallel sequencing or other high-throughput technique. In some embodiments, determining the sequence of at least a part of an amplified product to detect the corresponding RNA or DNA molecule comprises quantitating the amplified product. In some embodiments, sequencing is carried out using the SOLiD™ System (Applied Biosystems) as described in, for example, PCT Application Publication No. WO 06/084132 and WO 07/121,489. In some embodiments, sequencing is carried out using the Ion PGM™ Sequencer, as discussed in, for example, Rothberg et al., Nature 475:348-352 (2011). In some embodiments, quantitating the amplified product comprises real-time or end-point quantitative PCR or both. In some embodiments, quantitating the amplified product comprises one or more 5'-nuclease assays, for example, but not limited to, TaqMan® Gene Expression Assays, which may comprise a microfluidics device including without limitation, a low density array. Any suitable expression profiling technique known in the art may be employed in various embodiments of the disclosed methods.

Those in the art will appreciate that the sequencing method employed is not typically a limitation of the present methods. Rather, any sequencing technique that provides the order of at least some consecutive nucleotides of at least part of the corresponding amplified product or DNA to be detected may typically be used in the current methods. In some embodiments, unincorporated primers and/or dNTPs are removed prior to a sequencing step by enzymatic degradation, including without limitation, exonuclease I and shrimp alkaline phosphatase digestion, for example, but not limited to, the ExoSAP-IT® reagent (USB Corporation). In some embodiments, unincorporated primers, dNTPs and/or ddNTPs are removed by gel or column purification, sedimentation, filtration, beads, magnetic separation, or hybridization-based pull out, as appropriate.

In certain embodiments, the present teachings also provide kits designed to expedite performing certain methods. In some embodiments, kits serve to expedite the performance of the methods of interest by assembling two or more components used in carrying out the methods. In some embodiments, kits may contain components in pre-measured unit amounts to minimize the need for measurements by end-users. In some embodiments, kits may include instructions for performing one or more methods of the present teachings. In certain embodiments, the kit components are optimized to operate in conjunction with one another.

In another embodiment, the present compositions and methods may be assembled into kits for use in chromosome conformation analysis. Kits according to this embodiment may comprise a carrier means, such as a box, carton, tube or the like, having in close confinement therein one or more container means or reaction vessel, such as vials, tubes, ampoules, plates, bottles, and the like, wherein one or more container means contains: a cross-linking agent, a lysing solution, a DNA ligase, and a protease. In another embodiment, the kit further provides a cross-linking quencher. In yet another embodiment, the kit further provides magnetic beads, a DNA binding solution, a DNA washing solution, and a DNA elution solution. In yet another embodiment, the kit further provides a protease inhibitor cocktail, a restriction enzyme stop solution, and a neutralization solution. In another embodiment, the kit comprises control assays, wherein the control assays include Assay 1 and Assay 2, and a first and second half-adaptor. In a further embodiment, the kits disclosed herein may further comprise one or more of the following: a buffer, such as phosphate buffer saline, and RNase A. In a further embodiment, the kits disclosed herein may further comprise instructions for carrying out the methods disclosed herein.

In a specific embodiment, the chromosome conformation kits may comprise one or more additional components, in mixtures or separately. Those of skill in the art will understand that the additional components, either in the same tube or in separate tubes, may also be included in the kit to further facilitate or enhance reactions such as ligation, amplification, cross-linking and restriction digestion. Such components or additives, can include for example, $Mg^{2+}$, uracil DNA glycosylase, a passive reference control to minimize sample-to-sample or well-to-well variations in quantitative real-time DNA-detection assays (e.g., dyes such as ROX) and various hot start components (e.g., antibodies, oligonucleotides, beads, etc).

In another embodiment, the compositions in the present kits may be formulated as concentrated stock solutions (e.g., 2×, 3×, 4×, 5×, 6×, etc). In some embodiments, the compositions may be formulated as concentrated stock solutions in a single tube or container. Collectively, some of the components of the kits according to the present teachings may be formulated together to create a master mix. Components of the kit other than the compositions disclosed herein may be provided in individual containers or in a single container, as appropriate. Instructions and protocols for using the kit advantageously may be provided.

In some embodiments, the kit comprises a multi-well format platform, such as a 96-well plate, a 394-well plate, a 1536-well plate, an Open Array™ multi-well plate, TaqMan® Low Density Array (TLDA) plate, an Ion 314™ chip, an Ion 316™ chip, and an Ion 318™ chip. Such multi-well format platform may be used for analysis of multiple samples including control enzymes and multiple concentrations of the standard duplex for the generation of a standard curve.

In another embodiment, compositions are provided. Typically, the compositions comprise one or more components that are useful for practicing at least one embodiment of the methods disclosed in the present teachings, or are produced through practice of at least one embodiment of the methods disclosed in the present teachings. The compositions are not limited in their physical form, but are typically solids or liquids, or combinations of these. Furthermore, the compositions may be present in any suitable environment, including, but not limited to, reaction vessels (e.g., microfuge tubes, PCR tubes, plastic multi-well plates, microarrays), vials, ampoules, bottles, bags, and the like. In situations where a composition comprises a single substance according to the present teachings, the composition will typically comprise some other substance, such as water or an aqueous solution, one or more salts, buffering agents, and/or biological material. Compositions of the present teachings may comprise one or more of the components of the present teachings, in any ratio or form. Likewise, they may comprise some or all of the reagents or molecules necessary for cross-linking of genomic DNA and protein, ligation of half-adaptors and/or digested DNA, digestion of the cross-linked product and/or DNA template, amplification of the ligation products, or combinations thereof. Thus, the compositions may comprise ATP, magnesium or manganese salts, nucleotide triphosphates, and the like. They also may comprise some or all of the components necessary for generation of a signal from a labeled nucleic acid.

A composition of the present teachings may comprise one or more half-adaptors, for example, two or more half-adaptors. The half-adaptors may be any half-adaptor according to the present teachings, in any number of copies, any amount, or any concentration. The practitioner can easily determine suitable amounts and concentrations based on the particular use envisioned at the time. Thus, a composition according to the present teachings may comprise a single half-adaptor. On the other hand, it may comprise two or more half-adaptors, each of which may have the same or a different sequence, or have the same or a different label or capability for labeling, from all others in the composition. Non-limiting examples of compositions of the present teachings include compositions comprising two or more half-adaptors and a sample containing or suspected of containing a cross-linked product including gDNA and protein. Other non-limiting examples include compositions comprising one or more half-adaptors, a sample containing or suspected of containing a gDNA-protein cross-linked product, and at least one ligase, which is capable under the appropriate conditions, of catalyzing the ligation of a half-adaptor to the cross-linked product and/or to another half-adaptor. Yet other non-limiting examples of compositions include those comprising two or more half-adaptors, a sample containing or suspected of containing a cross-linked product, at least one ligase, and at least one restriction endonuclease. Yet other non-limiting examples of compositions include those comprising two or more half-adaptors, a sample containing or suspected of containing a cross-linked product, at least one ligase, at least one restriction endonuclease, and at least one amplification primer. Yet other non-limiting examples of compositions include those comprising two or more half-adaptors, a sample containing or suspected of containing a cross-linked product, at least one ligase, at least one restriction endonuclease, at least one amplification primer, and at least one polymerase, which is capable under the appropriate conditions of catalyzing the polymerization of at least one amplification primer to form a polynucleotide. In certain embodiments, the compositions comprise labels or members of a labeling system.

Alternatively, a composition of the present teachings may comprise a lysis solution comprising one or more detergents as disclosed herein. Some non-limiting examples of compositions include those comprising a lysis solution comprising a combination of two or more detergents and a sample containing or suspected of containing a cross-linked product. Yet other non-limiting examples of compositions include those comprising a lysis solution comprising a combination of two or more detergents, a sample containing or suspected of containing a cross-linked product and a restriction endonuclease. Yet other non-limiting examples of compositions include those comprising a lysis solution comprising a combination of two or more detergents, a sample containing or suspected of containing a cross-linked product, a restriction endonuclease and two or more half-adaptors. Yet other non-limiting examples of compositions include those comprising a lysis solution comprising a combination of two or more detergents, a sample containing or suspected of containing a cross-linked product, a restriction endonuclease, two or more half-adaptors, and a ligase.

Alternatively, a composition of the present teachings may comprise one or more ligation products of two half-adaptors. The ligation product may be provided as the major substance in the composition, as when purified in a purified or partially purified form, or may be present as a minority of the substances in the composition. The ligation product may be provided in any number of copies, in any amount, or at any concentration in the composition, advantageous amounts being easily identified by the practitioner for each particular purpose to which the ligation product will be applied. In certain embodiments, the composition comprises agarose, polyacrylamide, or some other polymeric material that is suitable for isolating or purifying, at least to some extent, nucleic acids. In certain embodiments, the composition comprises nylon, nitrocellulose, or some other solid support to which nucleic acids can bind. In some other embodiments, the composition comprises magnetic beads to which nucleic acids can bind. In some embodiments, the compositions comprise at least one label or member or a labeling system. Two or more different ligation products may be present in a single composition.

Alternatively, a composition of the present teachings may comprise one or more amplification primers. The primer may be provided as the major component of the composition, such as in a purified or partially purified state, or may be a minor component. The primer may be any amplification primer according to the present teachings, in any number of copies, in any amount, or at any concentration. The practitioner can easily determine suitable amounts and concentrations based on the particular use envisioned at the time. In certain embodiments, a composition of the present teachings may comprise one or more bridge oligos. The bridge oligo may be provided as the major component of the composition, such as in a purified or partially purified state, or may be a minor component. The bridge oligo may be any amplification primer according to the present teachings, in any number of copies, in any amount, or at any concentration. The practitioner can easily determine suitable amounts and concentrations based on the particular use envisioned at the time.

Alternatively, a composition of the present teachings may comprise an amplification product. The amplification product may be any nucleic acid that is derived (or has ultimately been produced) from a target DNA through practice of the methods of the present teachings, where the method includes the step of amplification of the ligation product. As with other compositions comprising nucleic acids of the present teachings, compositions comprising an amplification product may comprise it in any number of copies, amount or concentration. The amplification product may be provided as the major substance in the composition, as when provided in a purified or partially purified form, or may be present as a minority of the substances in the composition. Non-limiting examples of compositions of the present teachings include compositions comprising an amplification product and a sample containing a target DNA. Other non-limiting examples include compositions comprising an amplification product and at least two amplification primers. Other non-limiting examples include those in which the composition comprises an amplification product and at least one polymerase. Yet other non-limiting examples include compositions comprising an amplification product and at least one member of a labeling system. Yet other non-limiting examples include compositions comprising an amplification product and at least one ligase. Other non-limiting examples include compositions comprising an amplification product and a ligation product. Further non-limiting examples include compositions comprising a target DNA, a digested DNA and/or a cross-linked product, at least one half-adaptor, at least one ligase, at least one ligation product, at least one amplification primer, at least one restriction endonuclease, at least one polymerse, at least one bridge oligo and an amplification product. In certain embodiments, the composition comprises agarose, polyacrylamide, or some other polymeric material that is suitable for isolating or purifying, at least to some extent, nucleic acids. In certain embodiments, the composition comprises nylon, nitrocellulose, or some other solid support to which nucleic acids can bind. In some other embodiments, the composition comprises magnetic beads to which nucleic acids can bind. In some embodiments, the compositions comprise at least one label or member or a labeling system. Two or more different ligation products may be present in a single composition.

Compositions of the present teachings may comprise one or more nucleic acid polymerase. The polymerase may be any polymerase known to those skilled in the art as being useful for polymerizing a nucleic acid molecule from a primer using a strand of nucleic acid as a template for incorporation of nucleotide bases. Thus, it may be, for example, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu) DNA polymerase, DEEPVENT™ DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, mycobacterium DNA polymerase (Mtb, Mlep), and mutants, and variants and derivatives thereof. Generally, any type I DNA polymerase may be used in accordance with the present teachings although other DNA polymerases may be used including, but not limited to, type III or family A, B, C etc., DNA polymerases. In addition, the nucleic acid polymerases may be mesophilic or thermophilic. Exemplary mesophilic DNA polymerases include T7 DNA polymerase, T5 DNA polymerase, Klenow fragment DNA polymerase, DNA polymerase III and the like. Exemplary thermostable DNA polymerases include Taq, Tne, Tma, Pfu, Tfl, Tth, Stoffel fragment, VENT™ and DEEPVENT™ DNA polymerases, and mutants, variants and derivatives thereof.

Compositions of the present teachings may comprise one or more ligase. The ligase may be any ligase known to those skilled in the art as being useful for ligating a nucleic acid molecule. Thus, it may be, for example, T4 DNA ligase, Tfi DNA ligase, DNA ligase I, DNA ligase II, DNA ligase III, DNA ligase IV, and small footprint DNA ligases.

According to another embodiment of the present teachings, the chromosome conformation analysis methods disclosed herein may be used in diagnostic and/or prognostic methods for identifying diseases or in determining patient response to treatment with certain drugs, medications or methods of therapy. An exemplary condition that can be associated with the three dimensional structure of chromatin is cancer. Thus, the present teachings provide a method of diagnosing susceptibility to a cancer or prognosis of outcome for treatment of cancer.

The prognostic methods of the present teachings are useful for determining if a patient is at risk for recurrence. Cancer recurrence is a concern relating to a variety of types of cancer. For example, of patients undergoing complete surgical removal of colon cancer, 25-40% of patients with stage II colon carcinoma and about 50% of patients with stage III colon carcinoma experience cancer recurrence. One explanation for cancer recurrence is that patients with relatively early stage disease, for example, stage II or stage III, already have small amounts of cancer spread outside of the affected organ that were not removed by surgery. These cancer cells, referred to as micrometastases, cannot typically be detected with currently available tests.

The prognostic methods disclosed herein can be used to identify surgically treated patients likely to experience cancer recurrence so that they can be offered additional therapeutic options, including preoperative or postoperative adjuncts such as chemotherapy, radiation, biological modifiers and other suitable therapies. The methods are especially effective for determining the risk of metastasis in patients who demonstrate no measurable metastasis at the time of examination or surgery.

The prognostic methods according to certain embodiments also are useful for determining a proper course of treatment for a patient having cancer. A course of treatment refers to the therapeutic measures taken for a patient after diagnosis or after treatment for cancer. For example, a determination of the likelihood for cancer recurrence, spread, or patient survival, can assist in determining whether a more conservative or more radical approach to therapy should be taken, or whether treatment modalities should be combined. For example, when cancer recurrence is likely, it can be advantageous to precede or follow surgical treatment with chemotherapy, radiation, immunotherapy, biological modifier therapy, gene therapy, vaccines, and the like, or adjust the span of time during which the patient is treated. As described herein, the diagnosis or prognosis of cancer state can be associated with the three-dimensional conformation of the patient's chromatin structure. Recent studies suggest that epigenetic alterations may be the key initiating events in some forms of cancers and global changes in the epigenome are a hallmark of cancers.

Exemplary cancers that may be evaluated using a method as disclosed herein include, but are not limited to hematoporetic neoplasms, Adult T-cell leukemia/lymphoma, Lymphoid Neoplasms, Anaplastic large cell lymphoma, Myeloid Neoplasms, Histiocytoses, Hodgkin Diseases (HD), Precursor B lymphoblastic leukemia/lymphoma (ALL), Acute myclogenous leukemia (AML), Precursor T lymphoblastic leukemia/lymphoma (ALL), Myclodysplastic syndromes, Chronic Mycloproliferative disorders, Chronic lymphocytic leukemia/small lymphocytic lymphoma (SLL), Chronic Myclogenous Leukemia (CML), Lymphoplasmacytic lymphoma, Polycythemia Vera, Mantle cell lymphoma, Essential Thrombocytosis, Follicular lymphoma, Myelofibrosis with Myeloid Metaplasia, Marginal zone lymphoma, Hairy cell leukemia, Hemangioma, Plasmacytoma/plasma cell myeloma, Lymphangioma, Glomangioma, Diffuse large B-cell lymphoma, Kaposi Sarcoma, Hemanioendothelioma, Burkitt lymphoma, Angiosarcoma, T-cell chronic lymphocytic leukemia, Hemangiopericytoma, Large granular lymphocytic leukemia, head & neck cancers, Basal Cell Carcinoma, Mycosis fungoids and sezary syndrome, Squamous Cell Carcinoma, Ceruminoma, Peripheral T-cell lymphoma, Osteoma, Nonchromaffin Paraganglioma, Angioimmunoblastic T-cell lymphoma, Acoustic Neurinoma, Adenoid Cystic Carcinoma, Angiocentric lymphoma, Mucoepidermoid Carcinoma, NK/T-cell lymphoma, Malignant Mixed Tumors, Intestinal T-cell lymphoma, Adenocarcinoma, Malignant Mesothelioma, Fibrosarcoma, Sarcomotoid Type lung cancer, Osteosarcoma, Epithelial Type lung cancer, Chondrosarcoma, Melanoma, cancer of the gastrointestinal tract, olfactory Neuroblastoma, Squamous Cell Carcinoma, Isolated Plasmocytoma, Adenocarcinoma, Inverted Papillomas, Carcinoid, Undifferentiated Carcinoma, Malignant Melanoma, Mucoepidermoid Carcinoma, Adenocarcinoma, Acinic Cell Carcinoma, Gastric Carcinoma, Malignant Mixed Tumor, Gastric Lymphoma, Gastric Stromal Cell Tumors, Amenoblastoma, Lymphoma, Odontoma, Intestinal Stromal Cell tumors, thymus cancers, Malignant Thymoma, Carcinids, Type I (Invasive thymoma), Malignant Mesethelioma, Type II (Thymic carcinoma), Non-mucin producing adenocarcinoma, Squamous cell carcinoma, Lymph epithelioma, cancers of the liver and biliary tract, Squamous Cell Carcinoma, Hepatocellular Carcinoma, Adenocarcinoma, Cholangiocarcinoma, Hepatoblastoma, papillary cancer, Angiosarcoma, solid Bronchioalveolar cancer, Fibrolameller Carcinoma, Small Cell Carcinoma, Carcinoma of the Gallbladder, Intermediate Cell carcinoma, Large Cell Carcinoma, Squamous Cell Carcinoma, Undifferentiated cancer, cancer of the pancreas, cancer of the female genital tract, Squamous Cell Carcinoma, Cystadenocarcinoma, Basal Cell Carcinoma, Insulinoma, Melanoma, Gastrinoma, Fibrosarcoma, Glucagonamoa, Intaepithelial Carcinoma, Adenocarcinoma Embryonal, cancer of the kidney, Rhabdomysarcoma, Renal Cell Carcinoma, Large Cell Carcinoma, Nephroblastoma (Wilm's tumor), Neuroendocrine or Oat Cell carcinoma, cancer of the lower urinary tract, Adenosquamous Carcinoma, Urothelial Tumors, Undifferentiated Carcinoma, Squamous Cell Carcinoma, Carcinoma of the female genital tract, Mixed Carcinoma, Adenoacanthoma, Sarcoma, Small Cell Carcinoma, Carcinosarcoma, Leiomyosarcoma, Endometrial Stromal Sarcoma, cancer of the male genital tract, Serous Cystadenocarcinoma, Mucinous Cystadenocarcinoma, Sarcinoma, Endometrioid Tumors, Speretocytic Sarcinoma, Embyonal Carcinoma, Celioblastoma, Choriocarcinoma, Teratoma, Clear Cell Carcinoma, Leydig Cell Tumor, Unclassified Carcinoma, Sertoli Cell Tumor, Granulosa-Theca Cell Tumor, Sertoli-Leydig Cell Tumor, Disgerminoma, Undifferentiated Prostatic Carcinoma, Teratoma, Ductal Transitional carcinoma, breast cancer, Phyllodes Tumor, cancer of the bones joints and soft tissue, Paget's Disease, Multiple Myeloma, Insitu Carcinoma, Malignant Lymphoma, Invasive Carcinoma, Chondrosacrcoma, Mesenchymal Chondrosarcoma, cancer of the endocrine system, Osteosarcoma, Adenoma, Ewing Tumor, endocrine Carcinoma, Malignant Giant Cell Tumor, Meningnoma, Adamantinoma, Cramiopharlingioma, Malignant Fibrous Histiocytoma, Papillary Carcinoma, Histiocytoma, Follicular Carcinoma, Desmoplastic Fibroma, Medullary Carcinoma, Fibrosarcoma, Anoplastic Carcinoma, Chordoma, Adenoma, Hemangioendothelioma, Memangispericytoma, Pheochromocytoma, Liposarcoma, Neuroblastoma, Paraganglioma, Histiocytoma, Pineal cancer, Rhabdomysarcoms, Pineoblastoma, Leiomyo sarcoma, Pineocytoma, Angiosarcoma, skin cancer, cancer of the nervous system, Melanoma, Schwannoma, Squamous cell carcinoma, Neurofibroma, Basal cell carcinoma, Malignant Periferal Nerve Sheath Tumor, Merkel cell carcinoma, Sheath Tumor, Extramamary Paget's Disease, Astrocytoma, Paget's Disease of the nipple, Fibrillary Astrocytoma, Glioblastoma Multiforme, Brain Stem Glioma, Cutaneous T-cell lymphoma, Pilocytic Astrocytoma, Xanthorstrocytoma, Histiocytosis, Oligodendroglioma, Ependymoma, Gangliocytoma, Cerebral Neuroblastoma, Central Neurocytoma, Dysembryoplastic Neuroepithelial Tumor, Medulloblastoma, Malignant Meningioma, Primary Brain Lymphoma, Primary Brain Germ Cell Tumor, cancers of the eye, Squamous Cell Carcinoma, Mucoepidermoid Carcinoma, Melanoma, Retinoblastoma, Glioma, Meningioma, cancer of the heart, Myxoma, Fibroma, Lipoma, Papillary Fibroelastoma, Rhasdoyoma, or Angiosarcoma among others.

One embodiment provides methods for diagnosing the occurrence of cancer in a patient or a patient at risk for cancer. The method involves (a) determining the epigenetic interactions of the genomic DNA using any one of the chromosomal conformation analysis methods disclosed herein, and (b) comparing the epigenetic interactions to a reference sample (i.e., a sample isolated from a healthy patient, tissue or cell), wherein one or more different epigenetic interactions correlates with presence of cancer in the patient.

Another embodiment provides methods for determining a prognosis for survival for a cancer patient. One method involves (a) determining the epigenetic interactions of the genomic DNA using any one of the chromosomal conformation analysis methods disclosed herein from a sample obtained from the cancer patient, and (b) comparing the epigenetic interactions to a reference sample (i.e., a sample isolated from a healthy patient, tissue or cell), wherein one or more different epigenetic interactions correlates with increased survival of the patient.

Yet another embodiment provides a method for monitoring the effectiveness of a course of treatment for a patient with cancer. The method involves (a) determining the epigenetic interactions of the genomic DNA using any one of the chromosomal conformation analysis methods disclosed herein from a sample from the cancer patient prior to treatment, and (b) comparing the epigenetic interactions to a sample from the patient after treatment, whereby comparison of the epigenetic interactions after treatment indicates the effectiveness of the treatment.

Yet another embodiment provides a method that may be used to determine the prognosis of disease free survival or overall survival. As used herein, the term "disease-free survival" refers to the lack of recurrence of symptoms such as, in the case of cancer, lack of tumor recurrence and/or spread and the fate of a patient after diagnosis, for example, a patient who is alive without tumor recurrence. The phrase "overall survival" refers to the fate of the patient after diagnosis, regardless of whether the patient has a recurrence of symptoms such as, in the case of cancer, tumor recurrence. Tumor recurrence refers to further growth of neoplastic or cancerous cells after diagnosis of cancer. Particularly, recurrence can occur when further cancerous cell growth occurs in the cancerous tissue. Tumor spread refers to dissemination of cancer cells into local or distant tissues and organs, for example, during tumor metastasis. Tumor recurrence, in particular, metastasis, is a significant cause of mortality among patients who have undergone surgical treatment for cancer. Therefore, tumor recurrence or spread is correlated with disease-free and overall patient survival.

Similar methods to those exemplified above for cancer may be used to diagnose or prognose other conditions. For example, the methods can be useful for diagnosing early-onset inherited Parkinson's disease or other diseases that arise due to aberrant gene expression. Thus, the steps exemplified above for cancer can also be used to diagnose these other diseases, to prognose survival rate or to monitor effectiveness of a course of treatment.

While the present teachings have been described in terms of these exemplary embodiments, the skilled artisan will readily understand that numerous variations and modifications of these exemplary embodiments are possible without undue experimentation. All such variations and modifications are within the scope of the current teachings. Aspects of the present teachings may be further understood in light of the following examples, which should not be construed as limiting the scope of the teachings in any way.

EXAMPLES

Example 1

Restriction and Ligation Control Assays

Figure 2:
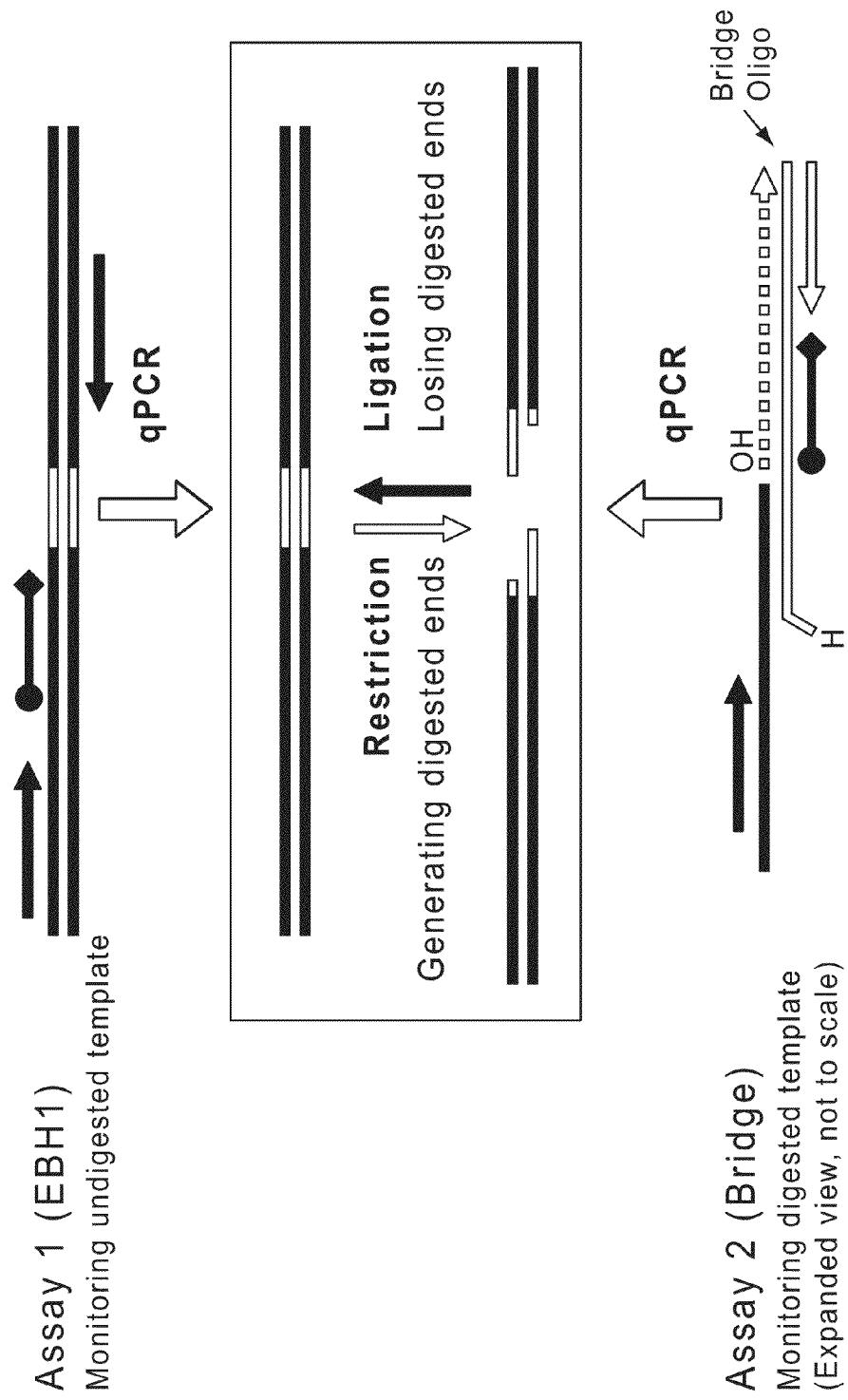
FIG. 2: A schematic representation of the restriction and ligation control assays according to embodiments of the present teachings.

Control assays were developed to provide quantitative measurement of important steps in the methods disclosed herein. qPCR control assays for the monitoring of efficiencies of restriction digestion and ligation steps were designed and tested (see, FIG. 2). Since digestion by restriction endonucleases generates new ends and ligation removes them, restriction and ligation efficiency may be monitored with one pair of assays. The generation of a restricted end (generated by restriction endonuclease digestion) reveals the efficiency of restriction digestion while the "disappearance" of a restricted end reflects ligation efficiency.

The forward primer of Assay1 was selected from a sequence upstream of the restriction site while the reverse primer was selected from a sequence downstream of the restriction site. It amplifies and detects the intact (undigested) template. It has inherently higher sensitivity and precision for high digestion efficiency (>50%) but lower sensitivity for low digestion efficiency (<50%).

However, restriction digestion is greatly hindered by the cross-linking of DNA with proteins, which reduces digestion efficiency drastically. As a result, assays that are more sensitive and precise for low digestion efficiency are needed. The embodiments of the methods disclosed herein include a new assay to detect the newly generated digested ends by using a 3'-blocked oligonucleotide (herein denoted a "bridge oligo") to anneal to the sequence at the restriction site. The bridge oligo may be copied thorough the extension of the newly generated 3' end at the restriction recognition site.

The bridge oligo contains a 3' sequence to anneal to the digested end and a 5'-region to hybridize with TaqMan® probe and reverse primer. In addition to the bridge oligo, the "bridged assay" consists of a forward primer picked from the genomic locus upstream of the bridge annealing region and the probe and reverse primer picked from the 5'-region of the bridge oligo. The bridged PCR detects only the digested end which can anneal and copy the bridge oligo. In addition, the bridged assay detected digested DNA sequences down to 1%, making it uniquely suitable for the measurement of low digestion efficiency typical of 3C-based methods. Paired with standard qPCR assays that use primers spanning the restriction site, the bridged assay provided accurate and precise quantitation of restriction and ligation efficiencies. By design-of-experiments, the restriction and ligation efficiencies were demonstrated as highly predictive of 3C library quality. Control assays were successfully designed and validated for common restriction enzymes (e.g. EcoR I, Bgl II, Tsp509 I, Hind III, Sau3A I, Dpn II and Alu I).

The restriction and ligation control assays were picked from a gene desert region, which is expected to have few changes among different cells and cell stages (see, FIG. 8). The target sequences for both EcoR I and Hind III were centered at a region that consists of the two restriction sites from human ENCODE gene desert region, ENr313 in chromosome 16 (>gi|42655553|ref|NT_086350.2|ENr313 *Homo sapiens* chromosome 16 sequence, ENCODE region ENr313). The combination of the assays was used to monitor both restriction and ligation.

Example 2

Figure 9:
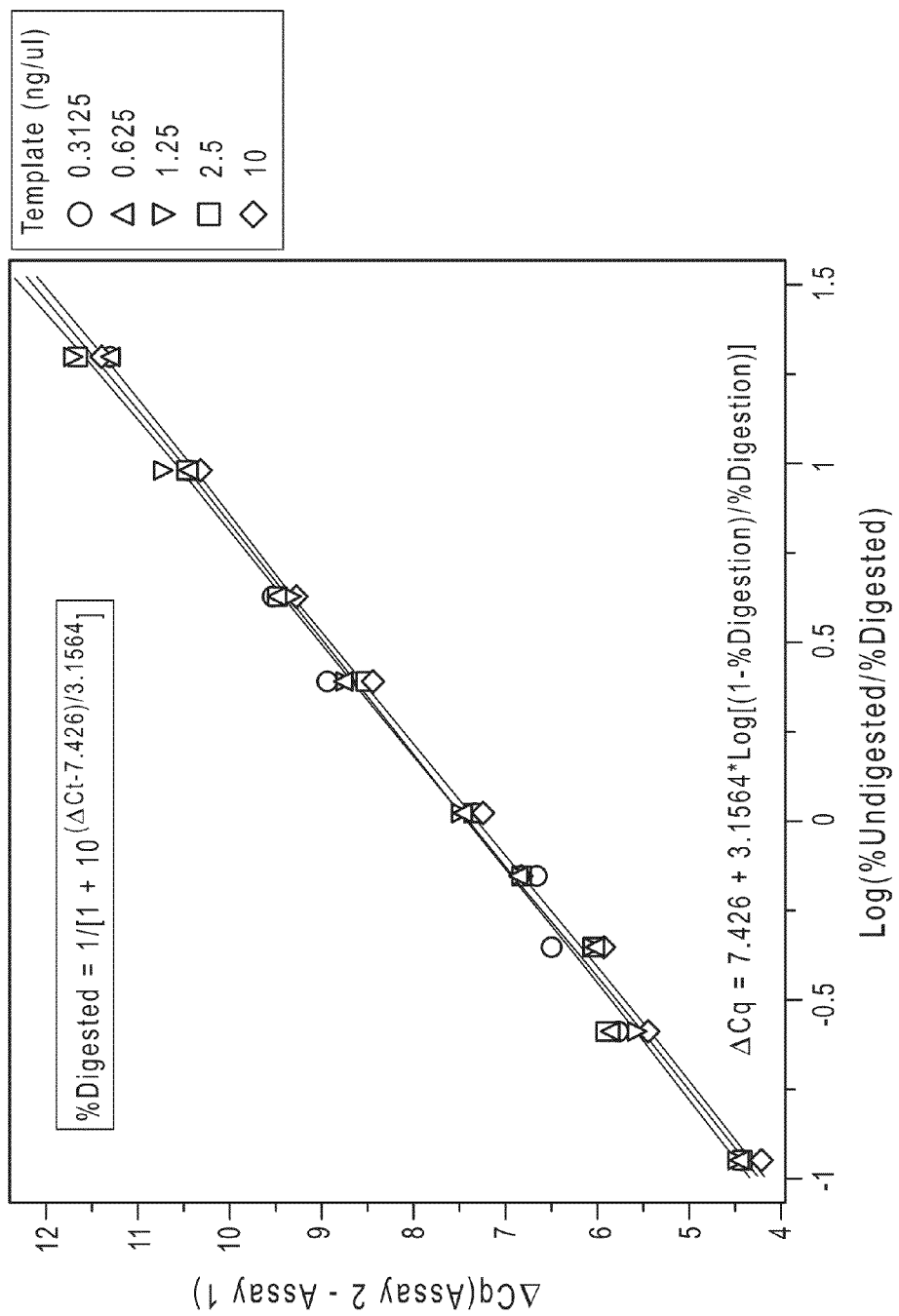
FIG. 9: Graphical depiction of quantitative measurement of restriction efficiency using the methods described herein (see Example 2).

Calculation of Digestion and Ligation Efficiency (FIG. 9)

Digestion and ligation efficiency may be calculated by qPCR Ct values of the control assays (i.e., Assays 1 and 2, see FIG. 2). The two qPCR assays were combined to provide high sensitivity and precision in efficiency measurement.

Assay 1 was designed to quantitate undigested (residual) template. Its Ct follows a standard qPCR response:

$$Ct_1 = -k_1 * \log(C_0 * \% \text{ Undigested}) + Ct_{10} \qquad \text{(Formula 1)}$$

wherein $Ct_1$ is the Ct value of Assay 1 in a test, $k_1$ is the absolute value of the standard curve slope, $C_0$ is total template concentration, % Undigested is the percentage of undigested template, and $C_{10}$ is the intercept of standard curve.

Assay 2, called a bridge assay, detects the amount of digested template. Its Ct response to digestion efficiency follows a standard qPCR equation:

$$Ct_2 = -k_2 * \log(C_0 * \% \text{ Digested}) + Ct_{20} \quad \text{(Formula 2)}$$

wherein $Ct_2$ is Ct value of Assay 2 in a test, $k_2$ is the absolute value of the standard curve slope, $C_0$ is total template concentration, % Digested is the percentage of undigested template at the assay site, and $C_{20}$ is the intercept of standard curve. Since % Undigested+% Digested=100%, % Undigested=1–% Digested.

The difference of Ct between Assay 2 and Assay1 may be calculated as follows:

$$\Delta Ct = Ct_2 - Ct_1 = -k_2 * \log(C_0 * \% \text{ Digested}) + Ct_{20}] - [-k_1 * \log(C_0 * \% \text{ Undigested}) + Ct_{10}] = \log [(\% \text{ Undigested}/\% \text{ Digested})^{(k_1/k_2)}] + (Ct_{20} - Ct_{10}) = k_1 * \log(\% \text{ Undigested}/\% \text{ Digested}) + \Delta Ct_0 - (k_1 - k_2) * \log(\% \text{ Undigested}/\% \text{ Digested}) \text{ when } k_1 = k_2 = k,$$
$$\Delta Ct = k * \log(\% \text{ Undigested}/\% \text{ Digested}) + \Delta Ct_0. \quad \text{(Formula 3)}$$

As a result, % Digested=$1/(1+10^{[(\Delta Ct-\Delta Ct_0)/k]}$. The values of k and $Ct_0$ can be measured by plotting $\Delta Ct$ versus log(% Undigested/% Digested).

Titration of the % Digested using EcoR I or Hind III digested genomic DNA validated the linearity of $\Delta Ct$(Assay2–Assay1) vs. Log(% Undigested/% Digested). A template amount of 0.31 ng/ul to 10 ng/μl in PCR did not shift the curve.

Final equations for restriction efficiency calculation:

$$\text{EcoR I: } \% \text{ Digestion} = 1/[1+10^{(\Delta Ct-4.404)/3.28}] \quad \text{(Formula 5)}$$

$$\text{Hind III: } \% \text{ Digestion} = 1/[1+10^{(\Delta Ct-5.66)/3.015}] \quad \text{(Formula 6)}$$

A standard ΔΔCt method may be used for ligation efficiency calculation.

$$\% \text{ Ligation} = 1 - \frac{1}{2}^{(\Delta\Delta Ct)}, \text{ where } \Delta\Delta Ct = \Delta Ct(Ct_2 - Ct_r)_{Digested} - \Delta Ct(Ct_2 - Ct_r)_{Ligated}. Ct_r: \text{Ct of reference assay.} \quad \text{(Formula 7)}$$

RNase P and other copy number reference assays may be used as long as they do not contain EcoR I and Hind III recognition sites and are of single copy per genome.

Example 3

Figure 10:
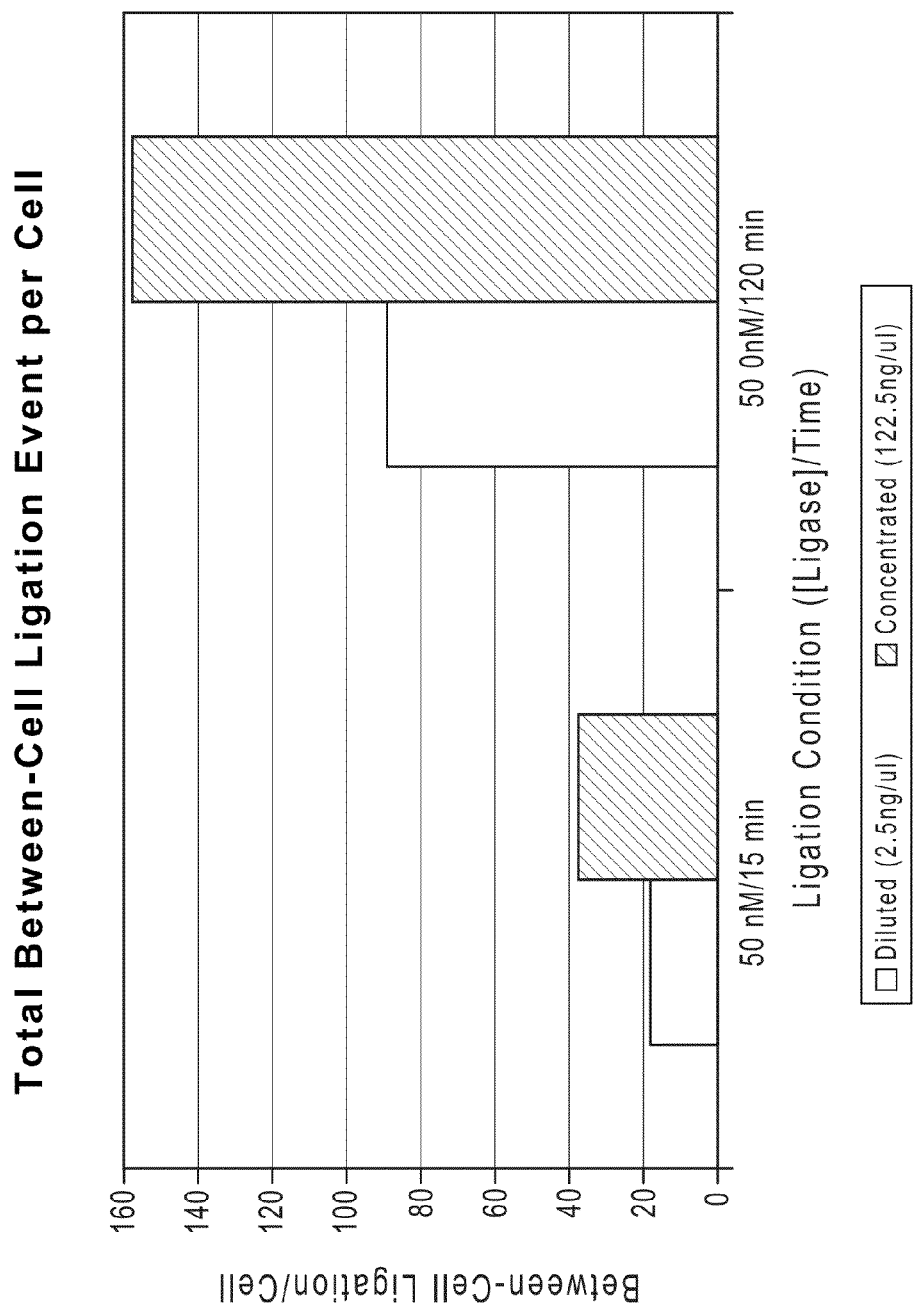
FIG. 10: Effects of reducing ligation volume on between-cell ligation events using the methods disclosed herein (see Example 3).
Figure 11:
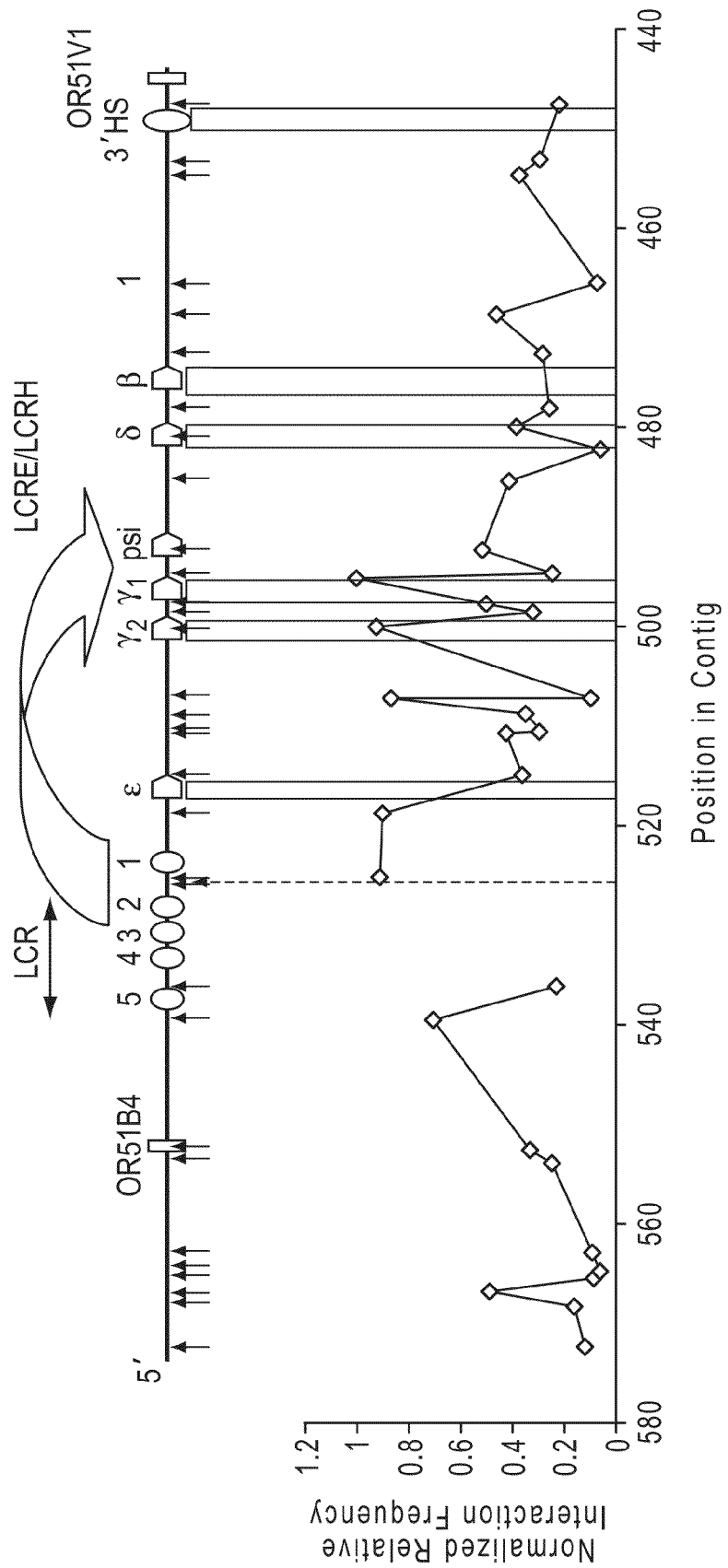
FIG. 11: A schematic of assay design and interaction detection for β-globin locus control region (LCR) (see Example 4).
Figure 12:
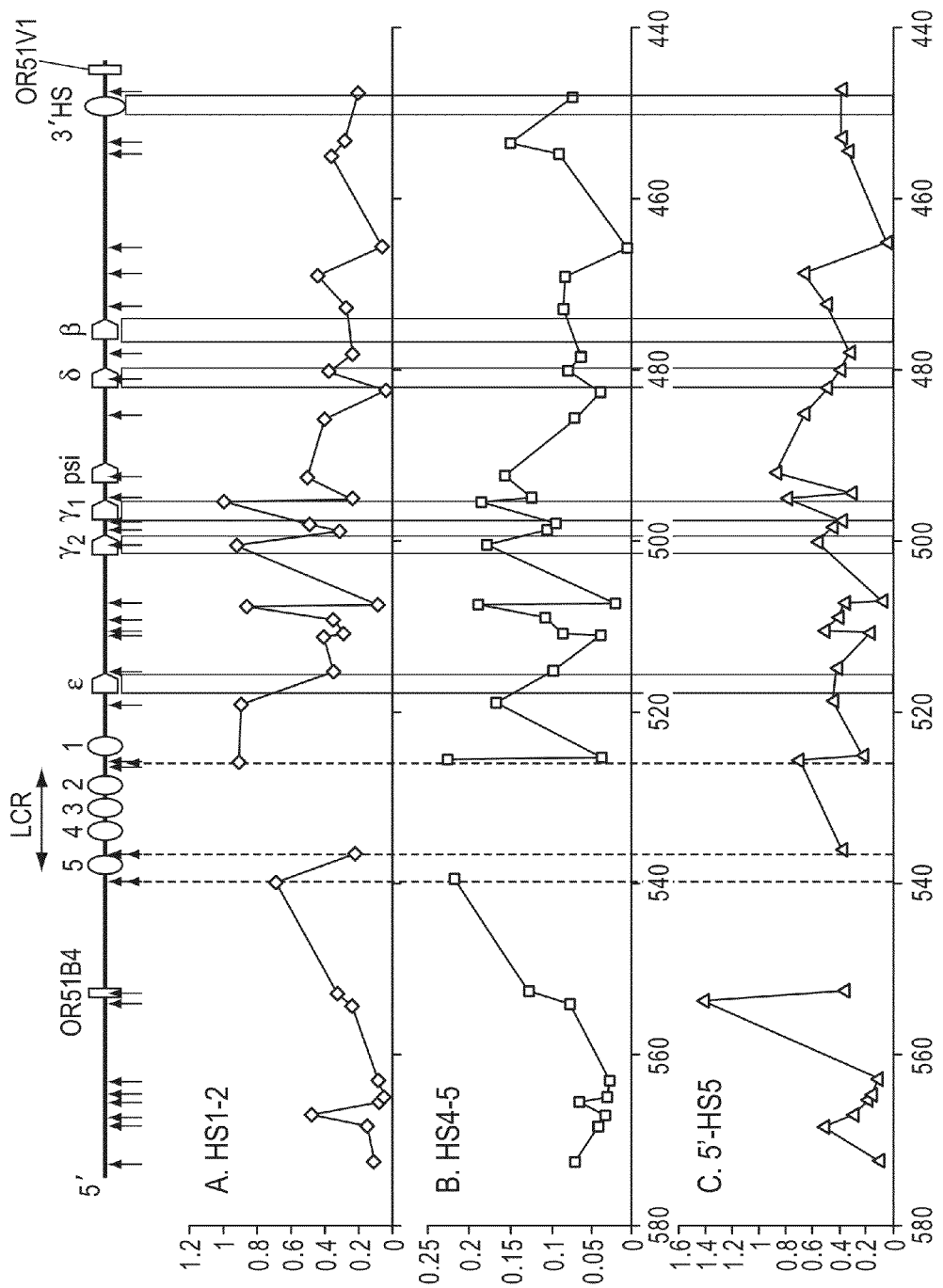
FIG. 12: A schematic summary of LCR interaction mapping (see Example 4).
Figure 13:
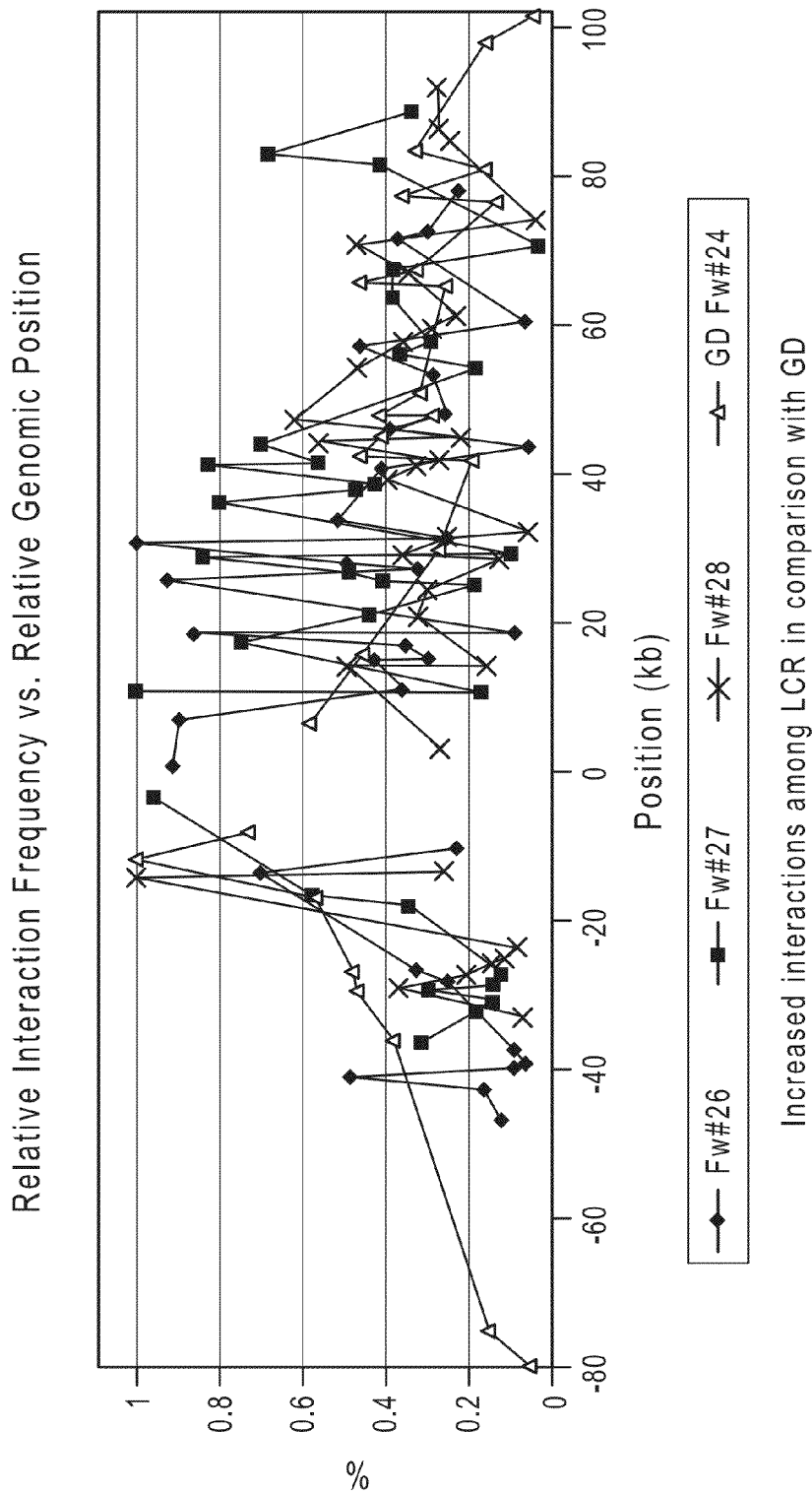
FIG. 13: A graphical representation of interaction frequency vs. distance as determined using the methods of the embodiments disclosed herein (see Example 4).
Figure 14:
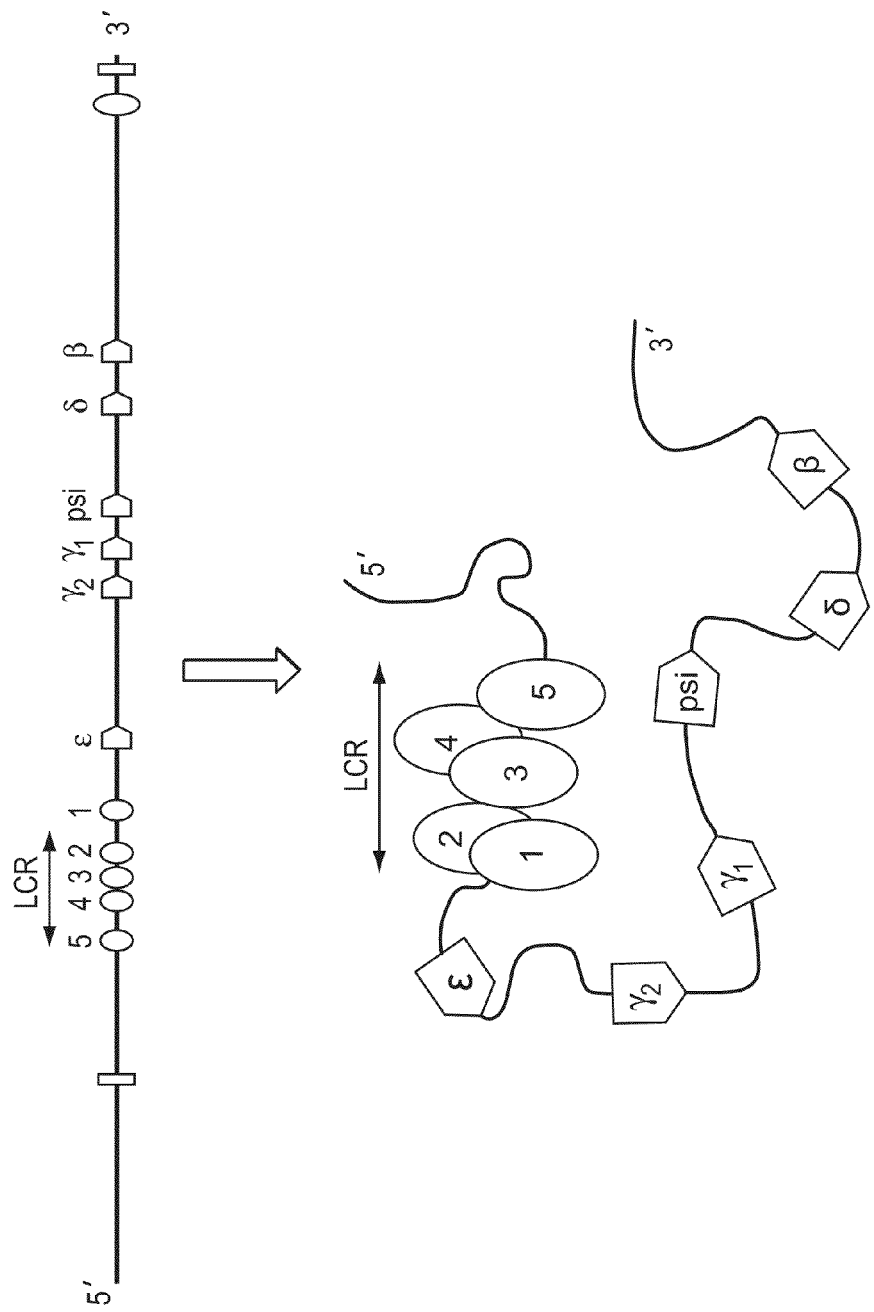
FIG. 14: A schematic diagram of three-dimensional interactions between LCR and β-globin genes as determined using methods of the embodiments disclosed herein (see Example 4).

Optimization of Ligation Volume and Reducing Between-Cell Ligation (FIG. 10)

Cells were cross-linked with 1% formaldehyde, lysed and digested with Alu I (400 U/5 million cells) in NEBuffer 2 (New England Biolabs, Ipswich, Mass.) for 1 hour at 37° C. Alu I was then heat inactivated at 65° C. for 20 min. Digested cells were spun down and washed with NEBuffer2. For filling-up and A-tailing, 5×10⁶ cells were mixed with 15 μl 10×NEBuffer 2, 1.5 μl 100 mM dNTP, 1 μl Klenow (exo⁻, 50 U/μl) in a final volume of 150 μl and incubated at 37° C. for 1 hr. Cells were then spun down and washed with NEBuffer 3. Cells were resuspended in 1× T4 ligase buffer, pooled and split into two reactions. Each reaction was ligated to a half-adaptor at the following conditions and incubated at 16° C. for 1 hr:

| | |
|---|---|
| Half-adaptor (50 μM) | 4 μl |
| 5× Invitrogen Ligase Buffer | 60 μl |
| T4 Ligase (1 mg/ml) | 15 μl |
| H₂O | 221 μl |
| Total Volume: | 300 μl |

The cells were spun down and washed twice with 500 μl 1× T4 ligase buffer. The separately ligated cells were resuspended in 1× T4 ligase buffer and mixed in equal portions, ligated at concentrations of 2.5, 25, 75, and 122.5 ng/μl gDNA equivalent (assuming a diploid genome) with different amounts of T4 ligase and varying the ligation time to evaluate the effects of cell concentration.

Ligation between cells was quantitated using TaqMan® assays designed to specifically amplify and detect sequences with the full adaptor (ligation product of two half-adaptors) located between two Alu repetitive sequences. Ligation event numbers were calculated by Ct values after normalization with RNase P (see, FIG. 10).

Ligation capacity (ligase concentration×ligation time) was the dominant factor for both long range interaction ligation and between-cell ligation, accounting for up to 70% of the variations in between-cell ligations. Reduction of the ligation volume by 49-fold only doubled the between-cell ligation events per cell regardless of ligation capacity. The increase of between-cell ligation was paralleled with increased ligation efficiency and was increased in a dose-dependent manner by cell concentration (a 4-fold increase by a 30-fold cell increase) regardless of the ligation capacity. Optimization of ligation amount and ligation time was more efficient in reducing non-specific ligation.

Example 4

Assays for Long-Range Interaction Detection (FIGS. 11-14)

To monitor interaction capture efficiencies, TaqMan® assays were designed to detect cross-ligated DNA sequences. 3C targets between human β-globin locus control region (LCR) and human β-globin (HBG), which are separated by about 40 kb, were used to monitor the interaction detection for euchromatin region and assays for heterochromatin were selected between two nearby sequences in a gene desert (see FIG. 8). Optimal lysis buffer and conditions were selected after comparison of different detergents and their combinations. Reagents and conditions for digestion, ligation and purification were optimized through systematic design-of-experiments and titrations. Cells of K562 and GM06990 were used at 1 to 10 million per reaction for the optimization. The experimental design is outlined below.

Long-Range Interaction Between LCR and β-Globin Experimentals:
Sample:
Bead purified 3C library of K562 cell lines
Pooled DNA from ligation
Pre-amplified vs. non-amplified comparison
CNV RNase P assays used for template quantitation with Jurkat gDNA (NEB) as standard
LCR Assays:
Loci 1 to 36 (out of 107)
3 LCR cutting sites: HS1-2 (#26), HS4-5 (#27) and 5'-HS5 (#28)
Combinations: #26Fw+#1-36 Fw; #27Fw+#1-36Fw; #27Fw+#1-36Rv; #28Fw+#1-36Fw; #27Rv+#1-36Rv; #27Rv+#1-36Fw
Gene Desert Assays:
24Fw+#14-77Fw; #74Fw+#14-77Fw 3 μl/10 μl PCR
Data Analysis:
Ct correction with BAC control library
PCR efficiency vs. Ct-based correction
LCR looping model qPCR assays were designed for 107 EcoR I sites around LCR and β-globin following TaqMan® assay criteria for human LCR sequence (>gi|42655566|ref|NT_086365.3|ENm009 *Homo sapiens* chromosome 11 sequence, ENCODE region ENm009). These assays were used to quantitate interaction frequencies between LCR with the β-globin genes (see, FIGS. 11 and 12). BAC clones were used to normalize qPCR efficiency of the assays. BAC DNA covering the targeted LCR region were isolated and mixed in equal ratio followed by restriction digestion by EcoR I or Hind III and ligation by T4 ligase.

Two assays that detected the strongest long-range interactions were selected: one between LCR HS 1-2 (F26) and HBG1 (F14) and another between LCR HS 4-5 (F27) and HBG1 (F14). These assays were validated for both EcoR I and Hind III 3C libraries. F26 interaction with F14 was four fold higher than F27 (FIG. 13 and data not shown), indicating the difference in their distance to F14. Variations in the response of these two assays to the process conditions disclosed herein are expected to reveal distance-dependence of capture efficiency changes. A three-dimensional schematic diagram for the genomic interactions between LCR and HBG based on the assays described above is shown in FIG. 14.

Example 5

Figure 15A:
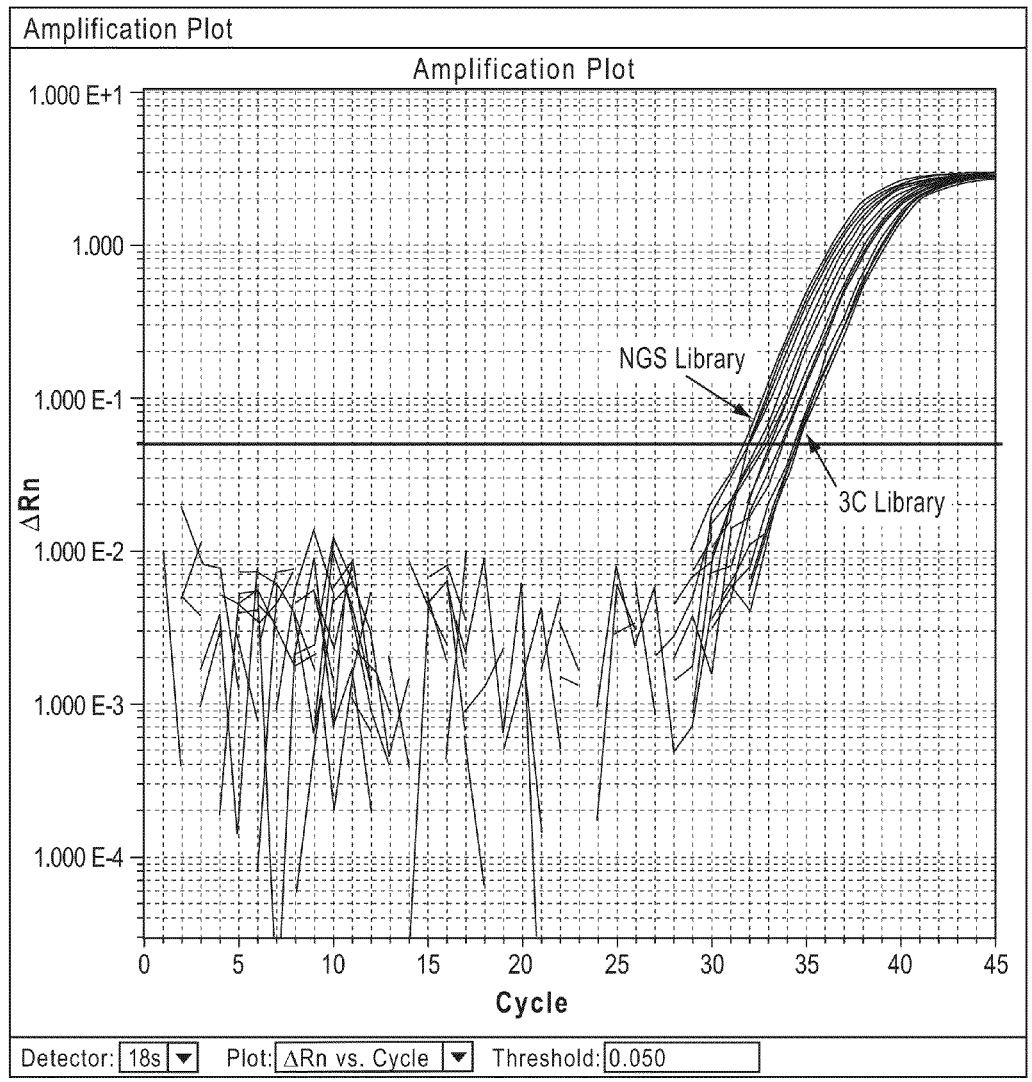
FIG. 15: Capture of the LCRE27-14 Interaction and comparison of the sensitivity of the interactions in the library created using the methods of the present teachings (NGS Library) compared to that of a 3C Library (see Example 5).
Figure 15B:
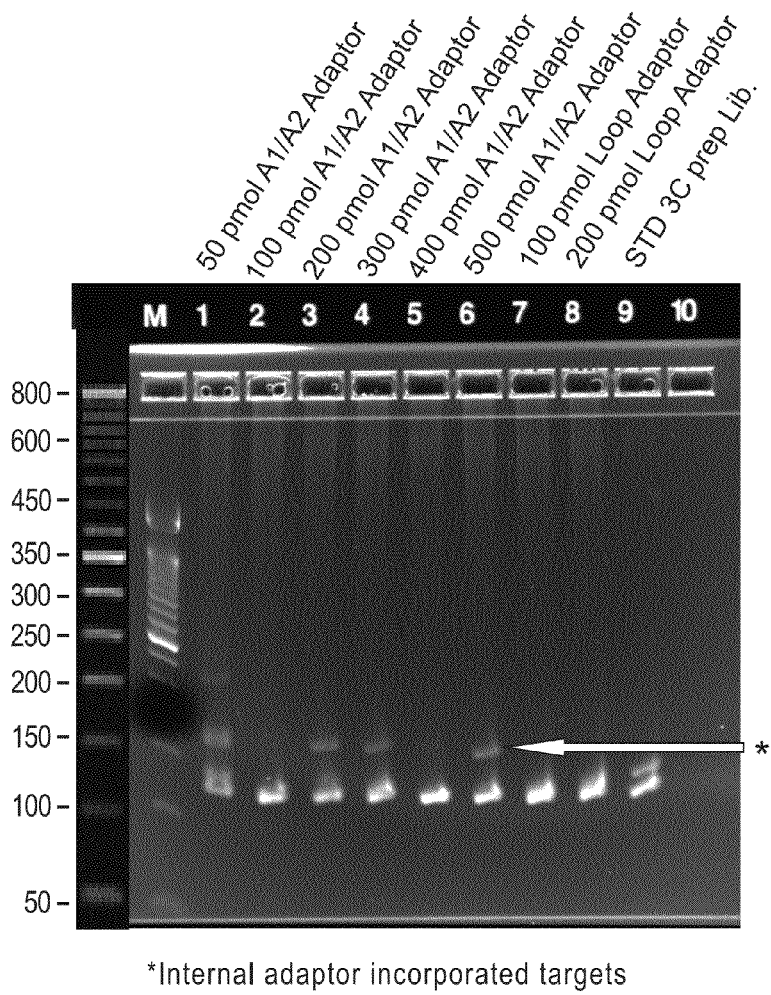

Capturing LCRE Interaction (FIG. 15)

Figure 16A:
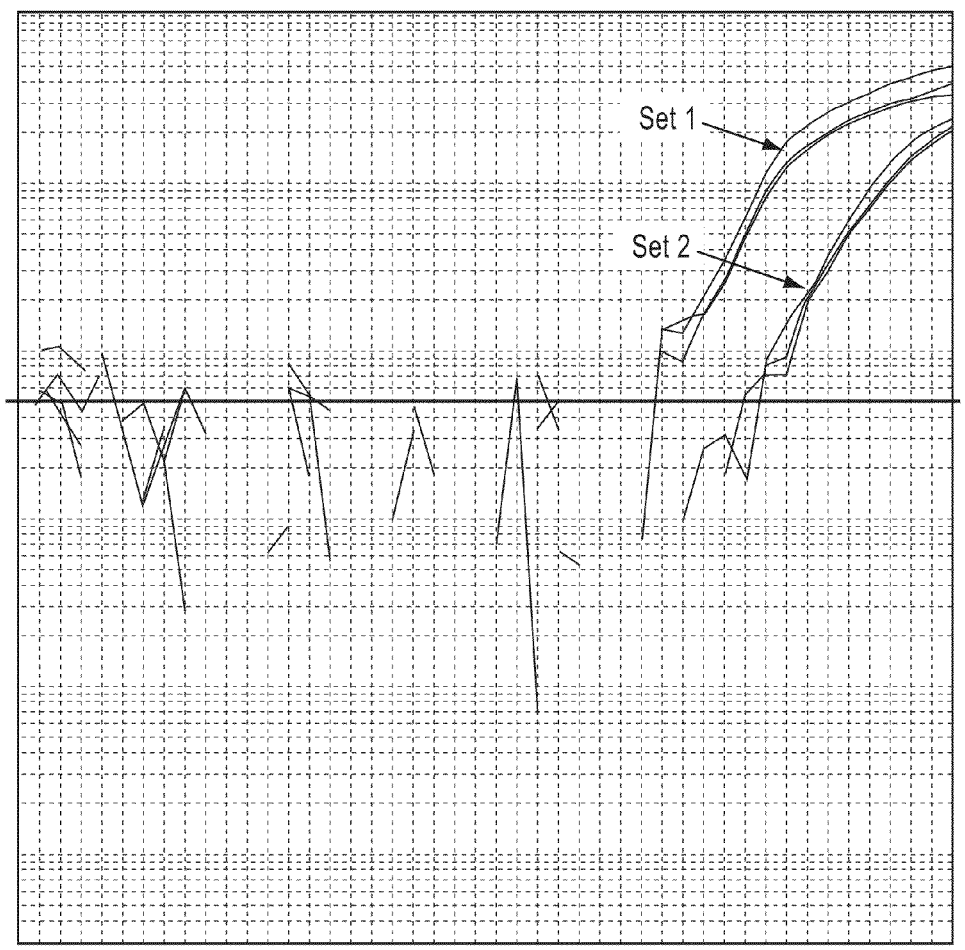
FIG. 16: Formation of a chromosome conformation library using the methods according to the embodiments disclosed herein for analysis using next generation sequencing methods (see Example 6).
Figure 16B:
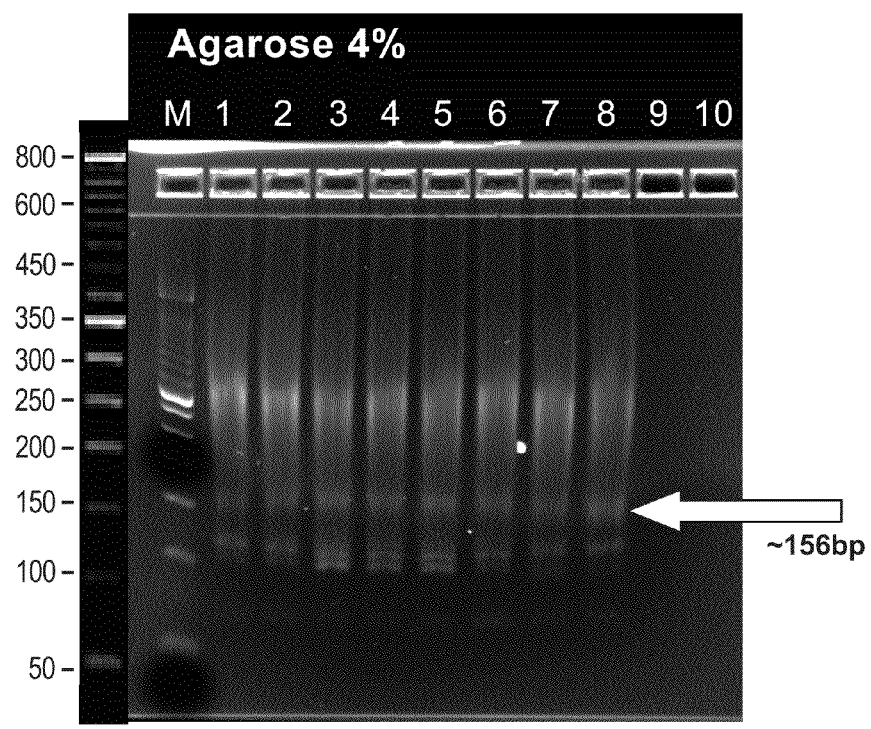

TaqMan® assays were designed with a forward primer and probe targeting the Eco RI upstream sequence located between LCR HS4 and LCR HS5 and a reverse primer from the HBG1 region. PCR reactions were run on a 7900HTS real-time PCR machine (Life Technologies, Foster City, Calif.) using TaqMan® Gene Expression Master Mix (Life Technologies, Foster City, Calif.) at standard cycling conditions to generate the amplification plot (FIG. 16). PCR products were loaded on a 4% agarose gel and run on an E-gel system (Life Technologies, Carlsbad, Calif.). Sequences amplified from templates without adaptors were detected at ~120 bp and those from templates with full adaptors were detected at ~150 bp (FIG. 16).

Cells of K562 were processed using the chromosome interaction methods disclosed herein until the DNA purification step. Linear half-adaptors were used for gel lanes 1-6 at the indicated concentration. Looped adaptors were used for gel lanes 7 and 8. Lane 9 shows the PCR product for a 3C library (see, FIG. 15).

Example 6

Complete 3C Library Generation (FIG. 16)

DNA libraries were generated according to the methods disclosed herein until the library amplification step. PCR products were analyzed on 4% agarose gels. Expected products were detected at ~156 bp. Lanes 1-8 of FIG. 16 correspond to lane 9 in FIG. 15.

Example 7

Identification of Epigenetic Networks in Breast Cancer (FIGS. 17-21)

Epigenetic mechanisms are essential for normal development and maintenance of normal gene expression pattern in many organisms including humans. Recent studies suggest that epigenetic alterations may be the key initiating events in some forms of cancers and global changes in the epigenome are a hallmark of cancers. Phospolipase D (PLD) catalyzes the hydrolysis of phosphatidylcholine to generate the lipid second messenger, phosphatidic acid (PA), and choline and regulates multiple cellular pathways. Elevated PLD1 has been demonstrated to promote cell proliferation and has been associated with the progression and metastasis of multiple cancers. In certain embodiments, the chromosomal conformation methods described herein may be used to elucidate the changes in chromatin organization, DNA methylation and miRNA expression that underlies the aberrant expression level of PLD1 in breast cancers. Differences in PLD1 expression and the epigenetic network between tamoxifen responsive (MCF-7) and non-responsive (MDA-MB-231) breast cancer cell lines were compared to associate epigenetic changes with their cancer phenotypes. Effects of DNA demethylation and histone acetylation induced by the methyltransferase inhibitor 5-aza-2'-deoxycytidine and the histone deacetylase inhibitor Trichostatin A were also investigated to provide insights into the molecular mechanisms of epigenetic drugs.

Epigenetic mechanisms that modify chromatin structure can be divided into four main categories: 1) DNA methylation, 2) covalent histone modifications and noncovalent mechanisms such as incorporation of histone variants, 3) nucleosome remodeling and 4) non-coding RNAs which include miRNAs. The role of DNA methylation and histone modifications in cancer initiation and progression is well established; however, the changes in chromatin structure that accompany DNA methylation and histone modifications are less well understood.

Two breast cancer cell lines, MCF-7 and MDA-MB-231 were obtained from the American Type Culture Collection (ATCC). Drugs used to treat cells such as 5-Aza-2'-deoxycytidine, Trichostatin A, Phorbol 12-myristate 13-acetate (tumor promoter, PKC activator), 4-hydroxytamoxifen (Tamoxifen) and β-estradiol were purchased from Sigma (St. Louis, Mo.). Assays used for miRNA profiling, methylation, and Taqman® gene expression were obtained from Life Technologies (Carlsbad, Calif.). The list of breast cancer markers, assays and gene symbols used in this example are disclosed in Tables 2-4, below.

TABLE 2

| List of Breast Cancer Markers | |
|---|---|
| Tumor Suppressors | Cancer Type |
| APC | Lung, colon, breast, gastric, liver |
| BLC2 | Bladder, colon, breast, prostate |
| HS3ST2 | Pancreas, lung, breast, colon, skin, gall bladder |
| IGF2A S | Colon |
| PTEN | Skin, lung, breast |
| RPRM | Esophageal, lung, pancreas |
| SCGB3A1 | Prostate, breast, lung, nasopharyngeal, pancreas |
| SYK | Breast, gastric, liver |
| ZMYND10 | Cervical, lung, nasopharyngeal, brain, liver |
| PLD1 | Overexpressed in many cancers |

TABLE 3

Assays and Their Targets

| Assay Name | Target | Functional Pathway | Function |
|---|---|---|---|
| hsa-miR-206 | ESR-1 | ER signaling | Tumor suppressor miRNA |
| mo-miR-17-5p | E2F1, AlB1, CCND1 | Proliferation | Tumor suppressor miRNA |
| hsa-miR-125a-3p | Her2, Her3 | Anchorage dependent growth | Tumor suppressor miRNA |
| hsa-miR-125a-5p | Her2, Her3 | Anchorage dependent growth | Tumor suppressor miRNA |
| hsa-miR-200b | BMI1, ZEB1, ZEB2 | TGF-B signaling | Tumor suppressor miRNA |
| hsa-let-7a | H-ras, HMGAS2, LIN28, PEBP1 | Proliferation, differentiation | Tumor suppressor miRNA |
| hsa-miR-34a | CCND1, DCK6, E2F3, MYC | DNA damage, proliferation | Tumor suppressor miRNA |
| hsa-miR-31 | FZD3, ITGA5, M-RIP, MMP16, RDX, RHOA | metastasis | Tumor suppressor miRNA |
| hsa-miR-21 | BCL-2, TPM1, PDCD4, PTEN, MASPIN | Apoptosis | Oncogenic miRNAs |
| hsa-miR-155 | RHOA | TGF-B signaling | Oncogenic miRNAs |
| hsa-miR-10b | HOXD10 | Metastasis | Oncogenic miRNAs |
| hsa-miR-373 | CD44 | Metastasis | Oncogenic miRNAs |
| hsa-miR-16 | Control | Control | Control |
| RNU44 | Control, *Homo sapiens* | Control | Control |
| RNU48 | Control, *Homo sapiens* | Control | Control |

TABLE 4

| Gene Symbols | Gene Symbols |
|---|---|
| PLD1 (exon 15/16) | MAPK3 |
| PLD1 (exon 1/2) | CDKN1A |
| ERAF | PRKAR1A |
| ESR1 | PPM1D |
| ESR2 | PIK3CA |
| TP53 | APC |
| CTNNBL1 | BCL2 |
| TCF7L2 | HS3ST2 |
| KRAS | IFG2AS |
| BRMS1L | PTEN |
| PBQV1 | RPRM |
| AR | SCGB3A1 |
| BCAR4 | SYK |
| CAMK2B | ZYMKD10 |
| BRCA2 | ACTB |
| BRMS1L | GAPDH |

Figure 17:
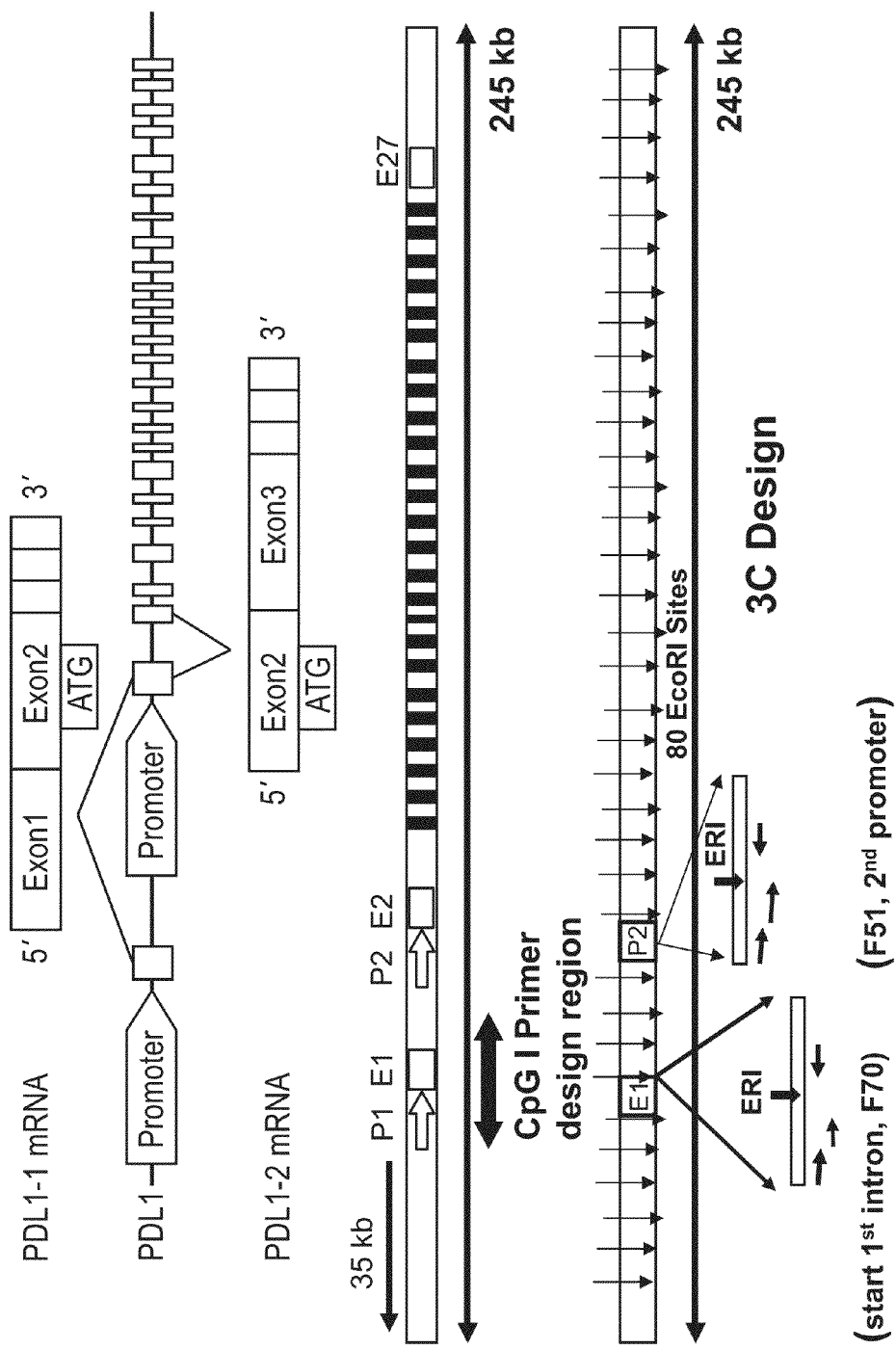
FIG. 17: A diagrammatic representation of phospholipase D 1 (PLD1) genes and assay designs according to embodiments of the present teachings.
Figure 18B:
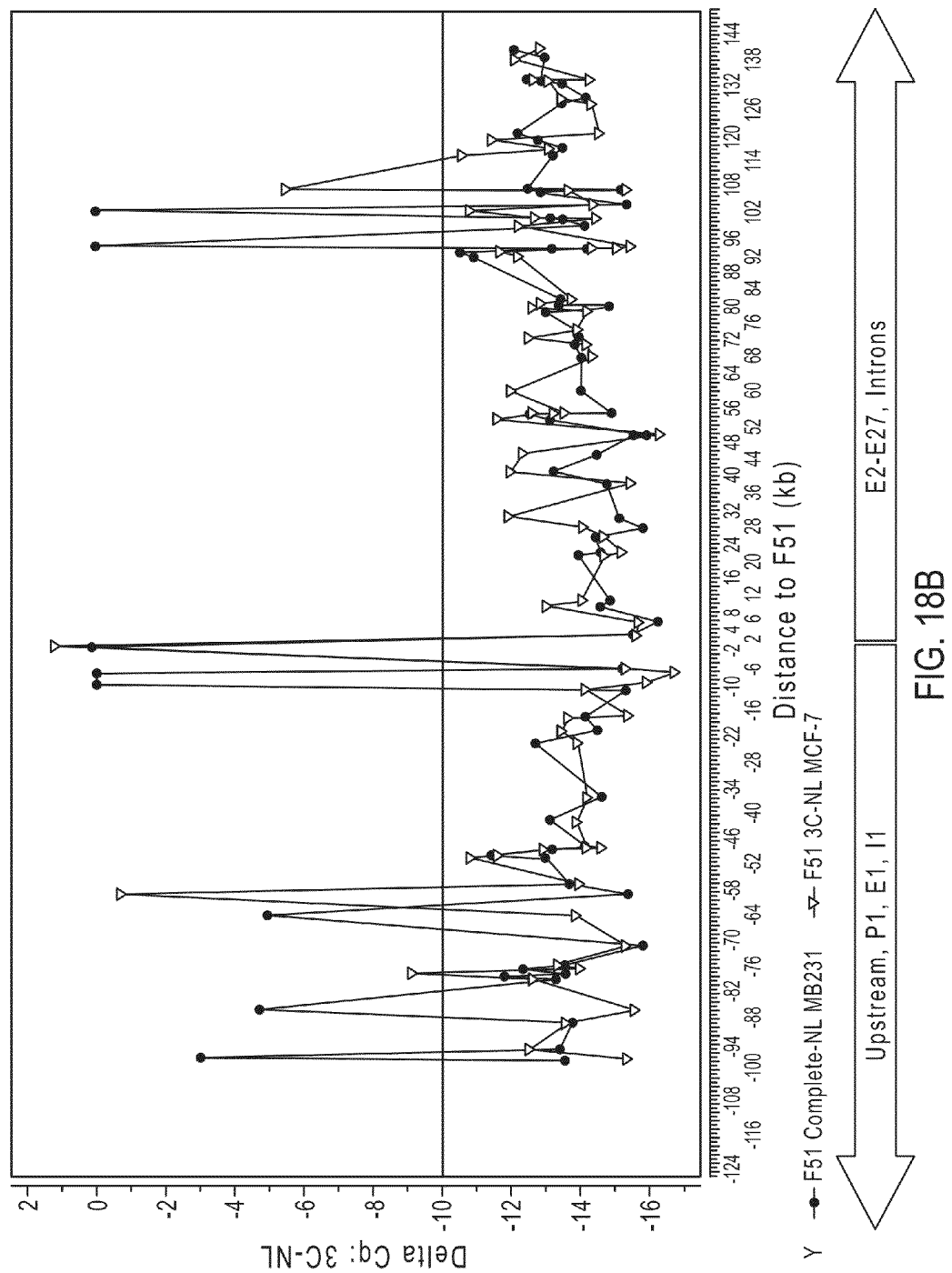
Figure 19A:
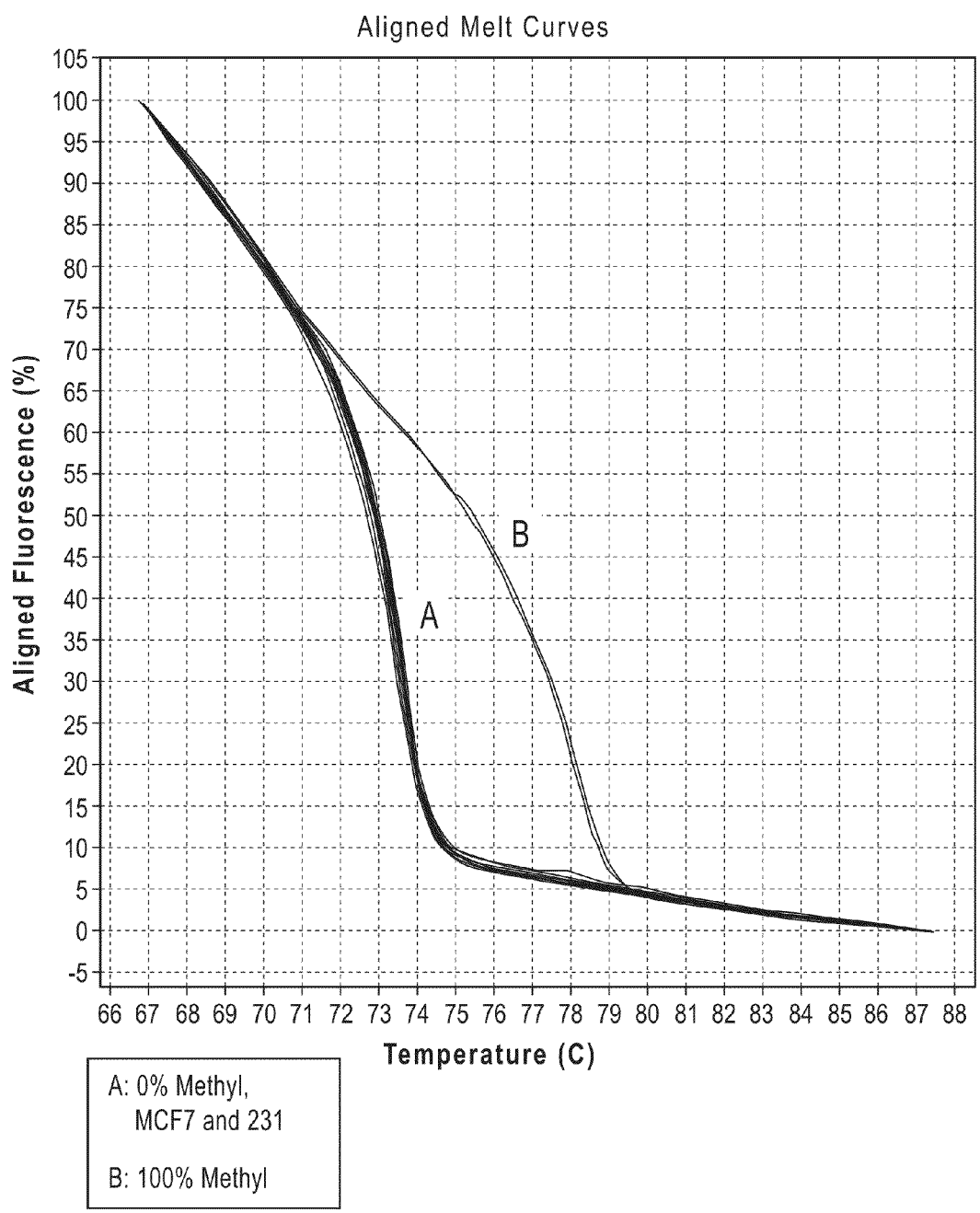
FIG. 19: Graphical representation of PLD1 methylation (FIG. 19A) and expression (FIG. 19B) in MCF-7 and MDA-MB-231 cells.
Figure 19B:
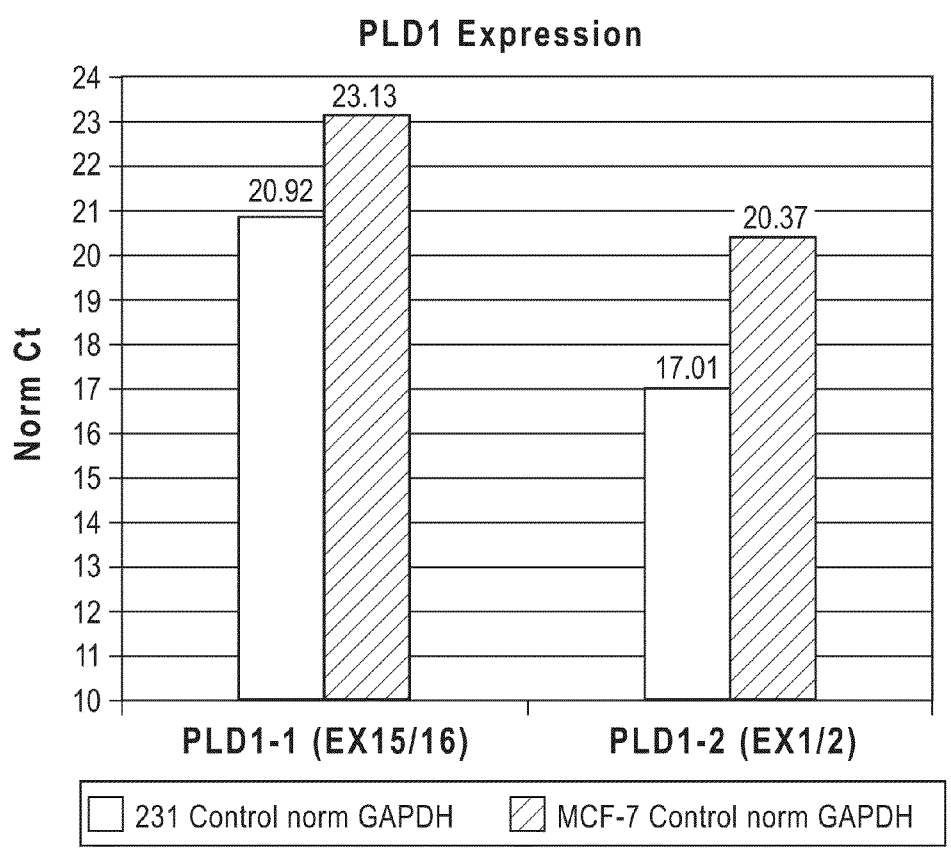

FIG. 17 shows a diagrammatic representation of PLD1 genes and the assay designs using the chromosomal conformation methods according to the embodiments disclosed herein. PLD1 Intron 1 and PLD1 Promoter 2 were used as anchors to capture other downstream cis interactions across the whole gene using the chromosome conformation methods disclosed herein. In FIGS. 18A and B, the x-axis shows the distance (kb) of the downstream (upstream) primers (EcoRI sites) to Intron 1 or Promoter 2. The y-axis shows the relative interaction frequencies based on qPCR Ct ($\Delta$Ct). The lower the $\Delta$Ct, the higher the interaction frequency. Comparing the MDA-MB-231 results with those of MCF-7, the difference in the long distance interaction frequency between these two cell lines is apparent. This difference could possibly explain the differences in drug response of these two types of breast cancer patients.

The methylation (FIG. 19A) and expression (FIG. 19B) of PLD1 were compared between the two cell lines. As can be seen in the figures, the PLD1 expression level for both Promoter 1 and Promoter 2 were compared. The expression ratio of MDA-MB-231 to MCF-7 for Promoter 1 alone is 10, and for Promoter 1 and 2 together is 5. Both cell lines are unmethylated in this region (data not shown).

Figure 20A:
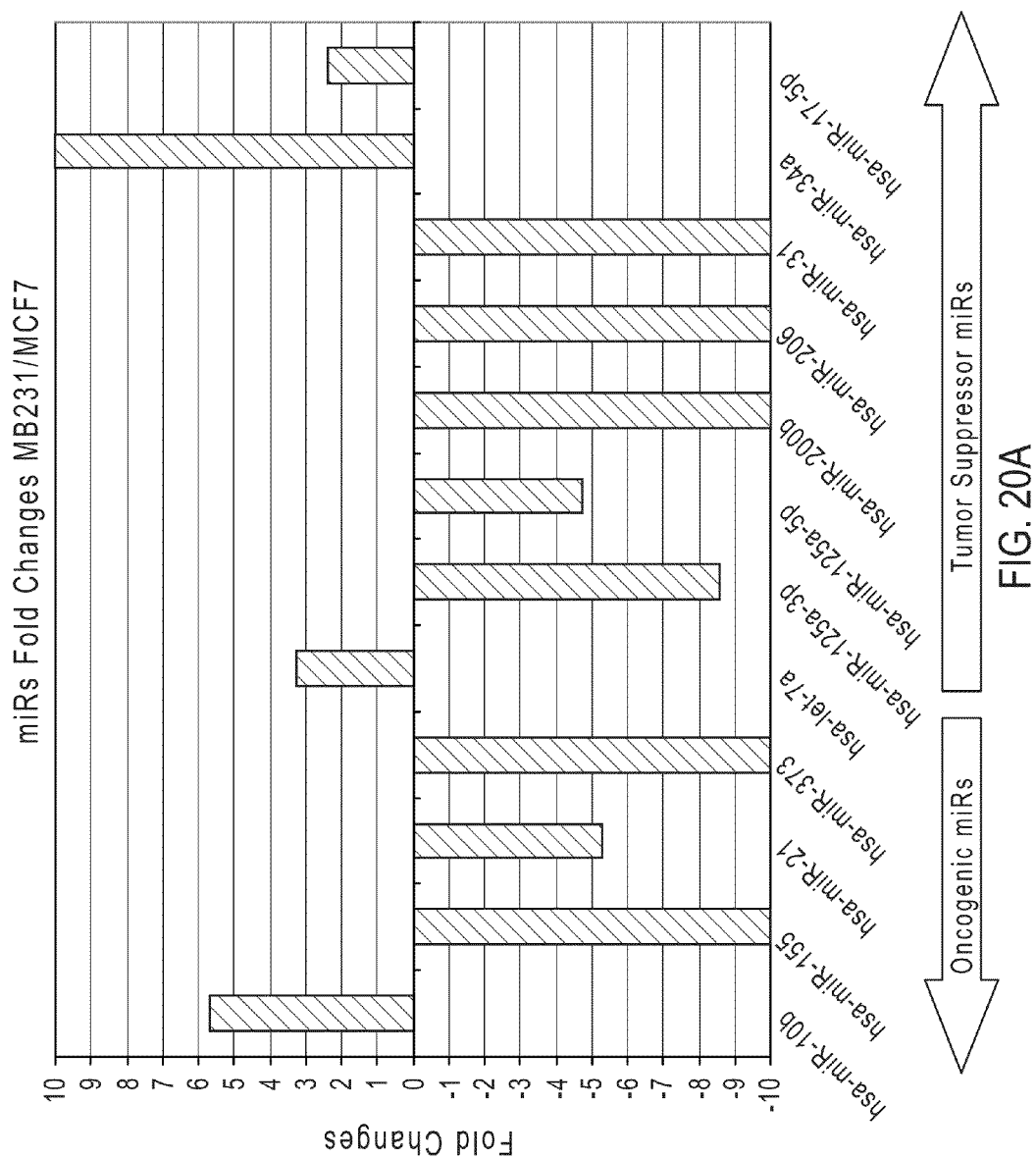
FIGS. 20A and 20B: Graphical representation of a comparison of cancer marker genes and microRNA in MCF-7 and MDA-MB-231 cells.
Figure 20B:
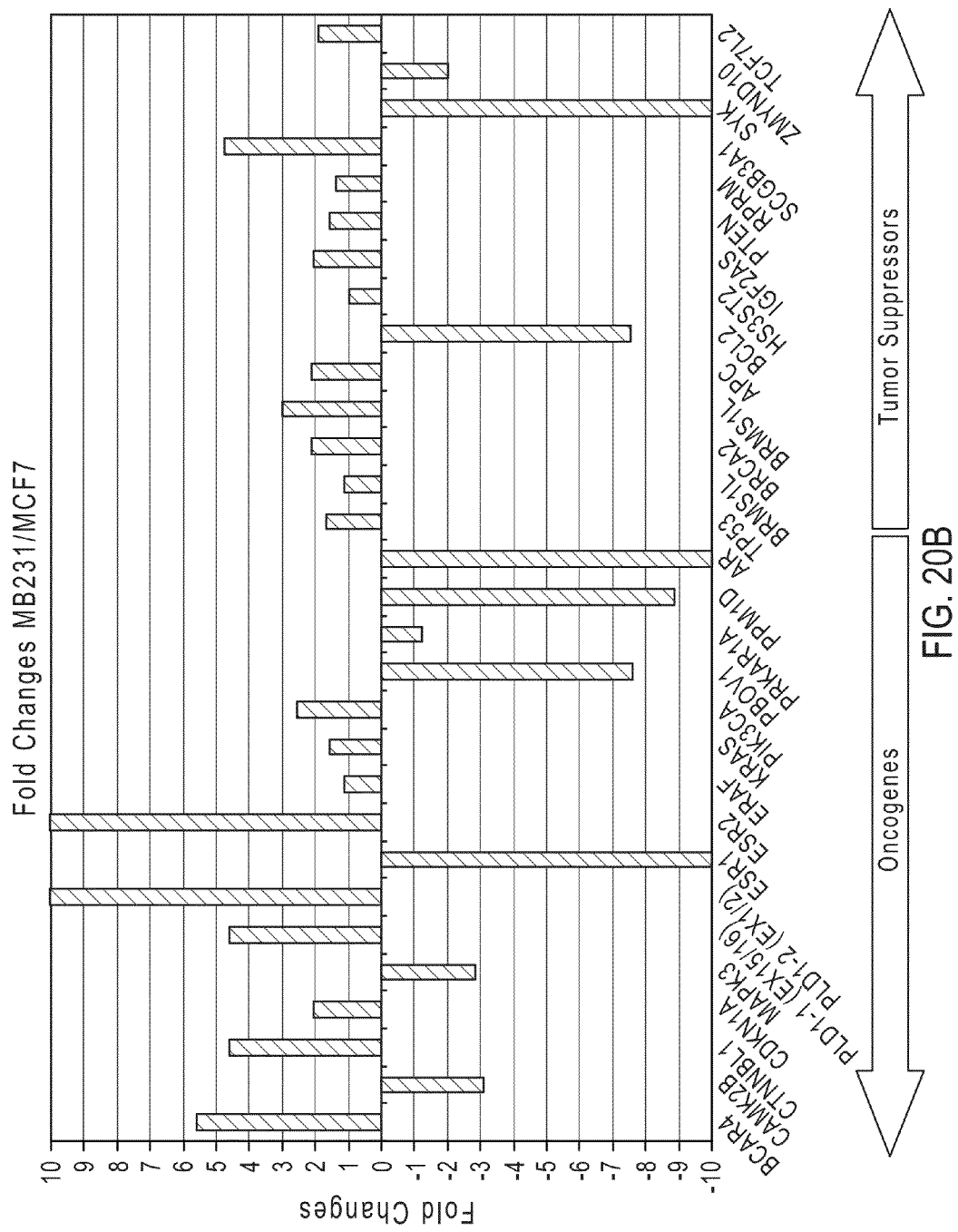

FIG. 20 shows a comparison of cancer marker genes and microRNAs for the two cell lines. FIG. 20A shows 12 cancer marker microRNAs including four oncogenic and eight tumor suppressors which were compared between MCF-7 and MDA-MB-231. Expression levels were normalized by RNU44 and RNU48. FIG. 20B shows the expression level of 30 cancer marker genes including 14 tumor suppressors (10 of which were also compared for methylation) and 16 oncogenic genes were compared.

Figure 21A:
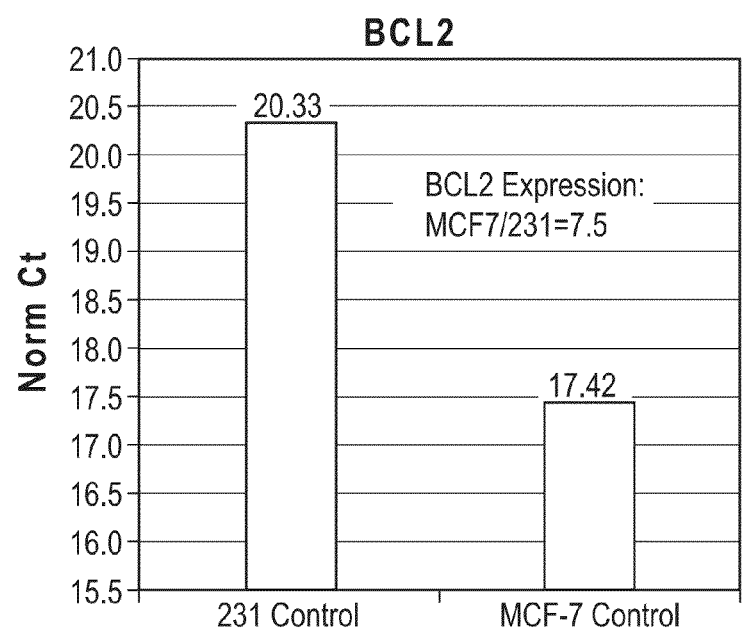
FIG. 21: Graphical representation of MIR21 (FIG. 21B) and targeted tumor suppressor gene BCL2 (FIG. 21A) expression and CpG methylation in MCF-7 and MDA-MB-231 cells.
Figure 21B:
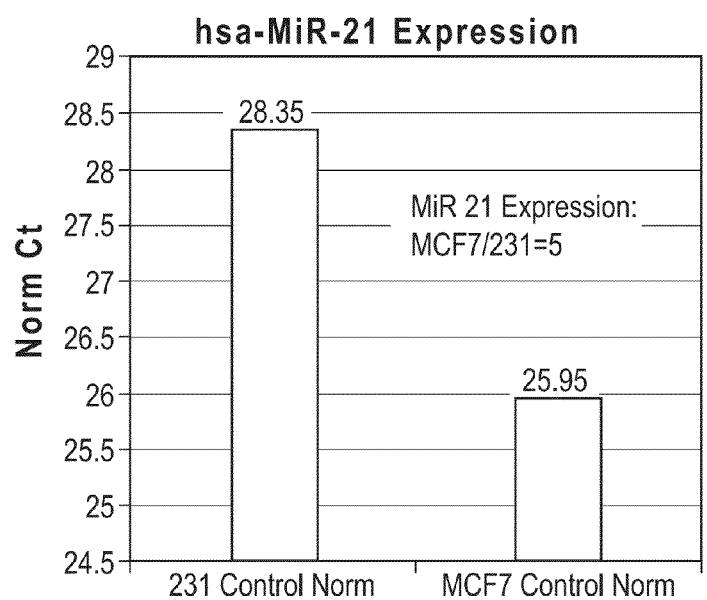

FIG. 21 shows a comparison of the methylation of CpGs (13 total) in the BCL-2 promoter region (350 bp from the transcription start) which showed differential methylation: 0% methylation in MCF-7 and 100% methylation in MDA-MB-231. BCL2 gene expression levels were compared resulting in an almost 8-fold higher expression in MCF-7, which is consistent with the hypermethylation in MDA-MB-231. In addition, oncogenic MiR21 was expressed about 5-fold higher in MCF-7.

Epigenetic alterations could explain the aberrant expression of many genes which contribute to the alteration of metastasis. Comparison of the epigenetic changes in chromatin 3D structure of PLD1 genes, changes of methylation in breast cancer-related tumor suppressor genes and expression level changes of microRNAs between two breast cancer cells lines was performed. In addition, the expression of metastasis and tumor suppressor genes was also compared. The 3D structure of PLD1 indicates there are more interactions of both Intron 1 and Promoter 2 with other cis elements across the 215 kb gene in the less metastasized MCF-7 cell line. However, the expression level of PLD1 is much higher in more metastasized MDA-MB 231 cells. 3D structure changes could potentially explain the expression level changes which in turn, explain the metastasis changes. PLD1 3D structure changes upon epigenetic drug treatments were also captured (data not shown). Another important epigenetic modification, methylation, was also monitored. Between the two cell lines, most tumor suppressor genes showed hypermethylation in MDA-MB 231, which is consistent with most observations. Furthermore, gene expression level of promoters in the methylation study was also measured. The data disclosed herein showed no absolute correlation between methylation and gene expression level changes. MicroRNA profiling showed over expression of both oncogenic and tumor suppressor microRNAs in MCF-7 in majority of microRNAs included in the study. The comparison of oncogenic MiR21 and its target gene BCL2 showed a negative correlation.

ing a second ligation product, wherein the first and second looped half-adaptors are different from each other and each looped half-adaptor comprises a stem-loop structure complementary to the stem-loop structure of the other half-adaptor, wherein the 5' end of the stem of each looped half-adaptor comprises a 5'-overhang that terminates in a 5'-phosphate group and is ligated to the digested DNA;

g) heating the first and second ligation products thereby allowing the half-adaptors to anneal to each other;

h) treating the product of step g) with a kinase and a ligase to ligate the looped half-adaptors to the digested DNA thereby forming a third ligation product; and i) analyzing the third ligation product.

We claim:

1. A method of determining the three-dimensional arrangement of the chromatin within a cell, comprising:
   a) isolating cells from a biological sample;
   b) incubating the cells with a cross-linking agent, thereby cross-linking proteins with DNA and forming a cross-linked product;
   c) lysing the cells;
   d) digesting the DNA with a restriction endonuclease;
   e) incubating the digested DNA with a phosphatase;
   f) ligating a first looped half-adaptor to the digested DNA thereby forming a first ligation product and a second looped half-adaptor to the digested DNA thereby form- 2. The method according to claim 1, wherein the analyzing step is performed using the polymerase chain reaction (PCR).

3. The method according to claim 1, further comprising the step of incubating the cross-linked product with a cross-linking quencher.

4. The method according to claim 1, wherein the lysing step comprises incubating the cells with one or more detergents.

5. The method according to claim 4, wherein the one or more detergents are selected from the group consisting of anionic detergents and non-ionic detergents.

6. The method according to claim 1, wherein the cross-linking agent comprises formaldehyde.

* * * * *

SEQUENCE LISTING

```
<160> NUMBER OF SEQ ID NOS: 1

<210> SEQ ID NO 1
<211> LENGTH: 560
<212> TYPE: DNA
<213> ORGANISM: Homo sapiens

<400> SEQUENCE: 1
ttcagaatgg aacatatcgg aagatacatg cttttgagaa gaaaagggga ttttatgatg      60
gtgtgctgaa gccataatat ggctggataa tcctattttt cttttatttt aaaaaatact     120
ctgaaatact tttaaaaata aacttttatt tcttcctagt gttgtgagaa aagaggccct     180
tcctctatgc ccacggtaga attccaagat ctgctcttta ctgccaagtc ttggagtcga     240
gattaatcac atctaattct taagcttaga acttaatgtg acagataagt agcttgaaat     300
aagcttcata tcttcattag tgttgtataa ttgaaaaaaa agaatatttt tatatcatga     360
ttgtactctt caaaaattct tccaaaacat agtcccaaac cactacaaat gtcttagaag     420
tgggacttag aaagctcctc aaagagctga aacaattgtc ttccagaatt caagaaacca     480
ttgtcgaaag tgaagaataa tttgttaatt cattttatct aaaactacag tatgacttcc     540
cattctcatt cccagtgaca                                                 560
```